(12) United States Patent
Zelisko et al.

(10) Patent No.: US 9,481,766 B2
(45) Date of Patent: Nov. 1, 2016

(54) SILOXANE-CONTAINING HYBRID MATERIALS

(71) Applicant: Brock University, St. Catharines (CA)

(72) Inventors: Paul M. Zelisko, Stoney Creek (CA); Mark B. Frampton, Thorold (CA)

(73) Assignee: Brock University, St. Catharines, Ontario (CA)

( * ) Notice: Subject to any disclaimer, the term of this patent is extended or adjusted under 35 U.S.C. 154(b) by 0 days.

(21) Appl. No.: 14/645,974

(22) Filed: Mar. 12, 2015

(65) Prior Publication Data

US 2015/0259478 A1 Sep. 17, 2015

Related U.S. Application Data

(60) Provisional application No. 61/951,723, filed on Mar. 12, 2014.

(51) Int. Cl.
| | |
|---|---|
| *C08G 77/14* | (2006.01) |
| *C07F 7/21* | (2006.01) |
| *C09D 183/06* | (2006.01) |
| *C12P 9/00* | (2006.01) |

(52) U.S. Cl.
CPC ............ *C08G 77/14* (2013.01); *C07F 7/21* (2013.01); *C09D 183/06* (2013.01); *C12P 9/00* (2013.01)

(58) Field of Classification Search
CPC ...... C08G 77/045; C08G 18/615; C07F 7/21
See application file for complete search history.

(56) References Cited

U.S. PATENT DOCUMENTS

| | | | |
|---|---|---|---|
| 4,465,712 A | 8/1984 | McVie | |
| 5,417,744 A | 5/1995 | Gasmena | |
| 7,288,283 B2 | 10/2007 | Wang et al. | |
| 7,868,198 B2 | 1/2011 | Laine et al. | |
| 2004/0120915 A1* | 6/2004 | Yang | A61K 8/585 |
| | | | 424/70.13 |
| 2005/0142054 A1 | 6/2005 | Hasegawa et al. | |
| 2009/0012317 A1 | 1/2009 | Laine et al. | |
| 2011/0062619 A1 | 3/2011 | Laine et al. | |

OTHER PUBLICATIONS

Reis, P. et al., "Lipases at Interfaces: A Review", Adv. Colloid. Interface., 2009, 147-148, 237-250.
Uppenberg. J., et al., "Crystallographic and Molecular-Modeling Studies of Lipase B from Candida antarctica Reveal a Stereospecificity Pocket for Secondary Alcohols", Biochemistry., 1995, 34, 16838-16851.
Kulshrestha, A. S., et al., "Synthesis and Characterization of Branched Polymers from Lipase-Catalyzed Trimethylolpropane Copolymerizations", Biomacromolecules., 2007, 8, 1794-1801.
Frampton, M. B., et al., "Biocatalytic Synthesis of Silicone Polyesters", Biomacromolecules., 2010, 11, 1818-1825.
Garcia-Alles, L. F., "Alcohol Inhibition and Specificity Studies of Lipase B from Candida antarctica in Organic Solvents", Biotechnol. Bioeng., 1998, 59, 163-170.
Poojari, Y. et al., "Lipase Catalyzed Synthesis of Silicone Polyesters", Chem. Commun., 2009, 6834-6835.
Frampton, M. B. "Synthesis of Lipase-Catalysed Silicone-Polyesters and Silicone-Polyamides at Elevated Temperatures", Chem. Commun., 2013, 49, 9269-9271.
Pleiss, J. et al., "Anatomy of Lipase Binding Sites; The Scissile Fatty Acid Binding Site", Chem. Phys. Lipids., 1998, 93, 67-80.
Gross, R. A. et al., "Polymer Synthesis by In Vitro Enzyme Catalysis", Chem. Rev. 2001, 101, 2097-2124.
Kobayashi, S. et al., "Enzymatic Polymerization", Chem. Rev. 2001, 101, 3793-3818.
McCabe, R. W. et al., "An Investigation of the Acyl-Binding Site of Candida Antarctica Lipase B", Enzyme. Microb. Tech., 2004, 35, 393-398.
Sharma, A. K. et al., "Biocatalytic Synthesis and Characterization of Copolymers Based on Poly(Ethylene Glycol) and Unsaturated Methyl Esters", J. Macromol. Sci. Pure., 2005, 42, 1515-1521.
Wang, Z-L. et al., "Lipase-Catalyzed Polyester Synthesis", J.M.S. Pure Appl. Chem., 1996, A33(5), 599-612.
Frampton, M. B. et al., "Synthesis of Polyesters Containing Disiloxane Subunits: Structural Characterization, Kinetics, and an Examination of the Thermal Tolerance of Novozym-435", J. Mol. Catal. B-Enzym., 2013, 85-86, 149-155.
Ottosson, J. et al, "Influence of Acyl Chain Length on the Enantioselectivity of Candida Antarctica Lipase B and its Themodynamic Components in Kinetic Resolution of sec-alcohols", J. Mol. Catal. B-Enzym., 2001, 11, 1025-1028.
Liu, C. et al,. "Chain Growth and Branch Structure Formation during Lipase-Catalyzed Synthesis of Aliphatic Polycarbonate Polyols", Macromolecules, 2011, 44, 1471-1479.
Jiang, Z. et al., "Controlled Lipase-Catalyzed Synthesis of Poly(hexamethylene carbonate)", Macromolecules 2007, 40, 7934-7943.
Zini, E. et al,. "Aliphatic Polyester Carbonate Copolymers: Enzymatic Synthesis and Solid-State Characterization", Macromolecules., 2008, 41, 4681-4687.
Poojari, Y. et al., "Lipase-Catalyzed Synthesis and Properties of Silicone Aromatic Polyesters and Silicone Aromatic Polyamides", Macromolecules., 2010, 43, 4616-4622.

(Continued)

*Primary Examiner* — Kuo-Liang Peng
(74) *Attorney, Agent, or Firm* — Bereskin & Parr LLP/S.E.N.C.R.L., s.r.l.; Patricia Folkins

(57) ABSTRACT

The present application discloses siloxane-containing hybrid materials. For example, the present application discloses siloxane-containing hybrid materials comprising cyclic siloxanes or polyhedral siloxanes such as polymeric siloxane-containing hybrid materials comprising cyclic siloxanes or polyhedral siloxanes, methods for preparing such siloxane-containing hybrid materials, the use of such siloxane-containing hybrid materials for coating a substrate, coatings comprising the polymeric siloxane-containing hybrid materials, composites comprising a film of the polymeric siloxane-containing material coated on a substrate and compounds which are useful in preparing the siloxane-containing hybrid materials.

27 Claims, 12 Drawing Sheets

(56) References Cited

OTHER PUBLICATIONS

Bain, A. D., et al, "Analysis of the NMR Spectra of Some Dimethylsilanes", Magn. Reson. Chem., 2000, 38, 894-895.

Frampton, M. B. et al., "Organosilicon Biotechnolgy", Silicon., 2009, 1, 147-163.

Uppenberg, J. et al, "The Sequence, Crystal Structure Determination and Refinement of Two Crystal Forms of Lipase B from Candida Antarctica", Structure., 1994, 2, 293-308.

Numata, K. et al, "Branched Poly(lactide) Synthesized by Enzymatic Polymerization: Effects of Molecular Branches and Stereochemistry on Enzymatic Degradation and Alkaline Hydrolysis", Biomacromolecules., 2007, 8, 3115-3125.

Naik, S. et al,. "Lipases for Use in Industrial Biocatalysis: Specificity of Selected Structural Groups of Lipases", J. Mol. Catal. B-Enzym., 2010, 65, 18-23.

Jiang, Z. et al., "Lipase-Catalyzed Synthesis of Aliphatic Poly(carbonate-co-esters)", Macromolecules., 2008, 41, 4671-4680.

Asuncion, M. Z. et al., "Silsesquioxane Barrier Materials", Macromolecules., 2007, 40, 555-562.

Sellinger, A. et al., "Heck Coupling of Haloaromatics with Octavinylsilsesquioxane: Solution Processable Nanocomposites for Application in Electroluminescent Devices", Chem. Commun., 2005, 3700-3702.

Sulaiman, S. et al., "Molecules with Perfect Cubic Symmetry as Nanobuilding Blocks for 3-D Assemblies. Elaboration of Octavinylsilsesquioxane. Unusual Luminescence Shifts May Indicate Extended Conjugation Involving the Silsesquioxane Core", Chem. Mater., 2008, 20, 5563-5573.

Hinklin, T. R. et al., "Transparent, Polycrystalline Upconverting Nanoceramics: Towards 3-D Displays", Adv. Mater., 2008, 20, 1270-1273.

Roll, M. F. et al., "Nano Building Blocks via Iodination of [PhSiO1.5]n, Forming [p-I-C6H4SiO1.5]n (n=8, 10, 12), and a New Route to High-Surface-Area, Thermally Stable, Microporous Materials via Thermal Elimination of I2", J. Am. Chem. Soc., 2010, 132, 10171-10183.

Roll, M. F. et al., "Crystalline Hybrid Polyphenylene Macromolecules from Octaalkynylsilsesquioxanes, Crystal Structures, and a Potential Route to 3-D Graphenes", Macromolecules., 2011, 44, 3425-3435.

Jung, J. H. et al., "Beads on a Chain (BOC) Polymers Formed from the Reaction of [NH2PhSiO1.5]X[PhSiO1.5]10−x and [NH2PhSiO1.5]X[PhSiO1.5]12−x Mixtures (x=2-4) with the Diglycidyl Ether of Bisphenol A", Macromolecules., 2011, 44, 7263-7272.

Jung, J. H. et al., "3-D Molecular Mixtures of Catalytically Functionalized [vinylSiO1.5]10 / [vinylSiO1.5]12. Photophysical Characterization of Second Generation Derivatives", Chem. Mater., 2012, 24, 1883-1895.

\* cited by examiner

ABcyc
1082 m/z

AB₂cyc²
1163 m/z

AB₂cyc
1196 m/z

US 9,481,766 B2

SILOXANE-CONTAINING HYBRID MATERIALS

RELATED APPLICATIONS

This application claims the benefit of priority to U.S. provisional application No. 61/951,723 filed Mar. 12, 2014, the content of which is incorporated herein by reference in its entirety.

FIELD

The present application relates to siloxane-containing hybrid materials. For example, the present application relates to polymeric siloxane-containing hybrid materials comprising cyclic siloxanes or polyhedral siloxanes.

BACKGROUND

Branched polymers have different physical and chemical properties compared to their linear counterparts.[1] An understanding of these properties has made these materials useful, for example for industrial and/or medical applications. Hyperbranched polymers exhibit a fractal pattern of bonding, and typically exhibit a greater degree of polydispersity than similar dendritic and linear polymers.[2,3] Topologically speaking, hyperbranched polymers are composed of branched and terminal repeat units, along with linear units that contain unreacted functional groups. This class of materials can be initiated from a core molecule, although there are other known methods of preparing these polymers.[4,5]

Hyperbranched polymers have been produced using a variety of catalysts to control morphology and mass dispersity. For example, titanium and dialkyl tin complexes have been used in the synthesis of branched polyesters.[6-8]

Lipase catalysis was first used by Skaria et al. to generate branched polymers from ε-caprolactone and 2,2'-bis(hydroxymethyl)butanoic acid.[9] Kulshrestha et al. employed N435 (an immobilized lipase B from *Candida antarctica*) in the synthesis of glycerol-based copolyesters from adipic acid, octan-1,8-diol and glycerol under solvent-free conditions.[3] The regioselectivity for the primary alcohol of glycerol was independent of the glycerol concentration. However, the degree of branching could be varied between 9-58% by varying the feed ratio of glycerol. Triglyceride analogs derived from oleic diacid, linoleic acid and glycerol were also reported to be produced using an enzymatic method.[10]

Polysiloxanes are a useful class of polymer owing to the alternating arrangement of silicon and oxygen atoms which imparts a high degree of flexibility to the polymer backbone. Siloxane-derived materials, for example, those comprising dimethylsiloxane units, can have useful physicochemical properties, such as resistance to oxidation, low permittivity, hydrophobicity, permeability to oxygen, low glass transition temperature and/or bio-compatibility.[11-13]

Branched and cross-linked silicones can be prepared via hydrosilylation using one of several commercially available Pt[0] or Rh[1] catalysts, titanium isopropoxide and/or dibutyltin dilaurate. Alternatively, peroxide-induced free radical polymerization of acetoxy- or alkoxysilanes,[14] photo-initiated polymerization,[15] anionic polymerization[16] and tris(pentafluoroborane) catalysis[17-19] have been used to prepare a diverse range of siloxane architectures.

Enzymatic catalysis has been employed to produce polymers containing siloxane-derived fragments.[20-29] In studies where both monomers were siloxane-derived, a degree of thermal protection was conferred to the enzyme catalyst.[29] A study of the chain length selectivity of *Candida antarctica* lipase B (CalB) for trisiloxane-containing esters reported the role that steric interactions play in choosing appropriate siloxane substrates when using an enzyme catalyst.[30]

Nanostructured siloxane materials are gaining popularity due the prospect of tailoring the spatial arrangement of functional groups in space and/or their use as precursors to stereoregular silsesquioxanes.[31,32] However, to date, there are no known examples in the literature where biocatalysis or enzymatic catalysis has been employed to produce, or modify, oligocyclosiloxanes.

Spherosilicates are oligomeric silsesquioxanes derived from a $Q_8$ core, composed of eight $SiO_4$ units arranged in a cubic framework, rather than the more commonplace $T_8$ framework in which the vertices of the cubic structure are functionalized with an organic moiety.

Spherosilicates have received attention as candidates for novel functionalized materials,[33,34] encapsulants,[35,36] and bioconjugation scaffolds[37] and have been reviewed in the literature.[38-40]

Spherosilicates can be modified with various functional groups, typically incorporated via hydrosilylation chemistry, allowing for the generation of new materials with tunable properties. For example, Jutzi et al. synthesized spherosilicates functionalized with decacarborane cages, ferrocene units and half-sandwich manganese carbonyl complexes.[41] Alkyl chains, acrylates, esters, amines/amides, aryl ring systems, nitriles and alkoxysilyl groups have also been tethered to the $Q_8$ core. Tethering acrylates to the eight vertices of the cube allows for cross-linking via atom transfer radical polymerization (ATRP). Another route examined by Costa et al. tethered 2-bromo-2-methylpropionyl bromide to a hydroxypropyldimethylsiloxy-functionalized $Q_8$ cube to give an α-bromide ester suitable as an initiator for ATRP chemistry with methyl methacrylate.[42]

Polymers, coatings and 3D stars comprising polyhedral silsesquioxanes have been reported. For example, Jung and Laine have reported "beads on a chain" polymers formed from the reaction of di- and triaminophenyl, phenyl silsesquioxane with the diglycidyl ether of bisphenol A to form a soluble epoxy resin.[43] U.S. Pat. No. 7,868,198 discloses coatings incorporating multi-functional silsesquioxanes. Sulaiman et al. have reported 3-D stars with a silsesquioxane core which are disclosed to be useful for the synthesis of dendrimers or hyperbranched molecules.[44] Asuncion and Laine have reported the reaction of octaaminophenylsilsesquioxane with epoxides and dianhydrides and their subsequent heat treatment to form nanocomposite films.[45]

While many approaches have been reported for modifying the vertices of $Q_8$ and $T_8$ cubic octamers, to date an enzymatic approach has not been reported.

SUMMARY

Branched siloxane polyesters that are based on a cyclotetrasiloxane architectural scaffold have been prepared in the studies of the present application. The synthesis of octakis (methyl-9-carboxynonyl)-dimethylsiloxy-functionalized spherosilicate cubes and their subsequent enzymatic modification to produce oligoester-modified spherosilicates has also been carried out.

Accordingly, the present application includes a method for preparing a siloxane-containing hybrid material, comprising reacting a siloxane functionalized with at least one ester or carboxylic acid group with an organic nucleophile having at least one hydroxy or amine group in the presence of a lipase catalyst, wherein the siloxane comprises a cyclic siloxane or a polyhedral siloxane.

In an embodiment, the siloxane comprises a cyclic siloxane. In another embodiment, the siloxane comprises a polyhedral siloxane. In a further embodiment, the lipase catalyst is immobilized lipase B from *Candida antarctica*.

The present application also includes a polymeric siloxane-containing hybrid material prepared by a method of the present application.

The present application also includes a polymeric siloxane-containing hybrid material comprising siloxane moieties selected from cyclic siloxanes and polyhedral siloxanes that are linked intermolecularly or intramolecularly via an organic linker of Formula IV:

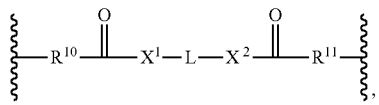

IV wherein when the siloxane moieties are cyclic siloxanes, $R^{10}$ and $R^{11}$ are each independently an alkylene, alkenylene or alkynylene group having at least four carbon atoms, for example, $C_{4-40}$alkylene, $C_{4-40}$alkenylene or $C_{4-40}$alkynylene;

when the siloxane moieties are polyhedral siloxanes, $R^{10}$ and $R^{11}$ are each independently an alkylene, alkenylene or alkynylene group having at least eight carbon atoms, for example, $C_{8-40}$alkylene, $C_{8-40}$alkenylene or $C_{8-40}$alkynylene;

$X^1$ and $X^2$ are each independently $NR^{12}$ or O;

$R^{12}$ is H or $C_{1-6}$alkyl; and

L is an alkylene, alkenylene or alkynylene group having at least six carbon atoms, for example, $C_{6-40}$alkylene, $C_{6-40}$alkenylene or $C_{6-40}$alkynylene.

The present application also includes a coating comprising the polymeric siloxane-containing hybrid material of the present application, a use of the polymeric siloxane-containing hybrid material of the present application for coating a substrate and a composite comprising a film of the polymeric siloxane-containing hybrid material of the present application coated on a substrate.

The present application also includes a compound of Formula I(b):

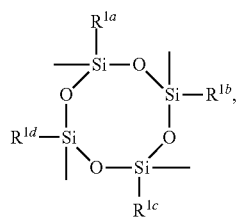

I(b)

wherein $R^{1a}$, $R^{1b}$, $R^{1c}$ and $R^{1d}$ are each individually a group of the formula:

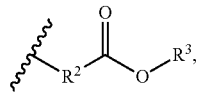

wherein $R^2$ is alkylene, alkenylene or alkynylene, for example, $C_{1-40}$alkylene, $C_{3-40}$alkenylene or $C_{3-40}$alkynylene; and
$R^3$ is H or $C_{1-6}$alkyl.

The present application also includes a compound of Formula II(b):

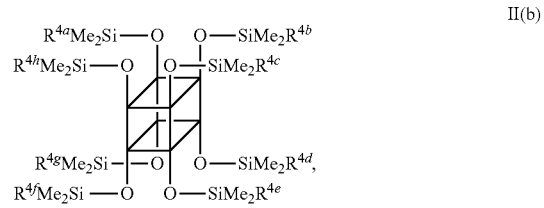

II(b)

wherein

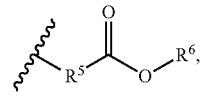

and $R^{4a}$, $R^{4b}$, $R^{4c}$, $R^{4d}$, $R^{4e}$, $R^{4f}$, $R^{4g}$ and $R^{4h}$ are each individually a group of the formula:

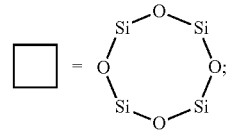

wherein $R^5$ is alkylene, alkenylene or alkynylene, for example, $C_{1-40}$alkylene, $C_{3-40}$alkenylene or $C_{3-40}$alkynylene; and $R^6$ is H or $C_{1-6}$alkyl.

Other features and advantages of the present application will become apparent from the following detailed description. It should be understood, however, that the detailed description and the specific examples while indicating embodiments of the application are given by way of illustration only, since various changes and modifications within the spirit and scope of the application will become apparent to those skilled in the art from this detailed description.

BRIEF DESCRIPTION OF THE DRAWINGS

The present disclosure will now be described in greater detail with reference to the drawings, in which.

DETAILED DESCRIPTION

I. Definitions

Figure 1:
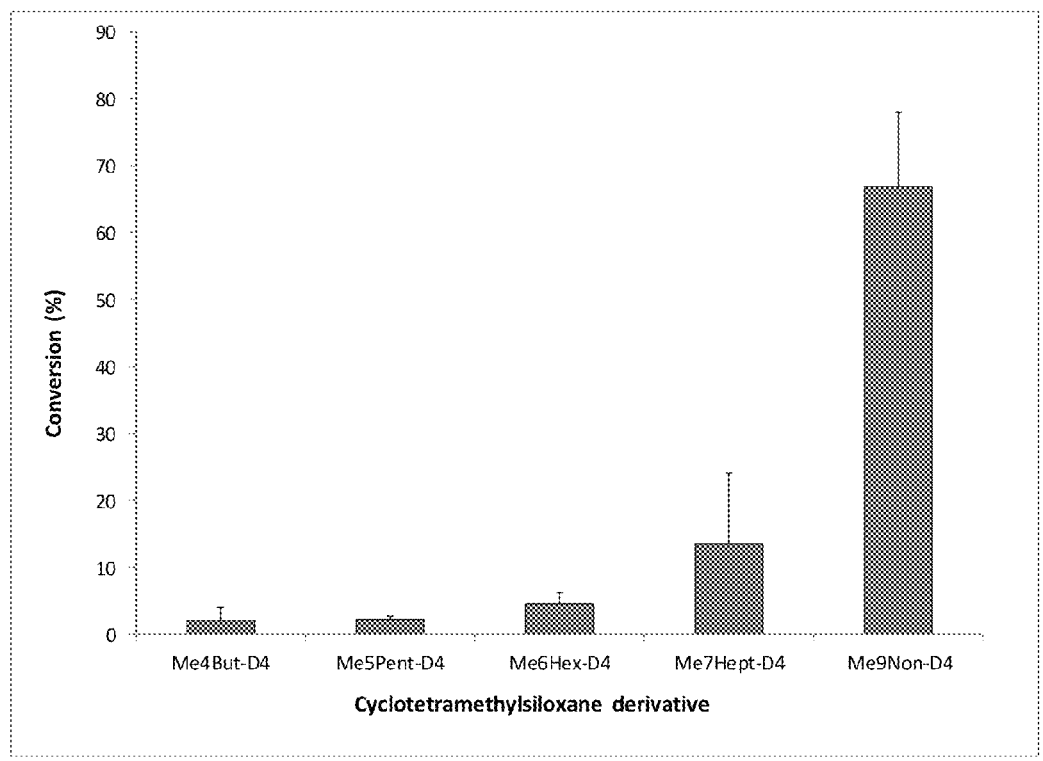
FIG. 1 shows the reaction of methyl esters of cyclotetrasiloxanes with octan-1-ol in the presence of immobilized lipase B from *Candida antarctica* (N435) wherein "Me4But-D4" refers to the compound of Formula I(a) wherein $R^{1a}$, $R^{1b}$, $R^{1c}$ and $R^{1d}$ are each $(CH_2)_4C(O)OCH_3$; "Me5Pent-D4" refers to refers to the compound of Formula I(a) wherein $R^{1a}$, $R^{1b}$, $R^{1c}$ and $R^{1d}$ are each $(CH_2)_5C(O)OCH_3$; "Me6Hex-D4" refers to refers to the compound of Formula I(a) wherein $R^{1a}$, $R^{1b}$, $R^{1c}$ and $R^{1d}$ are each $(CH_2)_6C(O)OCH_3$; "Me7Hept-D4" refers to refers to the compound of Formula I(a) wherein $R^{1a}$, $R^{1b}$, $R^{1c}$ and $R^{1d}$ are each $(CH_2)_7C(O)OCH_3$; and "Me9Non-D4" refers to the compound of Formula I(a) wherein $R^{1a}$, $R^{1b}$, $R^{1c}$ and $R^{1d}$ are each $(CH_2)_9C(O)OCH_3$.

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The expression "proceed to a sufficient extent" as used herein with reference to the reactions or method steps disclosed herein means that the reactions or method steps proceed to an extent that conversion of the starting material or substrate to product is maximized. Conversion may be maximized when greater than about 5, 10, 15, 20, 25, 30, 35, 40, 45, 50, 55, 60, 65, 70, 75, 80, 85, 90, 95 or 100% of the starting material or substrate is converted to product.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a compound" should be understood to present certain aspects with one compound or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

In embodiments of the present application, the compounds described herein have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having alternate stereochemistry. It is intended that any optical isomers, as separated, pure or partially purified optical isomers or racemic mixtures thereof are included within the scope of the present application.

The term "alkyl" as used herein, whether it is used alone or as part of another group, means straight or branched chain, saturated alkyl groups. The number of carbon atoms that are possible in the referenced alkyl group are indicated by the numerical prefix "$C_{n1-n2}$". For example, the term $C_{1-6}$alkyl means an alkyl group having 1, 2, 3, 4, 5 or 6 carbon atoms.

The term "alkenyl" as used herein, whether it is used alone or as part of another group, means straight or branched chain, unsaturated alkenyl groups. The number of carbon atoms that are possible in the referenced alkenyl group are indicated by the numerical prefix "$C_{n1-n2}$". For example, the term $C_{6-20}$alkenyl means an alkenyl group having 6, 7, 8, 9, 10, 11, 12, 13, 14, 15, 16, 17, 18, 19 or 20 carbon atoms and at least one double bond, for example 1-3, 1-2 or 1 double bond.

The term "alkynyl" as used herein, whether it is used alone or as part of another group, means straight or branched chain, unsaturated alkynyl groups. The number of carbon atoms that are possible in the referenced alkynyl group are indicated by the numerical prefix "$C_{n1-n2}$". For example, the term $C_{6-20}$alkynyl means an alkynyl group having 6, 7, 8, 9, 10, 11, 12, 13, 14, 15, 16, 17, 18, 19 or 20 carbon atoms and at least one triple bond, for example 1-3, 1-2 or 1 triple bond.

The term "alkylene" as used herein, whether it is used alone or as part of another group, means straight or branched chain, saturated alkylene group; that is a saturated carbon chain that contains substituents on two of its ends. The number of carbon atoms that are possible in the referenced alkylene group are indicated by the numerical prefix "$C_{n1-n2}$". For example, the term $C_{4-20}$alkylene means an alkylene group having 4, 5, 6, 7, 8, 9, 10, 11, 12, 13, 14, 15, 16, 17, 18, 19 or 20 carbon atoms.

The term "alkenylene" as used herein, whether it is used alone or as part of another group, means straight or branched chain, unsaturated alkenylene group; that is an unsaturated carbon chain that contains substituents on two of its ends. The number of carbon atoms that are possible in the referenced alkenylene group are indicated by the numerical prefix "$C_{n1-n2}$". For example, the term $C_{4-20}$alkenylene means an alkenylene group having 4, 5, 6, 7, 8, 9, 10, 11, 12, 13, 14, 15, 16, 17, 18, 19 or 20 carbon atoms and at least one double bond, for example 1-3, 1-2 or 1 double bond.

The term "alkynylene" as used herein, whether it is used alone or as part of another group, means straight or branched chain, unsaturated alkynylene group; that is an unsaturated carbon chain that contains substituents on two of its ends. The number of carbon atoms that are possible in the referenced alkynylene group are indicated by the numerical prefix "$C_{n1-n2}$". For example, the term $C_{4-20}$alkynylene means an alkynylene group having 4, 5, 6, 7, 8, 9, 10, 11, 12, 13, 14, 15, 16, 17, 18, 19 or 20 carbon atoms and at least one triple bond, for example 1-3, 1-2 or 1 triple bond.

The term "organic nucleophile" as used herein, refers to a hydrocarbon-based compound that comprises at least one nucleophilic group. It is to be understood that the hydrocarbon-based compound comprises, in addition to carbon and hydrogen, other atoms and functional groupings, so long as those atoms and functional groupings do not substantially interfere with the method or process being performed.

The term "nucleophile" as used herein, refers to a chemical species that donates an electron pair to an electrophile to form a chemical bond in a reaction.

The term "hybrid" as used herein refers to a material that comprises at least two distinct portions, each portion representing a different chemical class of compound. For example, the hybrid materials of the present application comprise a siloxane portion and an organic-compound containing portion.

The term "amine group" as used herein, refers to a functional group of the formula:

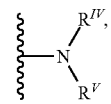

wherein

denotes the site of attachment to a carbon atom in the organic nucleophile and $R^{IV}$ and $R^{V}$ are each independently H or an organic group such as an alkyl, alkenyl, alkynyl or aryl group. In an embodiment, the amine group is —$NH_2$.

The term "aryl" as used herein, whether it is used alone or as part of another group, refers to cyclic groups that contain at least one aromatic ring. In an embodiment of the present application, the aryl group contains 6, 9, 10 or 14 carbon atoms, such as phenyl, naphthyl, indanyl or anthracenyl.

The term "lipase catalyst" as used herein refers to a lipase (i.e. an enzyme which can catalyze the hydrolysis of triacylglycerols into glycerol and free fatty acids) which has an active site that can bind a siloxane-containing substrate. In an embodiment, the lipase is lipase B from *Candida antarctica*.

The term "immobilized" as used herein in reference to a lipase catalyst means that the lipase catalyst is immobilized, for example by covalent attachment, to a support which is substantially inert under the conditions used in the methods of the present application. In an embodiment, the support is an acrylic resin. Methods for immobilizing lipase catalysts such as lipase B from *Candida antarctica* on a support are known and the selection of a suitable method for the preparation of the desired immobilized lipase catalyst can be made by a person skilled in the art. Immobilized lipase catalysts such as immobilized lipase B from *Candida antarctica* are also available from commercial sources such as Sigma-Aldrich™.

The term "polymer" as used herein, for example, in reference to a polymeric siloxane-containing hybrid material includes linear oligomers of any chain length and cyclic oligomers of any ring size. Cyclic oligomers having any ring size may also be known as "macrocycles" or "macrocyclic oligomer".

The term "siloxane" as used herein refers to an organosilicon compound which comprises Si—O—Si linkages.

The term "cyclic siloxane" as used herein refers to an organosilicon compound comprising a suitable cyclic moiety of the structure [—Si—OH]$_n$.

The term "polyhedral siloxane" as used herein refers to a siloxane which has a three dimensional or "cage" structure. A number of polyhedral siloxanes are known in the art such as $T_m$ cages, wherein m is 6, 8, 10 or 12 as well as $Q_8$ cages.

The term "$T_m$" as used herein in reference to a polyhedral siloxane refers to a compound having a cage structure of the general formula (R'SiO$_{1.5}$)$_m$, wherein each R' is independently a hydrogen or an organic group. In an embodiment, the $T_m$ cage is a $T_8$ cage of the general formula $(R'SiO_{1.5})_8$.

The term "$Q_8$" or "$Q_8$ silsesquioxane" as used herein in reference to a polyhedral siloxane refers to a compound having a cage structure of the general formula:

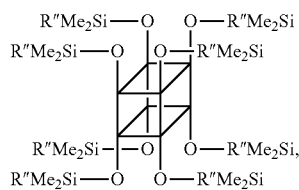

wherein each R" is independently a hydrogen or an organic group; and

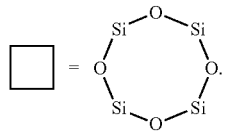

The term "$D_4$" as used herein in reference to a siloxane refers to a compound having a cyclic structure of the general formula $[R'''(CH_3)SiO]_4$, wherein each R''' is independently a hydrogen or an organic group.

II. Methods

Branched siloxane polyesters that are based on a cyclotetrasiloxane architectural scaffold have been prepared in the studies of the present application. The new polymers were characterized by nuclear magnetic resonance spectroscopy and matrix assisted laser desorption ionization time of flight mass spectrometry (MALDI-ToF MS). The synthesis of octakis(methyl-9-carboxynonyl)-dimethylsiloxy-functionalized spherosilicate cubes and their subsequent enzymatic modification to produce oligoester-modified spherosilicates has also been carried out in the studies of the present application.

Accordingly, the present application includes a method for preparing a siloxane-containing hybrid material, comprising reacting a siloxane functionalized with at least one ester or carboxylic acid group with an organic nucleophile having at least one hydroxy or amine group in the presence of a lipase catalyst, wherein the siloxane comprises a cyclic siloxane or a polyhedral siloxane.

In an embodiment, the siloxane comprises a cyclic siloxane. The ring size of the cyclic siloxane can vary and the selection of a suitable cyclic siloxane can be made by a person skilled in the art. In an embodiment, the siloxane comprises a cyclotrisiloxane, a cyclotetrasiloxane, a cyclopentasiloxane or a cyclohexasiloxane. It will be appreciated by a person skilled in the art that the silicon atoms in the siloxane ring can have up to two organic substituents and therefore the silicon atom can be functionalized with an ester or carboxylic acid group and also another suitable organic substituent. Accordingly, in another embodiment, the siloxane comprises a 1,3,5-tri($C_{1-6}$alkyl)cyclotrisiloxane, a 1,3,5,7-tetra($C_{1-6}$alkyl)cyclotetrasiloxane, a 1,3,5,7,9-penta($C_{1-6}$alkyl)cyclopentasiloxane or a 1,3,5,7,9,11-hexa($C_{1-6}$alkyl)cyclohexasiloxane, wherein the silicon atoms of the respective cyclic siloxanes are each optionally further substituted by the at least one ester or carboxylic acid group. In a further embodiment of the present application, each of the silicon atoms of the respective cyclic siloxanes is further substituted by one of the at least one ester or carboxylic acid group. In another embodiment, the siloxane comprises a 1,3,5-trimethylcyclotrisiloxane, a 1,3,5,7-tetramethylcyclotetrasiloxane, a 1,3,5,7,9-pentamethylcyclopentasiloxane or a 1,3,5,7,9,11-hexamethylcyclohexasiloxane wherein the silicon atoms of the respective methylcyclosiloxanes are each optionally further substituted by the at least one ester or carboxylic acid group. In a further embodiment of the present application, each of the silicon atoms of the respective methylcyclosiloxanes is further substituted by one of the at least one ester or carboxylic acid group.

In another embodiment, the siloxane functionalized with at least one ester or carboxylic acid group is a compound of Formula I(a):

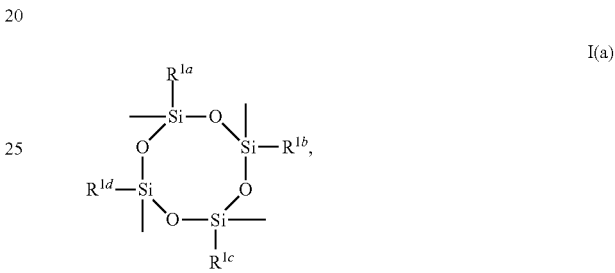

wherein $R^{1a}$, $R^{1b}$, $R^{1c}$ and $R^{1d}$ are each individually a group of the formula:

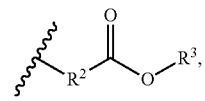

wherein $R^2$ is an alkylene, alkenylene or alkynylene group having at least four carbon atoms; and $R^3$ is H or $C_{1-6}$alkyl.

It will be appreciated that the alkylene, alkenylene and alkynylene groups can conceivably comprise any number of carbon atoms equal to or greater than four. It is an embodiment that $R^2$ is $C_{4-40}$alkylene, $C_{4-40}$alkenylene or $C_{4-40}$alkynylene. In another embodiment, $R^2$ is $C_{4-20}$alkylene, $C_{4-20}$alkenylene or $C_{4-20}$alkynylene. In a further embodiment, $R^2$ is $C_{8-16}$alkylene, $C_{8-16}$alkenylene or $C_{8-16}$alkynylene. It is an embodiment that $R^2$ is $C_{8-16}$alkylene. In another embodiment, $R^2$ is $C_{8-12}$alkylene. In a further embodiment, $R^2$ is —$(CH_2)_9$—.

In an embodiment, $R^3$ is H. In another embodiment, $R^3$ is $C_{1-6}$alkyl. In a further embodiment, $R^3$ is $C_{1-4}$alkyl. It is an embodiment that $R^3$ is $CH_3$.

In another embodiment of the present application, $R^{1a}$, $R^{1b}$, $R^{1c}$ and $R^{1d}$ are each $(CH_2)_9C(O)OCH_3$.

In an embodiment, the siloxane comprises a polyhedral siloxane. In another embodiment, the siloxane comprises a $Q_8$ silsesquioxane.

In an embodiment, the siloxane functionalized with at least one ester or carboxylic acid group is a compound of Formula II(a):

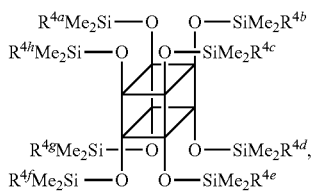

wherein

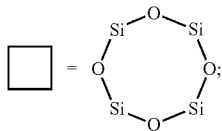

and
$R^{4a}$, $R^{4b}$, $R^{4c}$, $R^{4d}$, $R^{4e}$, $R^{4f}$, $R^{4g}$, and $R^{4h}$ are each individually a group of the formula:

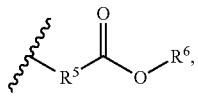

wherein
$R^5$ is an alkylene, alkenylene or alkynylene group having at least eight carbon atoms; and
$R^6$ is H or $C_{1-6}$alkyl.

It will be appreciated that the alkylene, alkenylene and alkynylene groups can conceivably comprise any number of carbon atoms equal to or greater than eight. It is an embodiment that $R^5$ is $C_{8-40}$alkylene, $C_{8-40}$alkenylene or $C_{8-40}$alkynylene. In another embodiment, $R^5$ is $C_{8-20}$alkylene, $C_{8-20}$alkenylene or $C_{8-20}$alkynylene. In a further embodiment, $R^5$ is $C_{8-16}$alkylene, $C_{8-16}$alkenylene or $C_{8-16}$alkynylene. It is an embodiment that $R^5$ is $C_{8-16}$alkylene. In another embodiment of the present application, $R^5$ is —$(CH_2)_9$—.

In an embodiment, $R^6$ is H. In another embodiment, $R^6$ is $C_{1-6}$alkyl. In a further embodiment, $R^6$ is $C_{1-4}$alkyl. It is an embodiment that $R^6$ is $CH_3$.

In another embodiment of the present application, $R^{4a}$, $R^{4b}$, $R^{4c}$, $R^{4d}$, $R^{4e}$, $R^{4f}$, $R^{4g}$ and $R^{4h}$ are each $(CH_2)_9C(O)OCH_3$.

The structure of the organic nucleophile having at least one hydroxy or amine group can vary and the selection of a suitable organic nucleophile can be made by a person skilled in the art. In an embodiment, the organic nucleophile has at least two hydroxy groups or at least two amine groups. In an embodiment, the organic nucleophile has two hydroxy groups or two amine groups. In a further embodiment, the organic nucleophile has two hydroxy groups. It is an embodiment that the organic nucleophile has two amine groups.

In another embodiment, the organic nucleophile is a compound of Formula III:

$$R^7\text{-L-}(R^8)_n \qquad \text{III,}$$

wherein
$R^7$ is OH or $NR^9H$;
n is an integer selected from 0 and 1;
when n is 0, L is an alkyl, alkenyl or alkynyl group having at least six carbon atoms;
when n is 1, is L is an alkylene, alkenylene or alkynylene group having at least six carbon atoms;
$R^8$ is OH or $NR^9H$; and
$R^9$ is H or $C_{1-6}$alkyl.

In an embodiment, $R^7$ is OH. In another embodiment, $R^7$ is $NR^9H$.

In an embodiment, $R^8$ is OH. In another embodiment, $R^8$ is $NR^9H$.

In an embodiment $R^7$ and $R^8$ are each OH. In another embodiment, $R^7$ and $R^8$ are each $NR^9H$. In a further embodiment, $R^7$ and $R^8$ are each $NH_2$.

It will be appreciated that the alkyl, alkenyl and alkynyl groups can conceivably comprise any number of carbon atoms equal to or greater than six. It is an embodiment that n is 0 and L is $C_{6-40}$alkyl, $C_{6-40}$alkenyl or $C_{6-40}$alkynyl. In another embodiment, n is 0 and L is $C_{6-20}$alkyl, $C_{6-20}$alkenyl or $C_{6-20}$alkynyl. In a further embodiment, n is 0 and L is $C_{6-14}$alkyl, $C_{6-14}$alkenyl or $C_{6-14}$alkynyl. It is an embodiment that n is 0 and L is $C_{6-12}$alkyl, $C_{6-12}$alkenyl or $C_{6-12}$alkynyl. In another embodiment, n is 0 and L is $C_{6-12}$alkyl. In a further embodiment of the present application, n is 0 and L is —$(CH_2)_7CH_3$.

It will be appreciated that the alkylene, alkenylene and alkynylene groups can conceivably comprise any number of carbon atoms equal to or greater than six. It is an embodiment that n is 1 and L is $C_{6-40}$alkylene, $C_{6-40}$alkenylene or $C_{6-40}$alkynylene. In another embodiment, n is 1 and L is $C_{6-20}$alkylene, $C_{6-20}$alkenylene or $C_{6-20}$alkynylene. In a further embodiment, n is 1 and L is $C_{6-14}$alkylene, $C_{6-14}$alkenylene or $C_{6-14}$alkynylene. It is an embodiment that n is 1 and L is $C_{6-12}$alkylene, $C_{6-12}$alkenylene or $C_{6-12}$alkynylene. In another embodiment of the present application, n is 1 and L is $C_{6-12}$alkylene. In a further embodiment, n is 1 and L is —$(CH_2)_8$—.

In an embodiment, $R^9$ is H. In another embodiment, $R^9$ is $C_{1-6}$alkyl. In a further embodiment, $R^9$ is $C_{1-4}$alkyl. It is an embodiment that $R^9$ is $CH_3$.

In an embodiment of the present application, the lipase catalyst is an immobilized lipase catalyst. In another embodiment, the lipase catalyst is immobilized lipase B from *Candida antarctica*.

In an embodiment, the method is carried out under solvent-free conditions. In another embodiment, the siloxane functionalized with at least one ester or carboxylic acid group is reacted with the organic nucleophile in a suitable organic solvent. It is an embodiment that the organic solvent is toluene.

It will be appreciated by a person skilled in the art that the properties of the siloxane-containing hybrid materials produced in the method such as molecular mass, dispersity and degree of cyclization will depend, for example on the amount of time the mixture is allowed to react, the presence or absence of solvent in the reaction mixture, the temperature and the amount of lipase catalyst used. The selection of suitable conditions to obtain particular siloxane-containing hybrid materials can be made by a person skilled in the art in light of their common general knowledge and with reference to the present application.

In an embodiment, the siloxane comprises a cyclic siloxane and the conditions for reacting the siloxane with the organic nucleophile in the presence of a lipase catalyst comprise adding the lipase catalyst to a mixture of the siloxane and the organic nucleophile, optionally in the presence of a suitable organic solvent and allowing the mixture to react for a time and temperature for the conversion of the siloxane and organic nucleophile to the siloxane-containing hybrid material to proceed to a sufficient extent, for example at a temperature of about 60° C. to about 130° C. or about 70° C. to about 100° C. When an organic solvent is used, a longer time is generally used. Accordingly, in an embodiment, the reaction is performed under solvent-free conditions for a time of about 60 minutes to about 168 hours or about 24 hours to about 120 hours. In another embodiment, the reaction is performed in the presence of an organic solvent for a time of about 60 minutes to about 168 hours or about 24 hours to about 120 hours.

In another embodiment, the siloxane comprises a polyhedral siloxane and the conditions for reacting the siloxane with the organic nucleophile in the presence of a lipase catalyst comprise adding the lipase catalyst to a mixture of the siloxane and the organic nucleophile in the presence of a suitable organic solvent and allowing the mixture to react for a time and temperature for the conversion of the siloxane and organic nucleophile to the siloxane-containing hybrid material to proceed to a sufficient extent, for example at a temperature of about 60° C. to about 130° C. or about 70° C. to about 100° C. for a time of about 30 minutes to about 120 hours or about 1 hour to about 120 hours.

In another embodiment, the lipase catalyst is added in an amount of from about 0.1 wt % to about 20 wt % or about 5 wt % to about 10 wt % based on the total mass of the siloxane and the organic nucleophile.

In an embodiment, the method for preparing a siloxane-containing hybrid material is operated as a batch method. In another embodiment, the method is operated as a semi-continuous method or a continuous method.

In another embodiment of the present application, the siloxane-containing hybrid material is a polymeric siloxane-containing hybrid material.

In another embodiment, the siloxane-containing hybrid material is a cyclic oligomer having any ring size (macrocyclic oligoesters of any ring size). In one embodiment, the amount of macrocyclic oligoesters which are formed is, in one aspect, dependent upon the amount of solvent used to conduct the method. In one embodiment, when a solvent (hexanes, toluene, etc) is used to conduct the method, the higher the dilution of the system results in a higher amount of macrocylic oligoesters being formed. For example, when the method is conducted at a concentration of 5-100 mM, optionally, 20-75 mM, or optionally 25-50 nM (concentration of monomers), the conversion of the siloxane monomers to macrocyclic oligoesters is at least about 50%, or about 75%, or about 90%, or about 95%.

In another embodiment, when the method is conducted in a neat solution (for example, the method being conducted in the organic nucleophile such as 1,8-octane-diol), a higher amount of the polymeric siloxane-containing hybrid material is formed.

In one embodiment, the macrocyclic oligoesters are formed from the siloxane compounds of the Formula I(a). In one embodiment, the macrocyclic oligoesters contain at least one cyclic siloxane core. For example, a macrocyclic oligoester containing one cyclic siloxane core has the structure:

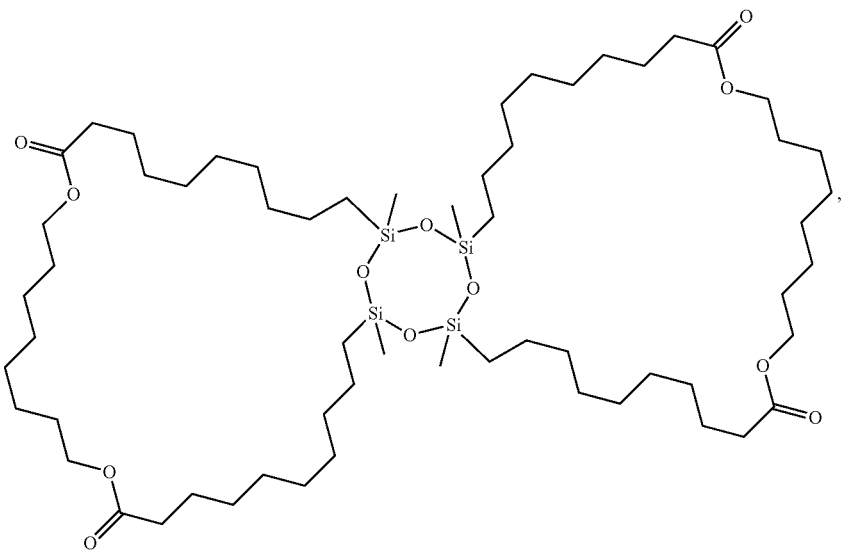 [SMILES: C[Si]12CCCCCCCCCC(=O)OCCCCCCCCOC(=O)CCCCCCCCC[Si](C)(O1)O[Si]1(C)CCCCCCCCCC(=O)OCCCCCCCCOC(=O)CCCCCCCCC[Si](C)(O1)O2]

while, in another example, a macrocylic oligoester containing two siloxane cores has the structure:

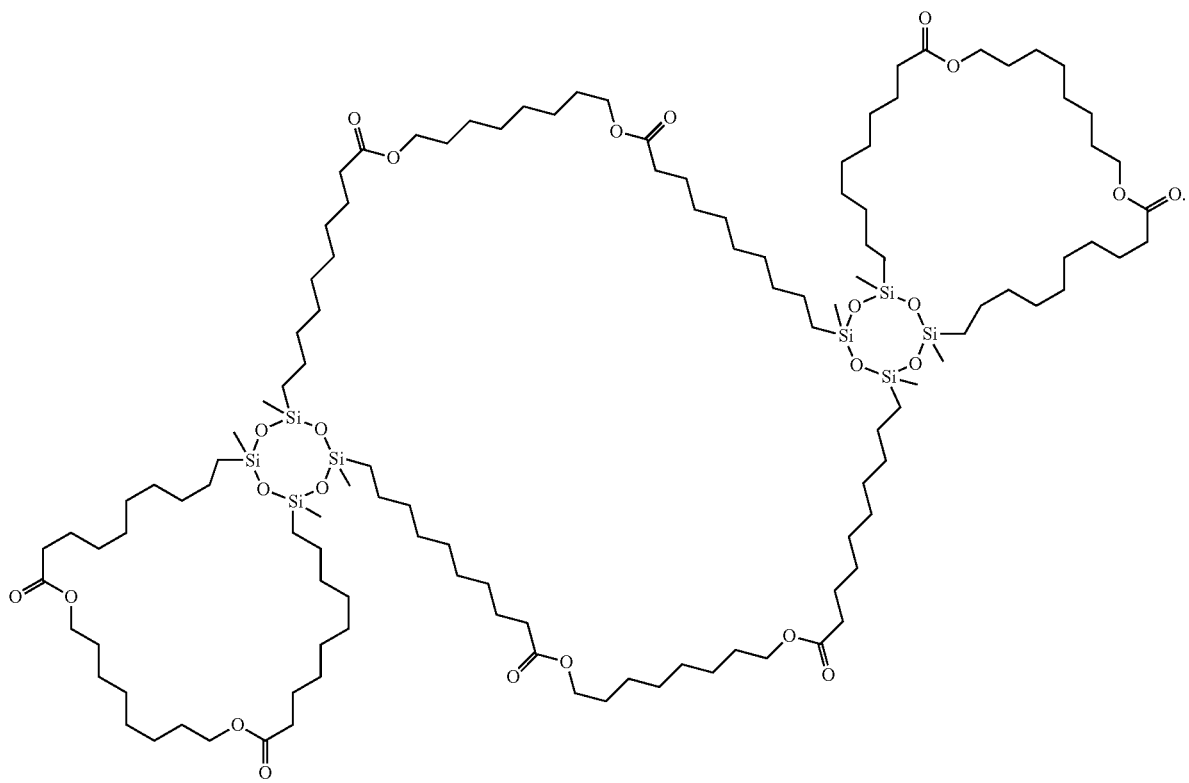 [SMILES: C[Si]12CCCCCCCCCC(=O)OCCCCCCCCOC(=O)CCCCCCCCC[Si](C)(O1)O[Si]1(C)CCCCCCCCCC(=O)OCCCCCCCCOC(=O)CCCCCCCCC[Si]3(C)O[Si]4(C)CCCCCCCCCC(=O)OCCCCCCCCOC(=O)CCCCCCCCC[Si](C)(O4)O[Si](C)(CCCCCCCCCC(=O)OCCCCCCCCOC(=O)CCCCCCCCC[Si](C)(O2)O1)O3]

Other macrocyclic oligoesters include the following, where □ represents a cyclic siloxane (such as a compound of the Formula I(a) with at least one ester or carboxylic acid group) as defined herein and ● represents an organic nucleophile as defined herein:

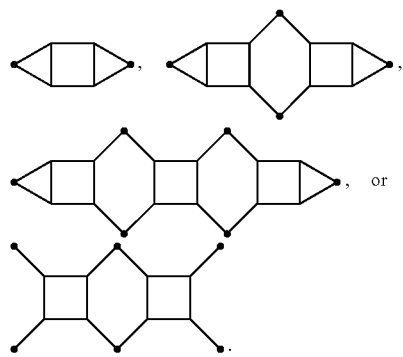

III. Siloxane-Containing Hybrid Materials

The methods of the present application were shown to be useful for preparing polymers comprising cyclotetrasiloxane or silsesquioxane moieties. In another embodiment, the methods of the present application are useful for preparing macrocyclic oligoesters.

Accordingly, the present application also includes a polymeric siloxane-containing hybrid material prepared by a method for preparing a polymeric siloxane-containing hybrid material of the present application. The present application also includes macrocyclic oligoesters as the siloxane-containing hybrid material, prepared by a method for preparing a siloxane-containing hybrid material of the present application.

The present application also includes a polymeric siloxane-containing hybrid material and/or macrocyclic oligoesters comprising siloxane moieties selected from cyclic siloxanes and polyhedral siloxanes that are linked intermolecularly or intramolecularly via an organic linker of Formula IV:

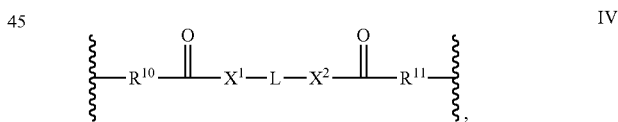

IV wherein
when the siloxane moieties comprise cyclic siloxanes, $R^{10}$ and $R^{11}$ are each independently an alkylene, alkenylene or alkynylene group having at least four carbon atoms;
when the siloxane moieties comprise polyhedral siloxanes, $R^{10}$ and $R^{11}$ are each independently an alkylene, alkenylene or alkynylene group having at least eight carbon atoms;
$X^1$ and $X^2$ are each independently $NR^{12}$ or O;
$R^{12}$ is H or $C_{1-6}$alkyl; and
L is an alkylene, alkenylene or alkynylene group having at least six carbon atoms.

In an embodiment, the siloxane moiety comprises a cyclic siloxane. In another embodiment, the siloxane moiety comprises a polyhedral siloxane. It will be appreciated by a person skilled in the art that embodiments relating to the selection of a suitable cyclic siloxane or a suitable polyhedral siloxane can be varied as discussed herein in respect of the methods for preparing a siloxane-containing hybrid material of the present application.

It will be appreciated that the alkylene, alkenylene and alkynylene groups can conceivably comprise any number of carbon atoms equal to or greater than four. It is an embodiment that the siloxane moieties comprise cyclic siloxanes and $R^{10}$ and $R^{11}$ are each independently $C_{4-40}$alkylene, $C_{4-40}$alkenylene or $C_{4-40}$alkynylene. In another embodiment, the siloxane moieties comprise cyclic siloxanes and $R^{10}$ and $R^{11}$ are each independently $C_{4-20}$alkylene, $C_{4-20}$alkenylene or $C_{4-20}$alkynylene. In a further embodiment, the siloxane moieties comprise cyclic siloxanes and $R^{10}$ and $R^{11}$ are each independently $C_{4-12}$alkylene, $C_{4-12}$alkenylene or $C_{4-12}$alkynylene. It is an embodiment that the siloxane moieties comprise cyclic siloxanes and $R^{10}$ and $R^{11}$ are each independently $C_{4-12}$alkylene. In another embodiment, the siloxane moieties comprise cyclic siloxanes and $R^{10}$ and $R^{11}$ are each independently $C_{4-9}$alkylene. In a further embodiment, the siloxane moieties comprise cyclic siloxanes and $R^{10}$ and $R^{11}$ are each —$(CH_2)_9$—.

It will be appreciated that the alkylene, alkenylene and alkynylene groups can conceivably comprise any number of carbon atoms equal to or greater than eight. It is an embodiment that the siloxane moieties comprise polyhedral siloxanes and $R^{10}$ and $R^{11}$ are each independently $C_{8-40}$alkylene, $C_{8-40}$alkenylene or $C_{8-40}$alkynylene. In another embodiment, the siloxane moieties comprise polyhedral siloxanes and $R^{10}$ and $R^{11}$ are each independently $C_{8-20}$alkylene, $C_{8-20}$alkenylene or $C_{8-20}$alkynylene. In a further embodiment, the siloxane moieties comprise polyhedral siloxanes and $R^{10}$ and $R^{11}$ are each independently $C_{8-12}$alkylene, $C_{8-12}$alkenylene or $C_{8-12}$alkynylene. It is an embodiment that the siloxane moieties comprise polyhedral siloxanes and $R^{10}$ and $R^{11}$ are each independently $C_{8-12}$alkylene. In another embodiment of the present application, the siloxane moieties comprise polyhedral siloxanes and $R^{10}$ and $R^{11}$ are each —$(CH_2)_9$—.

In an embodiment, $X^1$ and $X^2$ are each O. In another embodiment, $X^1$ and $X^2$ are each independently $NR^{12}$. In a further embodiment of the present application, $X^1$ and $X^2$ are each NH.

In an embodiment, $R^{12}$ is H. In another embodiment, $R^{12}$ is $C_{1-8}$alkyl. In a further embodiment, $R^{12}$ is $C_{1-4}$alkyl. It is an embodiment that $R^{12}$ is $CH_3$.

It will be appreciated that the alkylene, alkenylene and alkynylene groups can conceivably comprise any number of carbon atoms equal to or greater than six. It is an embodiment that L is $C_{6-40}$alkylene, $C_{6-40}$alkenylene or $C_{6-40}$alkynylene. In another embodiment, L is $C_{6-20}$alkylene, $C_{6-20}$alkenylene or $C_{6-20}$alkynylene. In a further embodiment, L is $C_{6-14}$alkylene, $C_{6-14}$alkenylene or $C_{6-14}$alkynylene. It is an embodiment that L is $C_{6-12}$alkylene, $C_{6-12}$alkenylene or $C_{6-12}$alkynylene. In another embodiment of the present application, L is $C_{6-12}$alkylene. In a further embodiment of the present application, L is —$(CH_2)_8$—.

In one embodiment, the present application includes macrocyclic oligoesters comprising cyclic siloxanes that are linked intramolecularly, or intermolecularly and intramolecularly, via an organic linker of Formula IV as defined above.

In one embodiment, the present application includes macrocyclic oligoesters of any size, for example, ☐ represents a cyclic siloxane (for example, cyclotetrasiloxane) and

represents an organic linker of the Formula IV as defined herein:

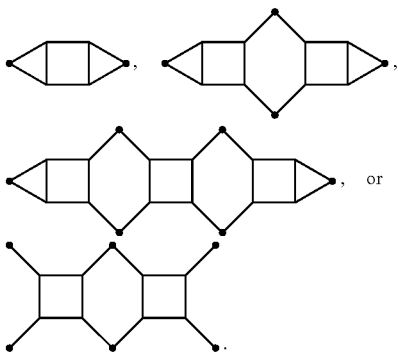

In one embodiment, when the macrocyclic oligoester comprises only one cyclic siloxane, the macrocyclic oligoester is intramolecularly linked via two organic linkers to form an oligoester such as for example

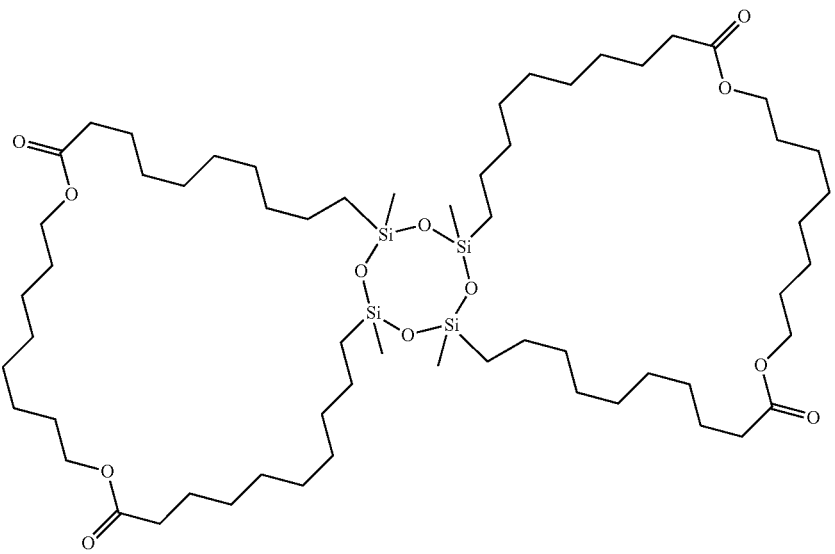

In one embodiment, when two or more cyclic siloxanes are linked intramolecularly and intermolecularly, larger macrocyclic oligoesters are formed, such as for example

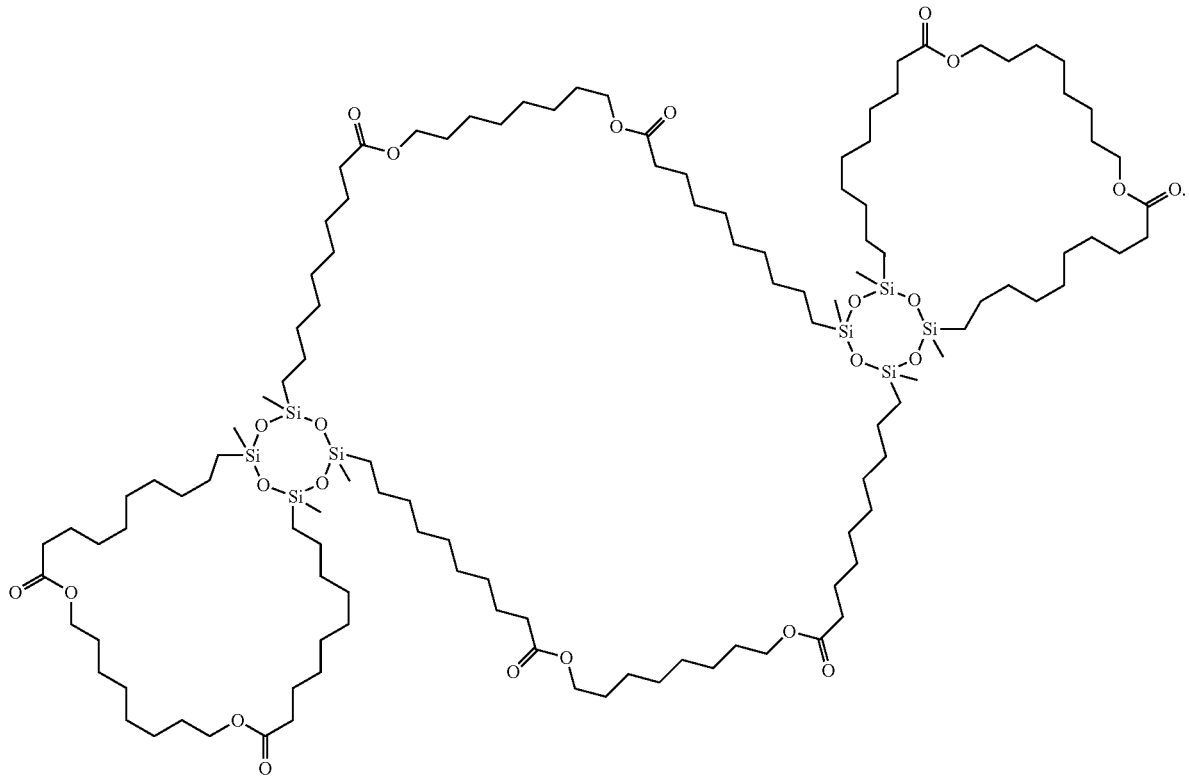 [SMILES: C[Si]12CCCCCCCCCC(=O)OCCCCCCCCOC(=O)CCCCCCCCC[Si](C)(O1)O[Si]1(C)CCCCCCCCCC(=O)OCCCCCCCCOC(=O)CCCCCCCCC[Si]3(C)O[Si]4(C)CCCCCCCCCC(=O)OCCCCCCCCOC(=O)CCCCCCCCC[Si](C)(O4)O[Si](C)(CCCCCCCCCC(=O)OCCCCCCCCOC(=O)CCCCCCCCC[Si](C)(O2)O1)O3]

IV. Coatings and Composites

Polymeric siloxane-containing hybrid materials of the present application have been coated on a substrate.

Accordingly, the present application also includes a coating comprising the polymeric siloxane-containing hybrid material of the present application, a use of the polymeric siloxane-containing hybrid material of the present application for coating a substrate as well as a composite comprising a film of the polymeric siloxane-containing hybrid material of the present application coated on a substrate.

V. Compounds

New ester-functionalized cyclotetrasiloxanes and silsesquioxanes were prepared in the studies of the present application.

Accordingly, the present application also includes compound of Formula I(b):

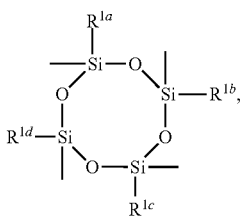

I(b)

wherein $R^{1a}$, $R^{1b}$, $R^{1c}$ and $R^{1d}$ are each individually a group of the formula:

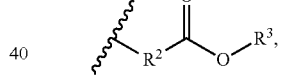

wherein $R^2$ is an alkylene, alkenylene or alkynylene group; and $R^3$ is H or $C_{1-6}$alkyl.

It will be appreciated that the alkylene, alkenylene and alkynylene groups can conceivably comprise any number of carbon atoms equal to or greater than one, three and three, respectively. It is an embodiment that $R^2$ is $C_{1-40}$alkylene, $C_{3-40}$alkenylene or $C_{3-40}$alkynylene. In another embodiment, $R^2$ is $C_{4-20}$alkylene, $C_{4-20}$alkenylene or $C_{4-20}$alkynylene. In a further embodiment, $R^2$ is $C_{4-16}$alkylene, $C_{4-16}$alkenylene or $C_{4-16}$alkynylene. It is an embodiment that $R^2$ is $C_{4-16}$alkylene. In another embodiment of the present application, $R^2$ is $C_{4-9}$alkylene. In a further embodiment, $R^2$ is —$(CH_2)_9$—.

In an embodiment, $R^3$ is H. In another embodiment, $R^3$ is $C_{1-6}$alkyl. In a further embodiment, $R^3$ is $C_{1-4}$alkyl. It is an embodiment that $R^3$ is $CH_3$.

In an embodiment, $R^{1a}$, $R^{1b}$, $R^{1c}$ and $R^{1d}$ are each $(CH_2)_4C(O)OCH_3$, $(CH_2)_5C(O)OCH_3$, $(CH_2)_6C(O)OCH_3$, $(CH_2)_7C(O)OCH_3$ or $(CH_2)_9C(O)OCH_3$. In another embodiment, $R^{1a}$, $R^{1b}$, $R^{1c}$ and $R^{1d}$ are each $(CH_2)_9C(O)OCH_3$.

The present application also includes a compound of Formula II(b):

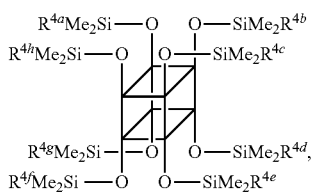

wherein

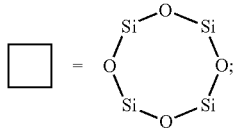

and
$R^{4a}$, $R^{4b}$, $R^{4c}$, $R^{4d}$, $R^{4e}$, $R^{4f}$, $R^{4g}$ and $R^{4h}$ are each individually a group of the formula:

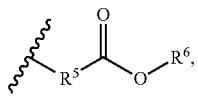

wherein
$R^5$ is an alkylene, alkenylene or alkynylene group; and
$R^6$ is H or $C_{1-6}$alkyl.

It will be appreciated that the alkylene, alkenylene and alkynylene groups can conceivably comprise any number of carbon atoms equal to or greater than one, three and three, respectively. It is an embodiment that $R^5$ is $C_{1-40}$alkylene, $C_{3-40}$alkenylene or $C_{3-40}$alkynylene. In another embodiment, $R^5$ is $C_{4-20}$alkylene, $C_{4-20}$alkenylene or $C_{4-20}$alkynylene. In a further embodiment, $R^5$ is $C_{4-16}$alkylene, $C_{4-16}$alkenylene or $C_{4-16}$alkynylene. It is an embodiment that $R^5$ is $C_{4-16}$alkylene. In another embodiment of the present application $R^5$ is —$(CH_2)_9$—.

In an embodiment, $R^6$ is H. In another embodiment, $R^6$ is $C_{1-6}$alkyl. In a further embodiment, $R^6$ is $C_{1-4}$alkyl. It is an embodiment that $R^6$ is $CH_3$.

In another embodiment of the present application, $R^{4a}$, $R^{4b}$, $R^{4c}$, $R^{4d}$, $R^{4e}$, $R^{4f}$, $R^{4g}$, and $R^{4h}$ are each $(CH_2)_9C(O)OCH_3$.

The following non-limiting examples are illustrative of the present application:

EXAMPLES

Example 1

Synthesis and Characterization of Tetracyclosiloxane Frameworks for the Chemoenzymatic Synthesis of Polymers The lipase-mediated synthesis of hyperbranched polyesters derived from a cyclotetrasiloxane framework is disclosed in the present studies. A model for how the early stages of this polymerization reaction occurs under solvent-free conditions has been proposed. A macrocyclic oligoester based on the same cyclotetrasiloxane framework has been produced and isolated.

I. Materials and Instrumentation

Materials 1,3,5,7-tetramethylcyclotetrasiloxane, Karstedt's platinum catalyst complex 2% in xylenes ($Pt^0(dvs)$), immobilized lipase B from *Candida antarctica* (sometimes referred to herein as Novozyme 435 or N435), methyl 4-pentenoate, methyl 5-hexenoate, methyl 6-heptenoate, 7-octenoic acid and 9-decenoic acid were obtained from Sigma-Aldrich (Oakville, Ontario, Canada). Octan-1-ol was obtained from Alpha Aesar (Ward Hill, N.J., USA). All other solvents were of a suitable grade and were stored over 4 Å molecular sieves. 7-methyl octenoate and 9-methyl decenoate were prepared in accordance with a literature procedure.[46]

Instrumentation

NMR spectra ($^1H$, $^{13}C$, $^{29}Si$, COSY, HSQC, HMBC) were recorded on a Bruker™ Avance AV-300 nuclear magnetic resonance spectrometer equipped with a BB-PABBO probe. $^1H$ and $^{13}C$ spectra were referenced to the residual protons of $CHCl_3$ in $CDCl_3$ and $^{29}Si$ spectra were referenced to tetramethylsilane (TMS). Fourier-transform infrared spectra (FTIR) were obtained using a Mattson Research Series infrared spectrometer operating in transmission mode. Samples were prepared as thin films on KBr plates. Each spectrum was carried out using 32 scans at 2 $cm^{-1}$ resolution. Electrospray ionization mass spectrometry (EI-MS) was carried out using a Kratos Concept 1S High Resolution E/B mass spectrometer in negative ion mode. MALDI-ToF MS spectra were acquired on a Bruker Autoflex MALDI-ToF mass spectrometer in the positive ion mode. Samples were dissolved into HPLC grade THF or acetone, sonicated, combined with an NaCl/THF (acetone) mixture and sonicated a second time. A small sample was transferred to a stainless steel plate that was preloaded with a paste composed of dithranol/THF.

Matrix Assisted Laser Desorption Ionization Time of Flight Mass Spectrometry

Matrix assisted laser desorption ionization time of flight mass spectrometry (MALDI-ToF MS) is useful for studying the component ions within a mixture. Several systems derived from siloxanes[47-49] and silsesquioxanes[59-53] have previously been studied using MALDI-ToF MS. The similarity between oligocyclosiloxanes and their larger counterpart silsesquioxanes permits the use of this approach to aid in the identification of the individual components of the final reaction mixture as well as to determine the number average molecular mass ($M_n$), the weight average molecular mass ($M_w$), and the polydispersity ($M_w/M_n$) of the polymer mixture. Further MALDI-ToF MS analysis can be used, for example to shed light on the evolution of the final polymer by analyzing the polyesterification reaction at predetermined time points.

II. Reactions

Preparation of the Compound of Formula I(a)
Wherein $R^{1a}$, $R^{1b}$, $R^{1c}$ and $R^{1d}$ are Each $(CH_2)_4C(O)OCH_3$ (1,3,5,7-tetrakis(4-carboxybutyl)-1,3,5,7-tetramethylcyclotetrasiloxane tetramethyl ester)

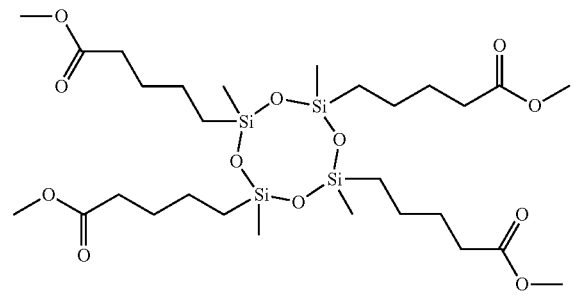

To a stirred solution of methyl 4-pentenoate (793.0 mg, 800 μL, 6.2×10$^{-3}$ mol) in 10 mL of toluene were added 20 μL of Karstedt's platinum catalyst in xylenes and the reaction mixture was stirred at room temperature for 5 minutes. To this was added 337.0 mg (340 μL, 1.4×10$^{-3}$ mol) of 1,3,5,7-tetramethylcyclotetrasiloxane in a drop-wise manner over ten minutes, after which the reaction flask and contents were heated to reflux using a heating mantle and Variac for 2.5 h. The cooled reaction mixture was diluted with a further 10 mL of toluene and decolourized with activated carbon for 18 h. The activated carbon was removed by filtering the reaction mixture through Celite™ and the crude reaction product was purified by flash column chromatography on silica gel (200-400 mesh) and eluted with pentane:ethyl acetate increasing the polarity from 10% to 50% ethyl acetate to yield 777.0 mg ($1.02\times10^{-3}$ mol, 73%) of a clear, colourless oil.

$^1$H NMR (300 MHz, CDCl$_3$): δ 0.06 (s, 12H), 0.52 (m, 8H), 1.37 (m, 8H), 1.6 (m, 8H), 2.30 (t, 8H, J=6 Hz), 3.66 (s, 12H); $^{13}$C NMR (75 MHz, CDCl$_3$): δ -0.7, 16.8, 22.6, 28.2, 33.8, 51.4, 174.2; $^{29}$Si NMR (59.6 MHz, CDCl$_3$): δ -20.2; EI-MS (m/z): M$^+$ 696; FTIR (KBr, 2 cm$^{-1}$): 748, 800, 1075, 1199, 1260, 1437, 1741, 2862, 2875, 2933, 2952.

Preparation of the Compound of Formula I(a) Wherein R$^{1a}$, R$^{1b}$, R$^{1c}$ and R$^{1d}$ are Each (CH$_2$)$_5$C(O)OCH$_3$ (1,3,5,7-tetrakis(5-carboxypentyl)-1,3,5,7-tetramethylcyclotetrasiloxane tetramethyl ester)

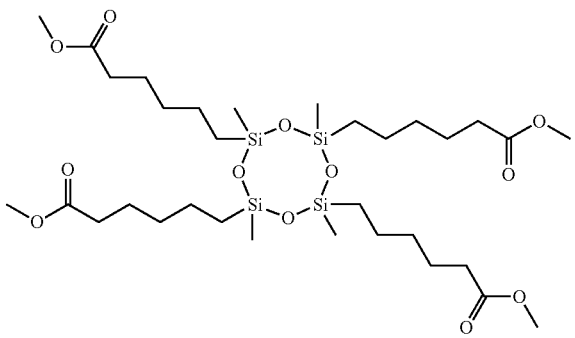

To a stirred solution of methyl 5-pentenoate (718.4 mg, 800 μL, $5.61\times10^{-3}$ mol) in 10 mL of toluene were added 10 μL of Karstedt's platinum catalyst in xylenes and the reaction mixture was stirred at room temperature for 5 minutes. To this was added 317.1 mg (320 μL, $1.32\times10^{-3}$ mol) of 1,3,5,7-tetramethylcyclotetrasiloxane in a drop-wise manner over ten minutes, after which the reaction flask and contents were heated to reflux using a heating mantle and Variac for 1.5 h. The cooled reaction mixture was diluted with a further 10 mL of toluene and decolourized with activated carbon for 18 h. The activated carbon was removed by filtering the reaction mixture through Celite and the crude reaction product was purified by flash column chromatography on silica gel (200-400 mesh) and eluted with pentane:ethyl acetate increasing the polarity from 5% to 50% ethyl acetate to yield 595.5 mg ($7.36\times10^{-4}$ mol, 81%) of a clear, colourless oil.

$^1$H NMR (300 MHz, CDCl$_3$): δ 0.05 (s, 12H), 0.51 (m, 8H), 1.33 (br, 24H), 1.62 (m, 8H), 2.30 (t, 8H, J=9 Hz), 3.66 (s, 12H); $^{13}$C NMR (75 MHz, CDCl$_3$): δ -0.7, 17.0, 22.6, 24.7, 32.6, 34.0, 51.4, 174.2; $^{29}$Si NMR (59.6 MHz, CDCl$_3$): δ -20.2; EI-MS (m/z): (M-CH$_3$)$^+$ 738; FTIR (KBr, 2 cm$^{-1}$): 801, 1081, 1196, 1258, 1436, 1742, 2858, 2930, 2951.

Preparation of the Compound of Formula I(a) Wherein R$^{1a}$, R$^{1b}$, R$^{1c}$ and R$^{1d}$ are Each (CH$_2$)$_6$C(O)OCH$_3$ (1,3,5,7-tetrakis(6-carboxyhexyl)-1,3,5,7-tetramethylcyclotetrasiloxane tetramethyl ester)

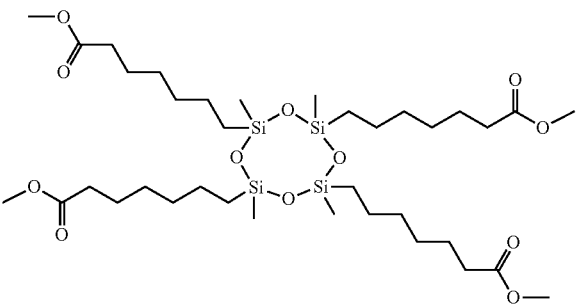

To a stirred solution of methyl 6-hexenoate (590.9 mg, 650 μL, $4.16\times10^{-3}$ mol) in 10 mL of toluene were added 20 μL of Karstedt's platinum catalyst in xylenes and the reaction mixture was stirred at room temperature for 5 minutes. To this was added 218.0 mg (220 μL, $9.08\times10^{-4}$ mol) of 1,3,5,7-tetramethylcyclotetrasiloxane in a drop-wise manner over ten minutes, after which the reaction flask and contents were heated to reflux using a heating mantle and Variac for 18 h. The cooled reaction mixture was diluted with a further 10 mL of toluene and decolourized with activated carbon for 2 h. The activated carbon was removed by filtering the reaction mixture through Celite and the crude reaction product was purified by flash column chromatography on silica gel (200-400 mesh) and eluted with pentane:ethyl acetate increasing the polarity from 5% to 50% ethyl acetate to yield 595.5 mg ($7.36\times10^{-4}$ mol, 81%) of a clear, colourless oil.

$^1$H NMR (300 MHz, CDCl$_3$): δ 0.05 (s, 12H), 0.50 (m, 8H), 1.31 (br, 24H), 1.61 (m, 8H), 2.30 (t, 8H, J=9 Hz), 3.66 (s, 12H); $^{13}$C NMR (75 MHz, CDCl$_3$): δ -0.6, 17.5, 22.8, 24.9, 29.0, 32.8, 34.1, 51.4, 174.2; $^{29}$Si NMR (59.6 MHz, CDCl$_3$): δ -20.2, -20.3; EI-MS (m/z): (M-CH$_3$)$^+$ 793; FTIR (KBr, 2 cm$^{-1}$): 800, 1072, 1176, 1194, 1259, 1436, 1742, 2857, 2924.

Preparation of the Compound of Formula I(a) Wherein R$^{1a}$, R$^{1b}$, R$^{1c}$ and R$^{1d}$ are Each (CH$_2$)$_7$C(O)OCH$_3$ (1,3,5,7-tetrakis(7-carboxyheptyl)-1,3,5,7-tetramethylcyclotetrasiloxane tetramethyl ester)

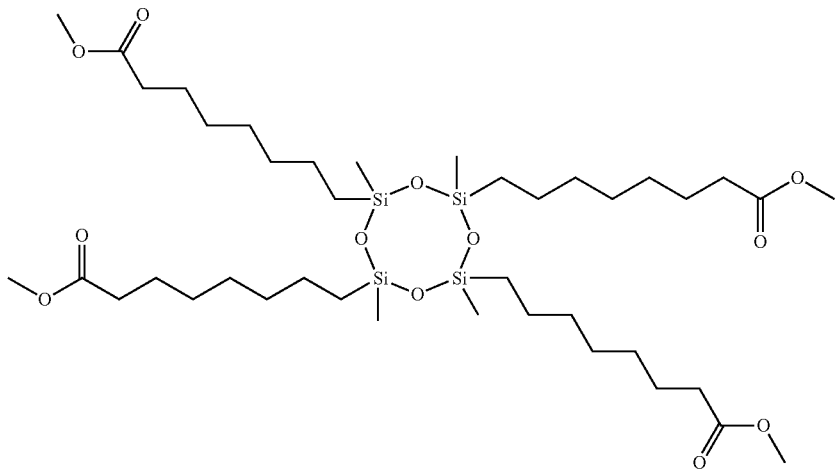

To a stirred solution of methyl 7-octenoate (577.9 mg, 650 μL, 3.70×10$^{-3}$ mol) in 10 mL of toluene were added 10 μL of Karstedt's platinum catalyst in xylenes and the reaction mixture was stirred at room temperature for 5 minutes. To this was added 191.1 mg (210 μL, 7.96×10$^{-4}$ mol) of 1,3,5,7-tetramethylcyclotetrasiloxane in a drop-wise manner over ten minutes, after which the reaction flask and contents were heated to reflux using a heating mantle and Variac for 2 h. The cooled reaction mixture was diluted with a further 10 mL of toluene and was decolourized with activated carbon for 18 h. The activated carbon was removed by filtering the reaction mixture through Celite and the crude reaction product was purified by flash column chromatography on silica gel (200-400 mesh) and eluted with pentane:ethyl acetate (EtOAc) increasing the polarity from 10% to 33% ethyl acetate to yield 403.8 mg (4.67×10$^{-4}$ mol, 59%) of a clear, colourless oil (R$_f$=0.2, 9:1 Pentane:EtOAc).

$^1$H NMR (300 MHz, CDCl$_3$): δ 0.05 (s, 12H), 0.50 (m, 8H), 1.30 (br, 32H), 1.62 (m, 8H), 2.30 (t, 8H, J=6 Hz), 3.66 (s, 12H); $^{13}$C NMR (75 MHz, CDCl$_3$): δ −0.6, 17.1, 22.9, 25.0, 29.0, 29.1, 32.9, 34.1, 51.4, 174.3; $^{29}$Si NMR (59.6 MHz, CDCl$_3$): δ −20.2; EI-MS (m/z): (M-CH$_3$)$^+$ 849; FTIR (KBr, 2 cm$^{-1}$): 800, 1072, 1086, 1175, 1259, 1436, 1743, 2855, 2927, 2950.

Preparation of the Compound of Formula I(a) Wherein R$^{1a}$, R$^{1b}$, R$^{1c}$ and R$^{1d}$ are Each (CH$_2$)$_9$C(O)OCH$_3$ (1,3,5,7-tetrakis(9-carboxynonyl)-1,3,5,7-tetramethylcyclotetrasiloxane tetramethyl ester)

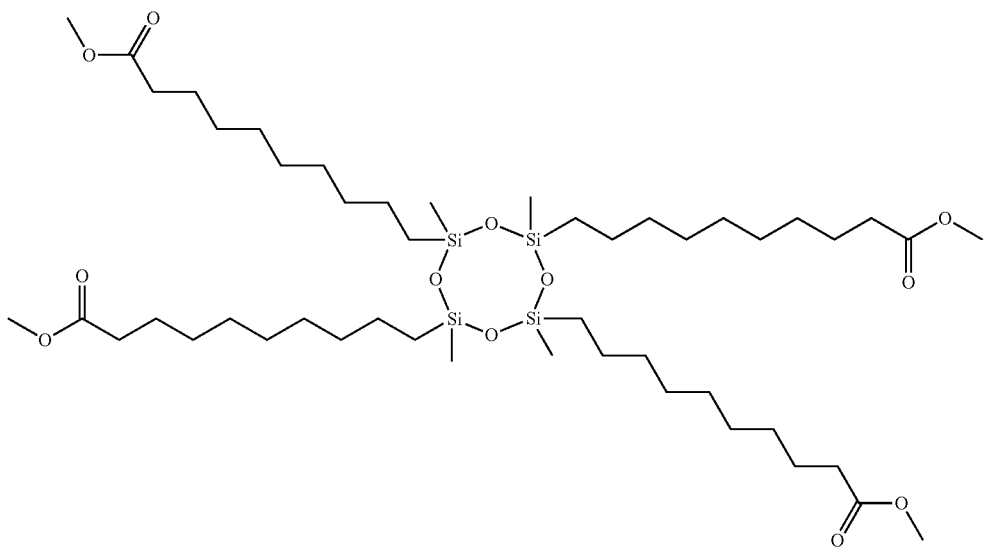

To a stirred solution of methyl 9-decenoate (1.369 g, 1.6 mL, 7.43×10$^{-3}$ mol) in 10 mL of toluene were added 10 μL of Karstedt's platinum catalyst in xylenes and the reaction mixture was stirred at room temperature for 5 minutes. To this was added 396.4 mg (400 μL, 1.65×10$^{-3}$ mol) of 1,3,5,7-tetramethylcyclotetrasiloxane in a drop-wise manner over ten minutes, after which the reaction flask and contents were heated to reflux using a heating mantle and Variac for 2 h. The cooled reaction mixture was diluted with a further 10 mL of toluene and decolourized with activated carbon for 18 h. The activated carbon was removed by filtering the reaction mixture through Celite and the crude reaction product was purified by flash column chromatography on silica gel (200-400 mesh) and eluted with pentane:ethyl acetate increasing the polarity from 10% to 33% ethyl acetate to yield 931.5 mg (9.54×10$^{-4}$ mol, 58%) of a clear, colourless oil.

$^1$H NMR (300 MHz, CDCl$_3$): δ 0.05 (s, 12H), 0.50 (m, 8H), 1.27 (br, 48H), 1.61 (m, 8H), 2.30 (t, 8H, J=6 Hz), 3.66 (s, 12H); $^{13}$C NMR (75 MHz, CDCl$_3$): δ −0.6, 17.2, 23.0, 25.0, 29.2, 29.3, 29.41, 29.43, 33.2, 34.1, 51.4, 174.5; $^{29}$Si NMR (59.6 MHz, CDCl$_3$): δ −20.2; EI-MS (m/z): (M-CH$_3$)$^+$ 961; FTIR (KBr, 2 cm$^{-1}$): 800, 1071, 1086, 1172, 1196, 1258, 1436, 1462, 1745, 2855, 2927.

Chain Length Selectivity—Esterification of octan-1-ol

The chain length selectivity of N435 towards the tetracyclosiloxane methyl esters used in the present studies was determined by combining the desired tetracyclosiloxane methyl ester with octane-1-ol in a 1:4 mol ratio so that the concentration of the cyclotetrasiloxane methyl ester was 160 mM in toluene.

The monomers were dissolved in toluene, preheated to 100° C. and combined with 5 wt % of N435 as the catalyst. Enzyme-free reactions were carried out in the same way without the addition of any catalyst. Each reaction was stirred at 100° C. for 2 h at 150 rpm. The reaction was terminated by filtering the reaction mixture to remove the immobilized enzyme and the solvent was removed under reduced pressure. The degree of conversion was monitored using the appropriate resonances in the $^1$H NMR spectrum. The reported average conversions were the result of four replicate trials.

Polymerization of a Cyclotetrasiloxane Methyl Ester with octan-1,8-diol

A cooled, 10 mL flame dried round bottomed flask was charged with 171.1 mg (1.75×10$^{-4}$ mol) of the compound of Formula I(a) wherein R$^{1a}$, R$^{1b}$, R$^{1c}$ and R$^{1d}$ are each (CH$_2$)$_9$C(O)OCH$_3$ and 52.2 mg (3.53×10$^{-4}$ mol) of octane-1,8-diol and melted to form a homogeneous mixture at 100° C. for 5 minutes using a magnetic stirring bar. Novozyme 435®

(N435®) was added to the reaction mixture and stirred for 24 h after which point a sample was removed for $^1$H NMR analysis. At this time the polymerization was placed under vacuum and allowed to continue for an additional 20 h. The reaction was then stopped because the viscosity of the reaction mixture was such that the stir bar ceased stirring. The reaction was quenched by the addition of 10 mL of cool CHCl$_3$ and stirred at 21° C. for 10 minutes. The N435 beads were removed by filtering the reaction mixture through a medium porosity glass fritted Buchner funnel. The beads were rinsed with two volumes of 10 mL of CHCl$_3$ and the excess solvent was removed in vacuo.

III. Results and Discussion

Synthesis of Cyclotetrasiloxane Esters

Cyclotetrasiloxane esters were produced via hydrosilylation chemistry using the commercially available Karstedt's platinum catalyst and isolated after chromatography in moderate to good yields (Scheme 1).

Scheme 1

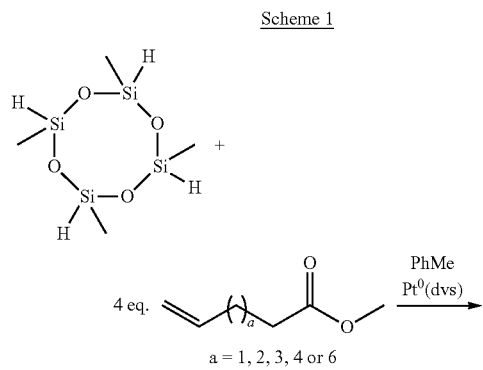

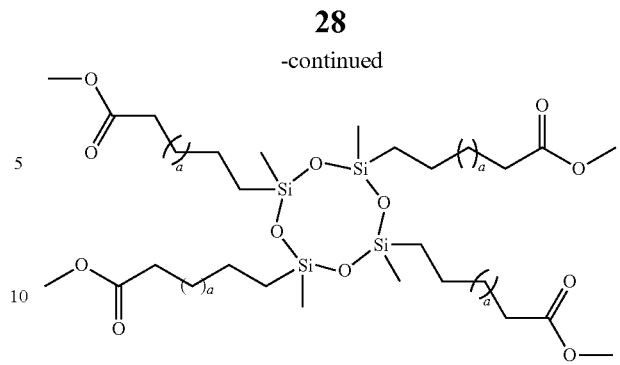

The structures of the methyl esters were confirmed using previously published data for linear siloxane-containing esters.[56] $^{29}$Si nuclear magnetic resonance (NMR) spectroscopy revealed, for all of the esters presented herein, two $^{29}$Si resonances suggesting that a mixture of isomers of cyclotetrasiloxane rings were present.[54] These isomers were confirmed to have been present in the Si—H functionalized cyclotetrasiloxane starting material and did not result from the platinum-catalyzed hydrosilylation chemistry. All of the esters were isolated as the anti-Markovnikov hydrosilylation adduct as determined by $^1$H NMR.

Chain Length Selectivity

Increasing the steric bulk of the coupling partners in enzymatic polyesterification reactions affects the rate of the reaction as well as the average molecular mass of the final polymer. Some previous studies on a different system have determined that architectural aspects within the active site of the enzyme control the outcome of a given reaction.[55] Increasing the distance between the trisiloxane moiety and the reactive ester group, such that the silicon atom was outside of the active site of the lipase resulted in increased transesterification.[30]

The incorporation of four esters into a cyclic siloxane framework gave a similar trend (Scheme 2, FIG. 1). The conversion of the methyl esters to the corresponding octyl esters was greatest when the C10 ester (compound of Formula I(a) wherein $R^{1a}$, $R^{1b}$, $R^{1c}$ and $R^{1d}$ are each $(CH_2)_9$ $C(O)CH_3$; yield=66%) was the starting material for the reaction.

Scheme 2

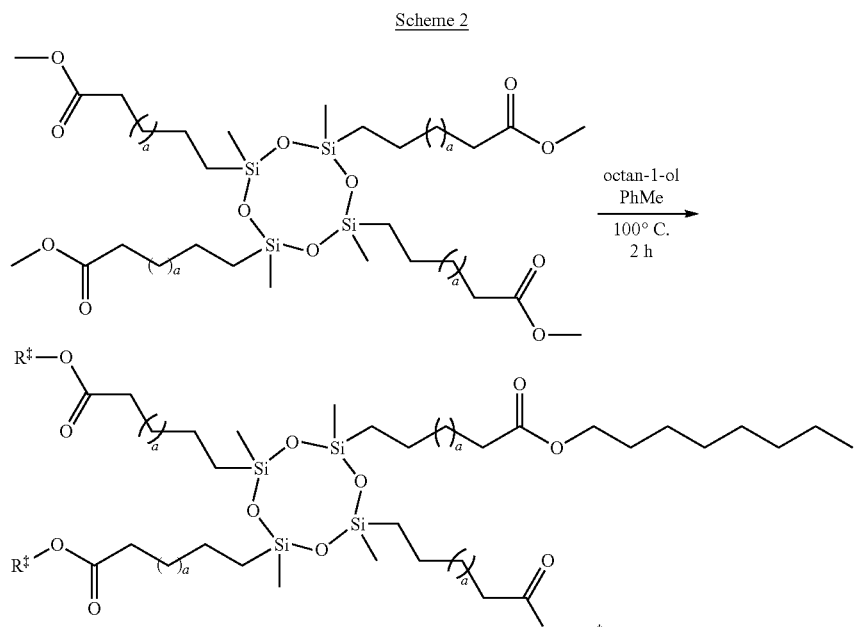

The C5 (compound of Formula I(a) wherein $R^{1a}$, $R^{1b}$, $R^{1c}$ and $R^{1d}$ are each $(CH_2)_4C(O)CH_3$; yield=2%), C6 (compound of Formula I(a) wherein $R^{1a}$, $R^{1b}$, $R^{1c}$ and $R^{1d}$ are each $(CH_2)_5C(O)CH_3$; yield=2.5%), C7 (compound of Formula I(a) wherein $R^{1a}$, $R^{1b}$, $R^{1c}$ and $R^{1d}$ are each $(CH_2)_6C(O)CH_3$; yield=4.5%) and C8 (compound of Formula I(a) wherein $R^{1a}$, $R^{1b}$, $R^{1c}$ and $R^{1d}$ are each $(CH_2)_7C(O)CH_3$; yield=13.5%) methyl esters were not observed to have as high yield for the conversion to the octyl ester using the enzyme N435.

These results are in contrast to an earlier investigation in which transesterification increased at the point when a C7-trisiloxane was the substrate. While not wishing to be limited by theory, this can be attributed to the geometric differences between a linear siloxane and the larger tetracyclosiloxane ring system. Despite these differences from the previous work, the present studies demonstrate that increasing the distance between the larger siloxane moiety and the ester moiety leads to higher transesterification.

Oligomerization of Cyclotetrasiloxane Esters

Based on the results from the above-discussed chain length selectivity studies, the compound of Formula I(a) wherein $R^{1a}$, $R^{1b}$, $R^{1c}$ and $R^{1d}$ are each $(CH_2)_9C(O)OCH_3$ was chosen for polymerization experiments (Scheme 3). Enzymatic polymerizations were performed using a 2:1 mole ratio of the monomer octane-1,8-diol to the cyclotetrasiloxane ester monomer. Using 5 wt % of N435 with respect to the total mass of the monomers used, polymerizations were carried out in the absence of solvent, under air, with magnetic stirring at various temperatures for predetermined time periods. The unfractionated products were characterized by NMR spectroscopy and MALDI-ToF MS.

where x and y are integers corresponding to the number of each monomer in the formula. For higher order oligomers it was difficult to describe the architectural arrangement of appendages with certainty. Where intramolecular transesterification events occur they are denoted herein with $cyc^n$ where n refers to the number of intramolecular cyclization events.

In the absence of any enzyme catalyst, only starting materials were recovered and transesterification could not be detected by $^1H$ NMR or MALDI-ToF MS. The viscosity of the reaction mixture increased substantially with the addition of N435. It was not uncommon for the reaction mixture to become so viscous it was difficult for the magnetic stirring bar to spin, and over 72-120 h, spinning often ceased. In order to study the reaction conditions, two parameters, temperature and enzyme loading, were examined.

Temperature Effect

Temperature is a factor in regulating enzymatic activity. However in some polymer systems, the choice of monomers can dictate the optimal and maximum temperature that can be employed, and this range can be well above the physiological maximum for any given enzyme. Previous reports suggested that 70° C.-90° C. was the optimal temperature for carrying out N435-mediated polymerizations between aliphatic esters and alcohols.[23-27] In the presence of one or more siloxane-containing monomers however, the temperature for polymerization increased to 130° C. without catastrophic denaturation of the enzyme catalyst.[29,56]

The enzymatic polymerization of the cyclotetrasiloxane ester of Formula I(a) wherein $R^{1a}$, $R^{1b}$, $R^{1c}$ and $R^{1d}$ are each $(CH_2)_9C(O)OCH_3$ and octane-1,8-diol was carried out in the absence of solvent or vacuum using 5 wt % of N435 for 24

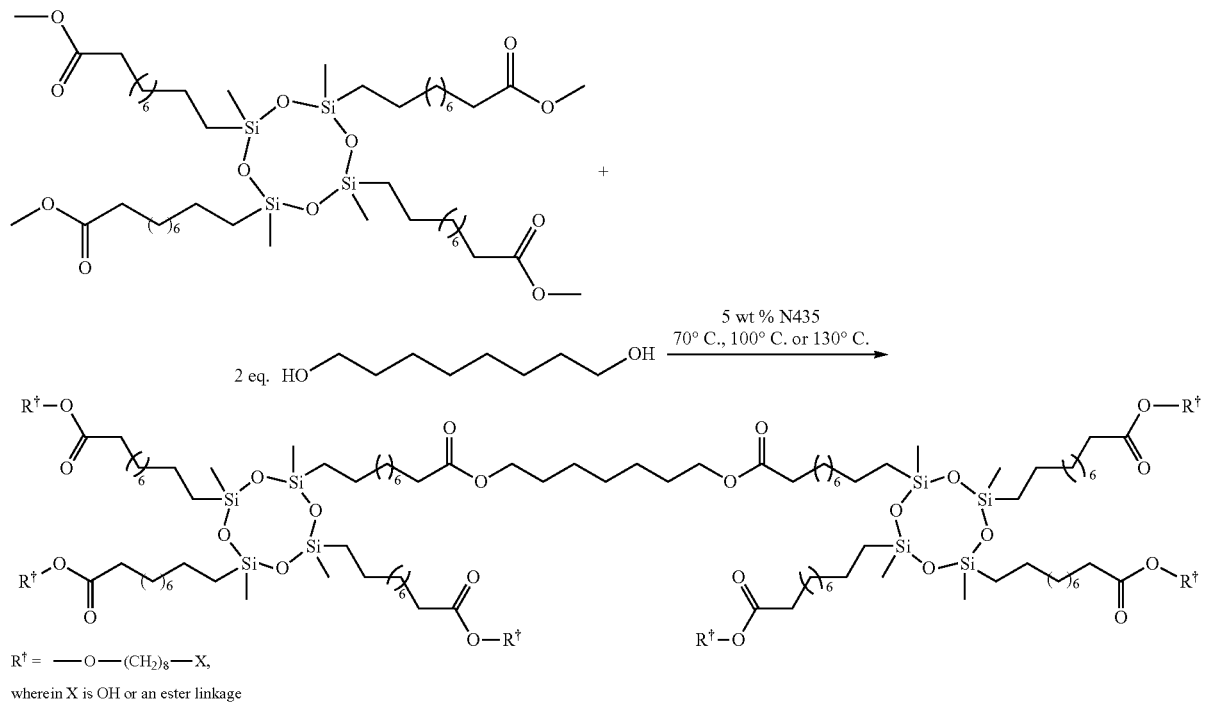

Scheme 3

The cyclotetrasiloxane ester, designated as monomer A, and octane-1,8-diol, designated as monomer B, can be combined in multiple ways and are written herein as $A_xB_y$ h. Conversion of the cyclotetrasiloxane ester of Formula I(a) wherein $R^{1a}$, $R^{1b}$, $R^{1c}$ and $R^{1d}$ are each $(CH_2)_9C(O)OCH_3$ was determined by $^1H$ NMR spectroscopy by comparing the integration values for the protons of the methylene group in the alpha position with respect to the carbonyl of the methyl ester (2.35 ppm) and the protons of the methylene group which is in the alpha position with respect to the hydroxyl group in octane-1,8-diol fragment in the newly formed octyl ester (4.02 ppm).

The N435-catalyzed polyesterification gave low to moderate conversion of the ester groups depending on reaction temperature. There was little difference in conversion at 70° C. or 100° C. where esterification was 71±2% and 74±2% (Table 1). Conversion dropped to 40±6% when the temperature was increased to 130° C. These findings agree well with some previous reports concerning the polymerization of aliphatic esters and alcohols. However, the present results contrast with other previous work in which a positive correlation was observed as the temperature was increased from 35-130° C.[29,56]

Figure 2:
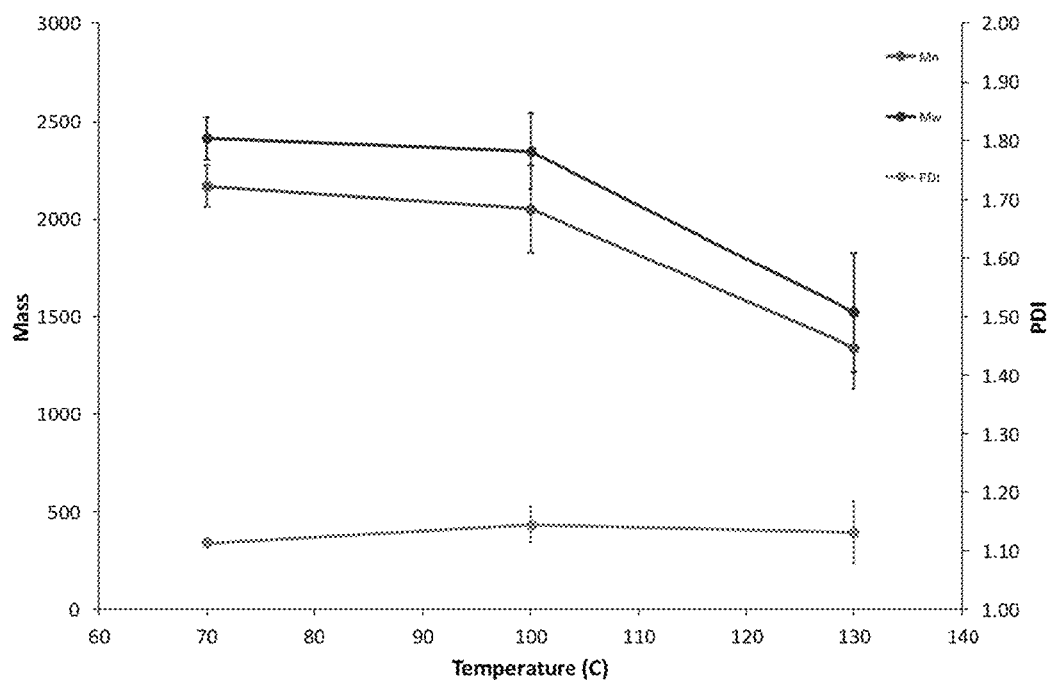
FIG. 2 is a graphical representation of the number average molecular mass, weight average molecular mass and polydispersity index of the N435-synthesized polyesters as a function of reaction temperature.

The growth of the polymer chains can be followed using matrix assisted laser desorption ionization time of flight mass spectrometry (MALDI-ToF MS). MALDI-ToF MS allows for the identification of a series of mass ions which represent the components of the final product mixture. The distribution of the chemical species obtained from the MALDI-ToF MS experiments were used to determine the number average ($M_n=\Sigma N_i M_i/\Sigma N_i$) and weight average ($M_w=\Sigma N_i M_i^2/\Sigma N_i M_i$) molecular mass of the polyester, as well as the polydispersity index (PDI=$M_w/M_n$). After 24 h of reaction time, branched oligomeric species of the form $A_xB_y$ as well as $A_xB_ycyc^n$ were identified in the reaction mixture. The molecular weights of the unfractionated branched polymers were calculated after 24 h at 70° C., 100° C. and 130° C. The $M_n$, $M_w$ and PDI at 70° C. ($M_n$=2169, $M_w$=2414, PDI=1.11) and 100° C. ($M_n$=2052, $M_w$=2347, PDI=1.14) show little variation (FIG. 2). An increase in the reaction temperature to 130° C. brought about a decrease in the overall mass value of growing polymer chains ($M_n$=1339, $M_w$=1521) although no change in the mass dispersity (PDI=1.13) was detectable using MALDI-ToF MS.

Figure 3:
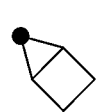
FIG. 3 shows pictogram representations of the smallest cyclic oligoesters identified by MALDI-ToF MS. The square represents the fragment derived from the compound of Formula I(a) wherein $R^{1a}$, $R^{1b}$, $R^{1c}$ and $R^{1d}$ are each $(CH_2)_9$ $C(O)OCH_3$ (A) and the dot is the fragment derived from octane-1,8-diol (B).
Figure 3:
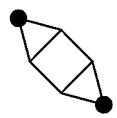
Figure 3:
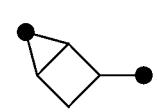

Analysis of the MALDI-ToF MS spectra indicate linear oligomers were produced. Intramolecular esterification, leading to polycyclic species at all three of the examined temperatures, was also apparent (FIG. 3). At 70° C. and 100° C. the enzyme produced fully and partially branched dimers, as well as partially branched trimers and tetramers within the 24 h time frame of the reaction. Cyclic and linear dimers dominate the MALDI-ToF spectrum and are the largest contributing factor to the $M_n$ and M. At 70° C. and 100° C., the dominant chemical species (based on the ion intensities) was the $AB_2cyc^2$ oligomer with m/z=1163. Additionally, at 70° C., the partially condensed $AB_2cyc$ (1196 m/z) oligomer as well as the ABcyc oligomer (1082 m/z) were present in varying amounts. At 130° C., the dominant chemical species is the unreacted cyclotetrasiloxane ester of Formula I(a) wherein $R^{1a}$, $R^{1b}$, $R^{1c}$, and $R^{1d}$ are each $(CH_2)_9C(O)OCH_3$. While not wishing to be limited by theory, this is a result of thermal denaturation of the enzyme catalyst which is known to denature in solution at 62° C. Accordingly, the cyclic siloxane core of the compound of Formula I(a) wherein $R^{1a}$, $R^{1b}$, $R^{1c}$ and $R^{1d}$ are each $(CH_2)_9C(O)OCH_3$ therefore does not appear to impart the same thermal protection to the enzyme as has been observed for linear polysiloxane species.[29,56] There is evidence of intramolecular esterification at this temperature, but the relative proportion of cyclic species is very low.

Enzyme Loading

In order to further study the reaction conditions, the amount of enzyme included in the reaction was increased from 5 wt % to 10 wt %. Increasing the catalyst loading gave a viscous mixture within the first few hours and after 24 h conversion reached 77% as compared to 74% when 5 wt % N435 was used. The dominant mass ion in the MALDI-ToF MS spectrum was the $AB_2cyc^2$ species. Unlike reactions prepared with only 5 wt % N435, the intraesterified species $AB_2cyc$, $AB_2cyc^2$ and $AB_3cyc$, but not the ABcyc intermediate, were identified from the MALDI-ToF MS spectra. The most prevalent difference was noted for the $A_2B_x$ series of dimers for which the intraesterified oligomers were the only species that were present within the crude polymer mixture. At 10 wt % N435, the $A_3B_x$ and $A_4B_x$ series of oligomers were distributed between branched linear and cyclic species in a similar manner to that found at 5 wt % catalyst loading.

Time Course Profile

A more complete understanding of the enzymatic oligomerization under study is useful so that the reaction conditions can be optimized. A time course profile of the reaction was carried out by withdrawing 2 μL aliquots at predetermined time points and performing MALDI-ToF MS analysis. This method allows for the identification of each chemical species, as well as the change in the distribution of each species, with the progression of time. The time course profile was generated over the first six hours of the reaction cycle. After 24 h, the reaction mixture contained a large amount of high molecular weight species and analysis by MALDI-ToF MS was not suitable. The presence of high molecular weight species was inferred from the decrease in the apparent $M_n$ and $M_w$ when the polymerization was continued for longer reaction times.

Figure 4:
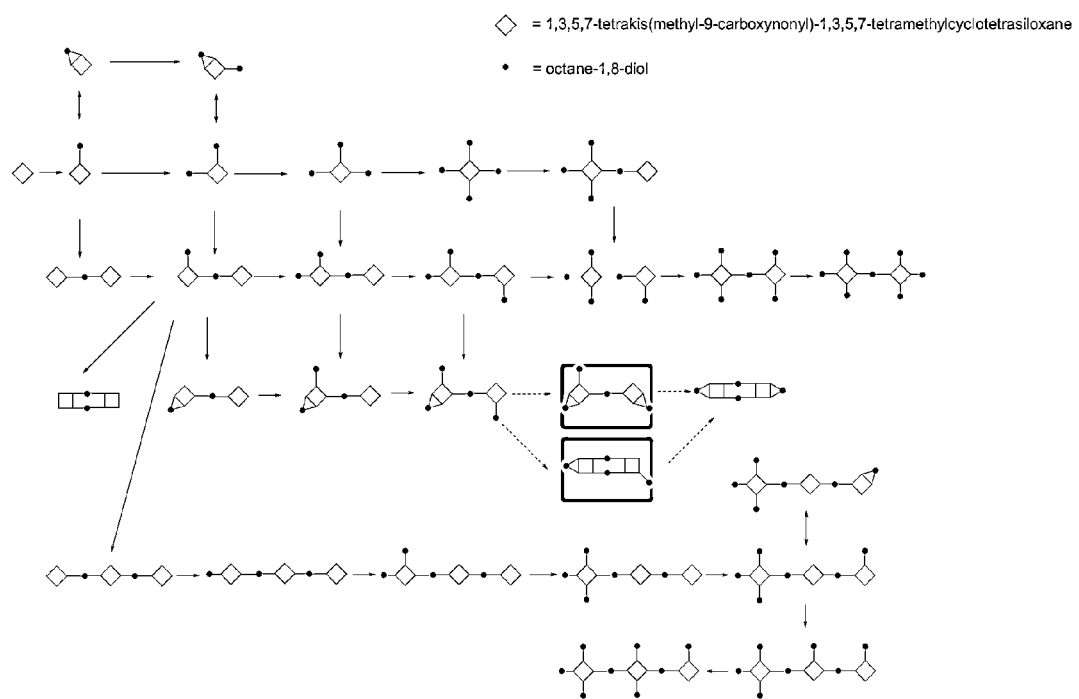
FIG. 4 is a pictographic representation of the first hour of the N435-catalyzed oligomerization of the compound of Formula I(a) wherein $R^{1a}$, $R^{1b}$, $R^{1c}$ and $R^{1d}$ are each $(CH_2)_9$ $C(O)OCH_3$ and octane-1,8-diol under solvent-free conditions. The structures in the grey shaded box were not detectable by MALDI-ToF MS but are thought to have been synthesized as they are the only pathways to give the polycyclic oligomer $A_2B_4cyc^3$ at 2306 m/z.

The N435-mediated oligomerization of the cyclotetrasiloxane ester of Formula I(a) wherein $R^{1a}$, $R^{1b}$, $R^{1c}$ and $R^{1d}$ are each $(CH_2)_9C(O)OCH_3$ with octane-1,8-diol progressed by the stepwise addition of octanediol units to each of the four ester units of the $D_4$ core. A pictographic representation of the potential reaction profile is presented in FIG. 4. There is evidence for the formation of partially transesterified esters to give AB, $AB_2$, $AB_3$ along with the fully transesterified $AB_4$. The complete transesterification of all four ester groups, to form $AB_4$, was not a requirement for oligomerization. Within the first few minutes of the reaction, $A_2B_x$ (x=1-4) species are present in the mixture suggesting that all of the branched $AB_x$ species are equally available for releasing the enzyme from its acylated state. The first evidence of intramolecular esterification was seen as early as three minutes of reaction time, with the mass ion for the $A_2B_5cyc$ species being present in the MALDI-ToF MS spectrum. By four minutes, small amounts of $A_3B_x$ oligomers, with low degrees of branching were seen ($A_3B_x$ with n=2-5) and after seven minutes the first signs of tetrameric oligomers were detectable. Within the first hour, these oligomers were predominantly acyclic species with only a few exceptions which can be seen in FIG. 4. Beyond two hours of reaction time, there is evidence for higher order branched cyclic and acyclic oligomers. However on the time scale of these experiments, unreacted monomers remain in the reaction mixture.

Figure 5:
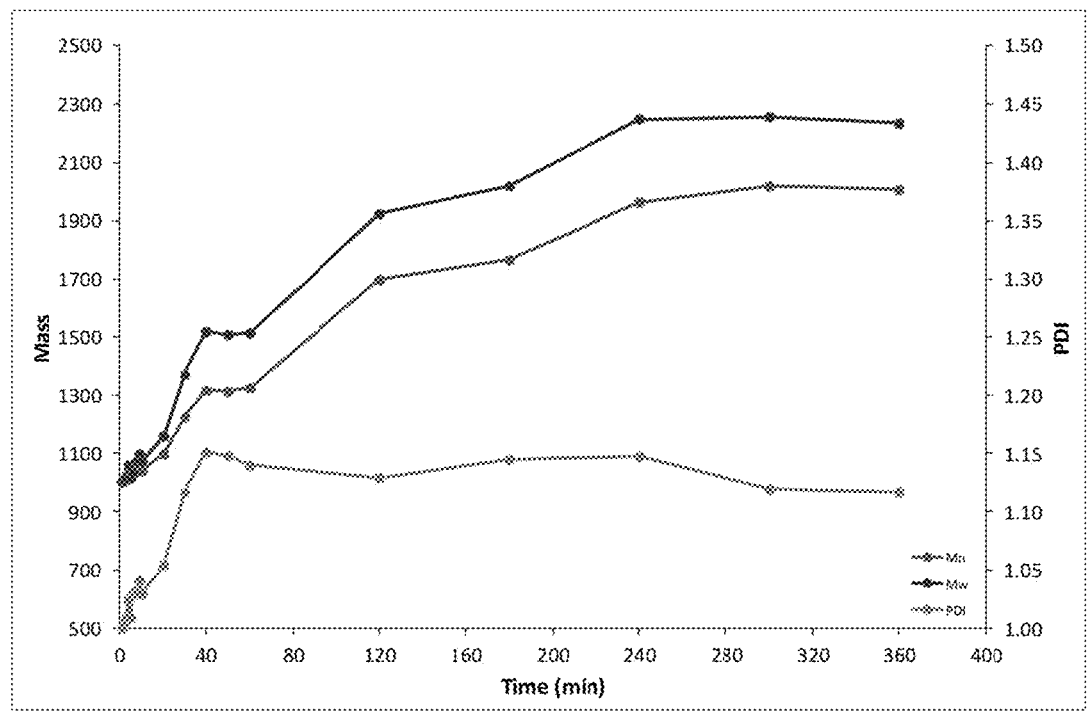
FIG. 5 shows the time course profile of the N435-catalyzed oligomerization of the compound of Formula I(a) wherein $R^{1a}$, $R^{1b}$, $R^{1c}$ and $R^{1d}$ are each $(CH_2)_9C(O)OCH_3$ with octane-1,8-diol. Error bars have been omitted from the graph for the sake of clarity.

The growth of $M_n$, $M_w$ and the change in PDI of the siloxane-derived oligomers is presented in FIG. 5. Between the initiation of the reaction and the fourth hour, there was a steady increase in the overall mass of the growing oligomer chain. Beyond four hours there was little change in the polymer mass. This was also the time point where extensive cyclization occurred. While not wishing to be limited by theory, this was attributed to the increasing viscosity of the polymeric mixture, and the resulting low mobility of each chemical species. The PDI of the polymer chains increased over the first 40 minutes of the reaction reaching a maximum of 1.15. By the end of six hours the dispersity of the molecular mass dropped to 1.12 as a result of intramolecular esterification.

Extended time course studies surpassing 24 h in duration showed an apparent mass decrease. However, total monomer conversion followed by $^1$H NMR suggested that monomer conversion, which reached 75% after 24 h, increased to 80% after 120 h. With these constant levels of conversion and the apparent decrease in the molecular mass of the polymer chains, while not wishing to be limited by theory, two hypotheses can be formed. Firstly, growing chains may link together in any number of architectures to produce cross-linked sheets or three dimensional networks for which MALDI-ToF MS is ill-suited to analyze. The second potential explanation was that the oligomeric chains are equally accessible by the active site of the enzyme, and chain transfer reactions are occurring. This second option seems less likely given that loosely cross-linked networks, with some smaller amounts of smaller oligomers, formed when reaction times were extended to 96-120 h. The soluble fraction from the cross-linked gels was obtained by swelling the gel in THF or CHCl$_3$ for 2 h and analyzing the resulting residue by MALDI-ToF MS. The soluble fraction from the gels was mainly made up of lower molecular weight cyclic species and dimers. The main species present in the THF soluble fractions were AB$_2$cyc and A$_2$B$_4$cyc$^3$ with some evidence for incompletely condensed oligomers.

Solvated Oligomerization

The presence of non-linear species during polymerization relates directly to the ring-chain equilibrium of the system. The equilibrium favours chain formation when monomer concentration is high.[58] This should be the case even more so when reactions are carried out in the absence of solvent. Where the equilibrium is established is a direct function of the monomers that are chosen. Despite the high apparent concentration of monomers under solvent-free conditions, ring formation was observed; not only after high conversions was reached, but also in the time scale of minutes to hours.

There are reports in the literature discussing the enzyme-mediated synthesis of polyester macrocycles.[58-60] The main feature driving the formation of macrocycles is a highly solvated system.

A series of experiments with the aim of producing one, or a small few, polycyclic macrocyles was performed. At a concentration of 50 mM using 5 wt % of N435, conversion of the methyl esters was high at 95% ($^1$H NMR), which suggested that the enzyme catalyst produced a mixture of new compounds. The MALDI-ToF MS spectrum was dominated by ion peaks corresponding to AB$_2$cyc$^2$ and A$_2$B$_4$cyc$^3$. In all circumstances, AB$_2$cyc$^2$ was the mass ion of greatest intensity while the A$_2$B$_4$cyc$^3$ ion varied between 20-38% with respect to the base peak mass ion. However at this concentration, the presence of incompletely cyclized monomers was not totally suppressed. Reducing the concentration to 25 mM gave similar conversion of the methyl esters, 90-95%. Again the two dominant macrocycles were the AB$_2$cyc$^2$ (base peak in the mass spectra arbitrarily assigned a value of 100%) and A$_2$B$_4$cyc$^3$ (5-13%), with some evidence for A$_3$B$_6$cyc$^4$ as well as incompletely condensed species.

Reducing the monomer concentration further to 20 mM and 10 mM afforded greater than 85% conversion with a similar distribution of products. At concentrations below 25 mM it had become apparent, by examination of the $^1$H NMR spectra, the acrylic resin on which the CalB enzyme was immobilized had started to degrade. The situation was more prevalent at the lowest concentration used in this study, 5 mM, where only 50% conversion was attained after 120 h.

The AB$_2$cyc$^2$ macrocycle was isolated via flash chromatography, using 15% ethyl acetate in hexanes, in low yields (17-26%). The higher order fully and partially condensed macrocycles were not isolatable by column chromatography in the present studies. The structure of the AB$_2$cyc$^2$ macrocycle was confirmed by $^1$H NMR and mass spectrometry. The MALDI-ToF MS spectrum showed the presence of this species and no incompletely cyclized molecules. This was confirmed by FAB-MS which showed the expected isotope pattern for a compound containing four silicon atoms.

Example 2

Enzymatic Modification of Spherosilicates

A spherosilicate of Formula II(a) wherein $R^{4a}$, $R^{4b}$, $R^{4c}$, $R^{4d}$, $R^{4e}$, $R^{4f}$, $R^{4g}$ and $R^{4h}$ are each $(CH_2)_9C(O)OCH_3$ was synthesized in the present studies using hydrosilylation chemistry. For the first time, the enzymatic modification of Q$_8$ cubic spherosilicate derivatives has been shown. Using MALDI-ToF MS each macrocyclic oligomer that was produced was assigned. The thermal tolerance of the unmodified spherosilicate of Formula II(a) wherein $R^{4a}$, $R^{4b}$, $R^{4c}$, $R^{4d}$, $R^{4e}$, $R^{4f}$, $R^{4g}$ and $R^{4h}$ are each $(CH_2)_9C(O)OCH_3$, and the enzymatically modified spherosilicate was tested. The results of the present studies showed that both coatings could withstand temperatures up to 200° C. for 24 h.

I. Materials and Instrumentation

Materials

Octakis(dimethylsiloxy)-T8-silsesquioxane was obtained from Gelest (Morristown, Pa., USA). Immobilized lipase from *Candida antarctica* (Novozyme-435, N435), 9-decenoic acid, and Karstedt's platinum catalyst (Pt$^0$-1,3-divinyl-1,1,3,3-tetramethyldisiloxane complex in xylenes) was obtained from Sigma-Aldrich (Oakville, Ontario, Canada). Octane-1,8-diol and p-toluene sulphonic acid were obtained from Alpha Aaesar (Ward Hill, N.J., USA). Deuterated chloroform (CDCl$_3$, 99.9% deuterated) was obtained from Cambridge Isotope Laboratories (Andover, Md., USA). Methanol and toluene were obtained from suitable sources, were of the highest available grade and were stored over 4 Å molecular sieves prior to use. All other solvents were of the highest available grade and were used without purification.

Instrumentation

Nuclear Magnetic Resonance (NMR) spectra ($^1$H (300 MHz), $^{13}$C (75 MHz), $^{29}$Si (59.6 MHz)) were acquired on a 300 MHz Bruker Avance-300 NMR spectrometer. Matrix Assisted Laser Desorption Ionization Time of Flight Mass Spectrometry (MALDI ToF MS) was performed on a Bruker Autoflex Mass spectrometer operating in positive reflectance mode using Dithranol/NaCl as the matrix. Fourier-transform infrared (FT-IR) spectroscopy was performed on a Mattson Research Series IR spectrophotometer operating in transmittance mode.

II. Reactions

Preparation of methyl 9-decenoate

To a stirred solution of 9-decenoic acid (8.2 mL, 44.2 mmol) in methanol (40 mL) was added p-toluene sulfonic acid (0.314 g, 1.7 mmol) and one inert boiling chip. The reaction mixture was refluxed for 19 hours after which time the methanol was removed in vacuo. The remaining residue was dissolved into ethyl acetate (2×20 mL) and washed twice with 20 mL of distilled water and twice with 10 mL of saturated KHCO$_3$. The combined organic fractions were dried over sodium sulphate, filtered and the solvent was removed under reduced pressure to yield 7.86 g (42.68 mmol, 96%) of a straw-coloured oil.

$^1$H NMR (300 MHz, CDCl$_3$): δ 1.30 (br 8H), 1.60 (m, 2H), 2.03 (m, 2H), 2.30 (t, 2H, J=7.5 Hz), 3.66 (s, 3H), 4.94 (m, 2H), 5.78 (m, 1H); $^{13}$C NMR (75 MHz, CDCl$_3$): δ 24.9, 28.8, 28.9, 29.0, 33.7, 34.1, 51.4, 114.2, 139.1, 174.3; EI-MS (m/z): M$^+$ 184.

Preparation of the Compound of Formula II(a) Wherein R$^{4a}$, R$^{4b}$, R$^{4c}$, R$^{4d}$, R$^{4e}$, R$^{4f}$, R$^{4g}$ and R$^{4h}$ are Each (CH$_2$)$_9$C(O)OCH$_3$ (octakis(9-carboxynonyldimethylsiloxy)-spherosilicate octamethyl ester)

A cooled, flame-dried round bottomed flask was charged with methyl-9-decenoate (0.550 mL, 2.1 mmol), toluene (10 mL), and Karstedt's platinum catalyst (20 μL) and stirred for 10 minutes at room temperature. A solution of octakis (dimethylsiloxy)-T8-silsesquioxane (310 mg, 3.05×10$^{-4}$ mol) in 10 mL of toluene was added drop wise through a rubber septum over 15 minutes and the reaction mixture heated to reflux for 6 hours. The reaction mixture was decolourized with activated carbon at room temperature for 2 hours, filtered through Celite, and the solvents were removed in vacuo. The residue from the reaction flask was purified by column chromatography on 18.0 g of silica gel using ethyl acetate in pentane, increasing the polarity from 10% to 100% ethyl acetate to yield 523.6 mg (2.1×10$^{-4}$ mol, 69%) of a colourless oil.

$^1$H NMR (300 MHz, CDCl$_3$): δ 0.11 (s, 12H), 0.57 (m, 8H), 1.28 (s, 24H), 1.61 (m, 8H), 2.30 (t, 8H, J=7.5 Hz), 3.66 (s, 12H); $^{13}$C NMR (75 MHz, CDCl$_3$): δ -0.3, 17.7, 23.0, 25.0, 29.2, 29.4, 29.5, 33.5, 34.1, 51.4, 174.3; $^{29}$Si NMR (59.6 MHz, CDCl$_3$, Cr(acac)$_3$, TMS 0.0 ppm): δ 12.6, -108.9; MALDI ToF MS (m/z): (M+Na)$^+$ 2512; FTIR (KBr, 2 cm$^{-1}$): 790, 845, 1087, 1170, 1252, 1742, 2854, 2924.

Oligomerization of the Compound of Formula II(a) Wherein R$^{4a}$, R$^{4b}$, R$^{4c}$, R$^{4d}$, R$^{4e}$, R$^{4f}$, R$^{4g}$ and R$^{4h}$ are Each (CH$_2$)$_9$C(O)OCH$_3$ with octane-1,8-diol The compound of Formula II(a) wherein R$^{4a}$, R$^{4b}$, R$^{4c}$, R$^{4d}$, R$^{4e}$, R$^{4f}$, R$^{4g}$ and R$^{4h}$ are each (CH$_2$)$_9$C(O)OCH$_3$ and octane-1,8-diol were melted together at 70° C., 100° C. or 130° C. (see results and discussion section, below) in a temperature-controlled oil bath for 1-2 minutes and then dissolved into toluene to a final concentration of (8 mM). N435 (5-10 wt % with respect to the mass of the monomers) was added. The reaction flask was fitted with a water-cooled condenser and the contents of the flask were stirred at 150 rpm. After predetermined time periods, the reactions were cooled to 21° C. and diluted with 5 mL of cool chloroform for 10 minutes. The lipase catalyst N435 was removed by filtration and the remaining components in the reaction mixture were washed with two 10 mL volumes of chloroform. Solvents were removed in vacuo and the resulting oligomeric products were characterized by NMR and MALDI-ToF MS.

III. Results and Discussion

The synthesis of a C10-ester modified spherosilicate, the compound of Formula II(a) wherein R$^{4a}$, R$^{4b}$, R$^{4c}$, R$^{4d}$, R$^{4e}$, R$^{4f}$, R$^{4g}$ and R$^{4h}$ are each (CH$_2$)$_9$C(O)OCH$_3$, has been demonstrated in the present studies, employing hydrosilylation chemistry using Karstedt's platinum catalyst (Scheme 4). The hydrosilylation of the dimethylsiloxy group of the starting material with the terminal alkene of methyl-9-decenoate proceeded as desired generating the octakis (methyl-9-carboxynonyldimethylsiloxy)-Q8-spherosilicate in reasonable yield and high selectivity yielding only the anti-Markovnikov adduct. The compound of Formula II(a) wherein R$^{4a}$, R$^{4b}$, R$^{4c}$, R$^{4d}$, R$^{4e}$, R$^{4f}$, R$^{4g}$, and R$^{4h}$ are each (CH$_2$)$_9$C(O)OCH$_3$ was recovered as an opaque, viscous oil which was suitable for use in enzymatic oligomerizations.

Scheme 4: The synthesis of octakis(methyl-9-carboxynonyldimethylsiloxy)-Q8-spherosilicate cube via platinum catalyzed hydrosilylation using Karstedt's Pt$^0$ 1,3-divinyl-1,1,3,3-tetramethyldisiloxane complex in xylenes.

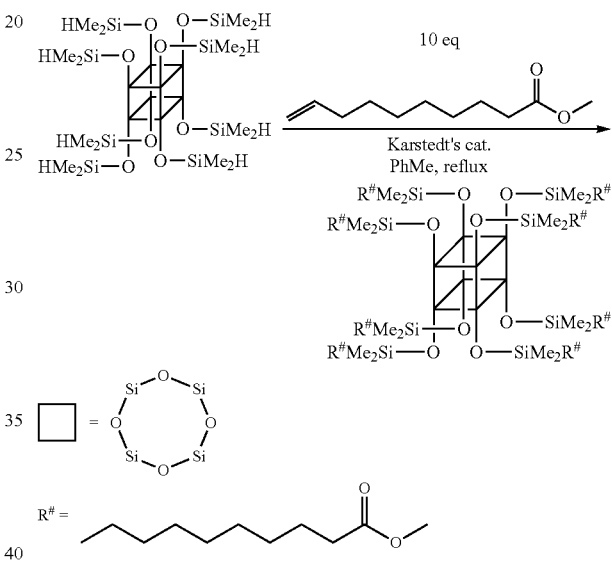

The use of enzymes has been studied for synthesizing polyesters and polyamides containing blocks of siloxane fragments. Through these studies it has become evident that the steric bulk imposed by the siloxane units can prove to be a challenge for a given enzyme catalyst. Increasing the steric bulk around silicon, from simple linear siloxanes to cyclotetrasiloxanes and the three dimensional architecture of a spherosilicate may therefore lead to potential issues related to enzyme-substrate incompatibility.

As reported herein, the oligomerization of C10-ester modified cyclotetrasiloxane of Formula I(a) wherein R$^{1a}$, R$^{1b}$, R$^{1c}$ and R$^{1d}$ are each (CH$_2$)$_4$C(O)OCH$_3$ by lipase B from Candida antarctica that had been immobilized on a cross linked methacrylate resin sold under the trade name Novozym-435 (N435) has been carried out. In the absence of solvent, short chain oligomers, and to a smaller extent polycyclic oligomers, were produced using N435 as the enzymatic catalyst. When the monomers were solvated in toluene, the equilibrium distribution of oligomeric species shifted away from linear oligomers to polycyclic oligomers with minor production of incompletely condensed oligomers.

The solvent-free oligomerization of the compound of Formula II(a) wherein R$^{4a}$, R$^{4b}$, R$^{4c}$, R$^{4d}$, R$^{4e}$, R$^{4f}$, R$^{4g}$, and R$^{4h}$ are each (CH$_2$)$_9$C(O)OCH$_3$ with octane-1,8-diol using N435 was attempted. While the monomers melted together at 100° C. to form a visually homogeneous mixture, the mixture itself was too viscous for the magnetic stir bar to adequately maintain its rotation.

The compound of Formula II(a) wherein $R^{4a}$, $R^{4b}$, $R^{4c}$, $R^{4d}$, $R^{4e}$, $R^{4f}$, $R^{4g}$ and $R^{4h}$ are each $(CH_2)_9C(O)OCH_3$ and the diol were then dissolved in toluene, and preheated to 100° C. prior to adding the enzyme catalyst to allow the enzymatic esterification of the compound of Formula II(a) wherein $R^{4a}$, $R^{4b}$, $R^{4c}$, $R^{4d}$, $R^{4e}$, $R^{4f}$, $R^{4g}$, and $R^{4h}$ are each $(CH_2)_9C(O)OCH_3$ and octane-1,8-diol (Scheme 5). The effect of temperature and enzyme loading were then studied.

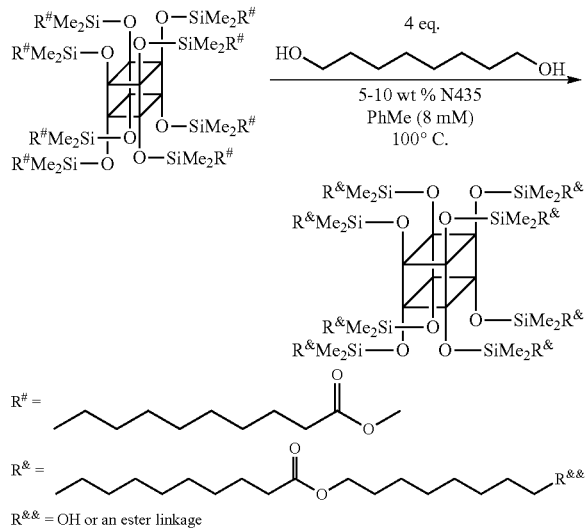

Scheme 5: The enzymatic modification of Q8 cubes using N435.

Over the course of a 24 h reaction cycle, the conversion of the methyl esters was 24.8% (n=5) at 70° C. and was only marginally increased to 26.2% (n=5) at 100° C. This trend was similar to that found during the enzymatic oligomerization of the cyclotetrasiloxane ester of Formula I(a) wherein $R^{1a}$, $R^{1b}$, $R^{1c}$ and $R^{1d}$ are each $(CH_2)_9C(O)OCH_3$ and octane-1,8-diol. Increasing the temperature to 130° C. resulted in the enzyme succumbing to thermal denaturation and only 7% transesterification was realized in 24 h.

Using the information gained from these temperature variation experiments, another study in which enzyme loading was varied was undertaken. At 100° C., an increase in the enzyme loading from 5 wt % to 10 wt % with respect to the total mass of the monomers afforded a nearly two-fold increase in the conversion of the methyl esters from 26.2% (n=5) to 48.0% (n=3) over 24 h.

The enzymatic modification of the compound of Formula II(a) wherein $R^{4a}$, $R^{4b}$, $R^{4c}$, $R^{4d}$, $R^{4e}$, $R^{4f}$, $R^{4g}$, and $R^{4h}$ are each $(CH_2)_9C(O)OCH_3$ was then performed over 120 h employing 5 wt % N435 at 100° C. During the enzymatic modification of the compound of Formula II(a) wherein $R^{4a}$, $R^{4b}$, $R^{4c}$, $R^{4d}$, $R^{4e}$, $R^{4f}$, $R^{4g}$, and $R^{4h}$ are each $(CH_2)_9C(O)OCH_3$, there are twenty five possible mass ions that can appear in a given MALDI-ToF MS spectrum.

Table 2 presents a list of possible oligomeric species (including the unmodified starting material) that may result from the N435-mediated modification of the compound of Formula II(a) wherein $R^{4a}$, $R^{4b}$, $R^{4c}$, $R^{4d}$, $R^{4e}$, $R^{4f}$, $R^{4g}$ and $R^{4h}$ are each $(CH_2)_9C(O)OCH_3$.

From the MALDI-ToF MS spectra there was no evidence for the stepwise addition between the compound of Formula II(a) wherein $R^{4a}$, $R^{4b}$, $R^{4c}$, $R^{4d}$, $R^{4e}$, $R^{4f}$, $R^{4g}$, and $R^{4h}$ are each $(CH_2)_9C(O)OCH_3$ and octane-1,8-diol units. Mass ions with a mass to charge ratio greater than 5000 m/z were not detected on any MALDI-ToF MS spectrum.

This is in contrast to the enzymatic oligomerization of linear aliphatic or siloxane-containing monomers, or cyclotetrasiloxane-containing esters which proceeds in a stepwise manner via multiple routes as discussed in Example 1. The oligomerization of a cyclotetrasiloxane-containing ester with octane-1,8-diol predominantly proceeds through a the step wise addition of octane-1,8-diol units (B unit) to the cyclic siloxane core, although this was not the case when a second D4 unit was appended to AB type dimers.

From the available MALDI-ToF MS data, the complete addition of octane-1,8-diol units to the core of the compound of Formula II(a) wherein $R^{4a}$, $R^{4b}$, $R^{4c}$, $R^{4d}$, $R^{4e}$, $R^{4f}$, $R^{4g}$, and $R^{4h}$ are each $(CH_2)_9C(O)OCH_3$ to give $AB_8$ was not evident. The mass ion data suggest that with each stepwise addition of a B unit, intramolecular esterification is as favourable an outcome as the addition of another B unit. While the mass ion for the ABcyc cube, expected at 2595 m/z, was absent, intramolecular esterification of B units was evident by the presence of mass ions at 2675 m/z and 2704 m/z which have been assigned as the $AB_2cyc^2$ and $AB_2cyc$ modified cubes. The addition of a third B unit gave rise to the $AB_3cyc^3$ and $AB_3cyc^2$ cubes, despite the lack of evidence for the $AB_3$ cube.

Dibutyltin dilaurate (DBTDL) is a common catalyst for the esterification and transesterification of acids/esters and diols. One of the drawbacks to using tin-based catalyst systems is the inherent toxicity of dialkyltin complexes. It was useful to do a comparison between N435 and dibutyltin dilaurate. A similar approach demonstrated the enhanced selectivity of N435 for the primary hydroxyl groups of glycerol over dibutyltin oxide, which was non selective, in polymerizing glycerol with oleic diacid.[61]

The compound of Formula II(a) wherein $R^{4a}$, $R^{4b}$, $R^{4c}$, $R^{4d}$, $R^{4e}$, $R^{4f}$, $R^{4g}$, and $R^{4h}$ are each $(CH_2)_9C(O)OCH_3$, octane-1,8-diol, and 1 wt % of DBTDL with respect to the mass of the monomers were combined and heated to 150° C. for 1 h. Within 20 minutes, the mixture was a solid cross-linked gel. The mixture was heated for an additional 40 minutes, cooled to room temperature and then diluted with 2 mL of tetrahydrofuran to remove the soluble fraction from the gel. The soluble fraction from the DBTDL cross-linked gels was made up primarily of lower order branched cubes such as AB, ABcyc, $AB_2$, $AB_2cyc$, $AB_3cyc$, and $AB_4cyc$; no incompletely condensed esters of the cube were found upon leaching from the cross linked gel. The insoluble gel was clear, colourless and soft to the touch and was not characterized further. The MALDI-ToF spectra for the soluble fraction of the DBTDL catalyzed reactions showed the presence of dimers containing multiple cube monomers. These cubes have been assigned as the $A_2B$ ($M+Na^+$=5088 m/z) and $A_2B_2$ ($M+Na^+$=5201 m/z) dimer. These species constitute only a very small proportion of all soluble cube species.

Thermal Tolerance

The thermal tolerance of the unmodified and enzymatically modified spherosilicate cubes was tested. A cleaned glass microscope slide was coated with a small amount of the cube and placed in an oven at 200° C. for 24 h. At the end of the incubation period the applied coating had not discoloured and there was no visual evidence for cracking of the coating.

Example 3

Formation of D4 Ester and Q8 Cube Films

I. Experimental

The addition of the methyl ester moiety to either the cyclic siloxane or the silsesquioxane core is achieved using a hydrosilylation reaction. The ester or amide functionality is subsequently installed using an immobilized lipase such as N435. Once functionalized, the compounds are applied to substrates as a thin film. The substrate may be, for example metal, glass or an organic substrate such as but not limited to cork, wood, paper or suitable plastics. The films are either physically applied to the substrate or covalently bonded to it.

II. Discussion

The combination of the cyclic siloxane or silsesquioxane and the long alkyl chains imparts hydrophobicity to the substrate. In both cases the alkyl chains also impart some degree of flexibility to the film. In the case of the silsesquioxane systems, the silicon-based cage also imparts strength to the film by behaving as a silica-like filler. As it is statistically unlikely that all of the reactive arms of the films will covalently bond with a surface, the films also possess reactive groups where further surface modification can occur. The coating therefore offers a thin film that can be readily tailored.

The esterified cyclic siloxane or silsequioxane can be used to impart hydrophobicity to the surface it is applied to resulting in minimal contact between the substrate surface and water/aqueous systems. As a result, these coatings can find application, for example in the automotive industry as an anti-corrosion coating, in the aerospace industry as a means of preventing/reducing the build-up of ice on the wings of aircraft and/or as a general water repellent. Applied to watercraft, the coating may, for example allow boats/ships to move through the water with greater ease and as a result, decrease fuel consumption.

Given the capacity of these thin films to encourage or retard the growth of biological molecules, coated substrates could be used in the culturing of various cell/tissue lines or as anti-fouling coatings.

The compounds may have other uses such as but not limited to photophysical applications, photocatalysis, drug delivery, low-k dielectrics, hydrogen storage and catalysis.

The thin films generated from the esterified cyclic siloxane or silsesquioxane are optically transparent which indicates the coatings are useful in applications where a cosmetic finish is required. In biological and chemical applications (glassware, culture plates, etc.) the transparent nature of the films permits the immobilization of biological samples and their subsequent analysis using optical techniques. As an anti-fouling coating the film could be applied to, for example, quartz covers for UV irradiators used in the treatment of sewage.

The coating is environmentally benign, as it is made up essentially of sand and lipids. In addition, the esterified cyclic siloxane or silsesquioxanes can be synthesized from readily available starting materials such as those obtained from triacylglycerides and the remnants of rice hull ash. The present coatings also contain ester moieties which may, for example, be biodegradable.

Many known thin film coatings are optically transparent in nature. However, one of the benefits of the present coatings which contain cyclic siloxane or silsesquioxane moieties is that not only are the coatings relatively flexible, but also self-reinforcing through the cyclic siloxane silsesquioxane moiety. For example, the eight reactive groups on the compounds containing silsesquioxane moieties provide not only a means of covalently linking the film to a substrate, but also a means through which further functionalization can be achieved. This represents a tunable material.

Example 4

Synthesis of Macrocyclic Oligo-Esters

The lipase-mediated synthesis of macrocyclic oligoesters that are derived from a cyclotetrasiloxane framework is described. The effect of three lipases, reaction temperature, substrate concentration, and the structure of the esters and diols on the formation of macrocyclic oligomers was examined. Three different cyclotetrasiloxane tetra esters ($C_5$, $C_7$ and $C_{10}$ chain lengths), two acyclic diols and a cyclic diol were studied. The behaviour of Langmuir monolayers and the thermal characteristics for the macrocyclic oligoesters were determined.

I. Materials and Instrumentation

Materials

Lipase B from *Candida antarctica* immobilized on Lewatit VP OC 1600 cross-linked divinyl benzene resin (Novozym-435®, N435), *C. antarctica* lipase A immobilized on Immobead 150, lipase from *Thermomyces lanuginosa*, lipase from *Rhizomucor meihei*, methyl 4-pentenoate, methyl 6-heptenoate, 9-decenoic acid, 1,3,5,7-tetramethylcyclotetrasiloxane, pentane-1,5-diol, (1R,2R)-trans-cyclohexane-1,2-diol, and Karstedt's platinum catalyst complex 2% in xylenes were obtained from Sigma-Aldrich (Oakville, Ontario, Canada). Octane-1,8-diol was obtained from Alpha Aesar (Ward Hill, N.J., USA). *Candida antarctica* lipase B recombinant from *Pichia pastoris* and stabilized with cyclodextrins was obtained from Chiral Vision (Leiden, The Netherlands). Deuterated chloroform ($CDCl_3$, 99.9% deuterated) was obtained from Cambridge Isotope Laboratories (Andover, Md., USA). Toluene, pentane and ethyl acetate were of a suitable grade and were stored over 4 Å molecular sieves before use.

Instrumentation

Nuclear magnetic resonance (NMR) spectra ($^1H$, $^{13}C$, $^{29}Si$) were recorded on a Bruker Avance AV-300 nuclear magnetic resonance spectrometer equipped with a BB-PABBO probe. $^1H$ and $^{13}C$ spectra were referenced to the residual protons of $CHCl_3$ in $CDCl_3$ (7.26 ppm) and $^{29}Si$ spectra were referenced to TMS (0.0 ppm). Fourier-transform infrared (FT-IR) spectra were obtained using a Mattson Research Series infrared spectrometer operating in transmission mode. Samples were prepared as thin films on KBr plates. Each spectrum consisted of 32 scans at 2 $cm^{-1}$ resolution. Electrospray ionization mass spectrometry (EI-MS) was carried out using a Kratos Concept 1S High Resolution E/B mass spectrometer in negative ion mode. Matrix Assisted Laser Desorption Ionization Time of Flight Mass Spectrometry (MALDI-ToF MS) spectra were acquired on a Bruker Autoflex MALDI-ToF mass spectrometer in the positive ion mode. Samples were dissolved into HPLC grade acetone, sonicated, and combined with a NaCl/THF (acetone) mixture and sonicated a second time. A small sample was transferred to a stainless steel plate that was preloaded with a paste composed of dithranol/THF.

Methods

Catalyst Choice.

Commercially available lipases were screened for the capacity to perform the transesterification of the $C_{10}D_4$ ester with octane-1,8-diol. The $C_{10}D_4$ ester and octane-1,8-diol were combined in a 1:2 stoichiometric ratio in toluene (50 mM) and melted to form a homogeneous mixture at 55° C. for 10 minutes. The enzymes, Candida antarctica lipase B on acrylic resin, C. antarctica lipase A immobilized on Immobead 150 (CALA), Rhizomucor meihei lipase (Lipozyme), Thermomyces lanuginosa lipase immobilized on Immobead 150 (TLL), and free C. antarctica lipase B mixed with cyclodextrins (CV-CALBY, Chiral Vision), were added at 5 wt % with respect to the total mass of the monomers. The reactions were stopped after 24 h and analyzed by $^1H$ NMR to determine total conversion. The total conversion was expressed on a per unit basis to standardize the total conversion. The molecular mass of the components within the unfractionated polymers were determined using MALDI-ToF MS.

II. Reactions

Synthesis of methyl-9-decenoate

To a stirred solution of 9-decenoic acid (1.83 g, 10.8 mmol) in methanol (10.0 mL) was added 115.0 mg (6.05×$10^{-4}$ mol) of p-TsOH. The mixture was heated to reflux for 4 h. Methanol was removed in vacuo and the crude residue was extracted into 20.0 mL diethyl ether and washed with 10.0 mL of 1M $KHCO_3$, 10.0 mL brine and subsequently dried over $Na_2SO_4$. Ether was removed in vacuo to yield 1.78 g (9.65 mmol, 90%) of a clear, colourless oil. $^1H$ NMR ($CDCl_3$, 300 MHz): δ 1.30 (s), 1.38 (m), 2.03 (m), 2.30 (t, J=7.5 Hz), 3.66 (s), 4.91 (m), 4.95 (m), 5.01 (m), 5.80 (m); $^{13}C$ NMR ($CDCl_3$, 75 MHz): δ 24.9, 28.8, 28.9, 29.1, 33.7, 34.1, 51.4, 114.2, 139.1, 174.3; EI-MS (m/z): $M^+$ 184. FTIR (KBr, $cm^{-1}$): 1436, 1641, 1742, 2855, 2928, 2976, 3076.

Preparation of 1,3,5,7-tetrakis(4-carboxybutyl)-1,3,5,7-tetramethylcyclotetrasiloxane tetramethyl ester The synthesis of 1,3,5,7-tetrakis(4-carboxybutyl)-1,3,5,7-tetramethylcyclotetrasiloxane tetramethyl ester was carried out as previously reported. Briefly, methyl 4-pentenoate (793.0 mg, 800 µL, 6.2×$10^{-3}$ mol) was dissolved in toluene (10 mL). To this was added 20 µL of Karstedt's platinum catalyst complex (2% in xylenes) and the mixture was stirred at room temperature for 5 min. To this mixture were added 337.0 mg (340 µL, 1.4×$10^{-3}$ mol) of 1,3,5,7-tetramethylcyclotetrasiloxane drop-wise over 10 min, after which time the reaction flask was heated to reflux temperature on a heating mantle and variac for 2.5 h. The cooled contents of the reaction mixture were diluted with a 10 mL volume of toluene and decolorized with activated carbon for 18 h. The activated carbon was removed by filtering the reaction mixture through Celite using a medium porosity Büchner funnel. The crude product was purified by flash column chromatography on silica gel using pentane:ethyl acetate increasing the polarity from 10% to 50% ethyl acetate as the elution solvent to yield 777.0 mg (1.02×$10^{-3}$ mol, 73%) of a clear oil. $^1H$ NMR (300 MHz, $CDCl_3$): δ 0.06 (s, 12H), 0.52 (m, 8H), 1.37 (m, 8H), 1.6 (m, 8H), 2.30 (t, 8H, $^3J$=6 Hz), 3.66 (s, 12H); $^{13}C$ NMR (75 MHz, $CDCl_3$): δ −0.7, 16.8, 22.6, 28.2, 33.8, 51.4, 174.2; $^{29}Si$ NMR (59.6 MHz, $CDCl_3$): δ −20.2; EI-MS (m/z): $M^+$ 696; FTIR (KBr, 2 $cm^{-1}$): 748, 800, 1075, 1199, 1260, 1437, 1741, 2862, 2875, 2933, 2952.

Preparation of 1,3,5,7-tetrakis(6-carboxyhexyl)-1,3,5,7-tetramethylcyclotetrasiloxane tetramethyl ester The synthesis of 1,3,5,7-tetrakis(6-carboxyhexyl)-1,3,5,7-tetramethylcyclotetrasiloxane tetramethyl ester was performed as previously reported.[62] To a stirred solution of methyl 6-hexenoate (590.9 mg, 650 µL, 4.16×$10^{-3}$ mol) in 10 mL of toluene were added 20 µL of Karstedt's platinum catalyst in xylenes. This mixture was stirred at room temperature for approximately 5 minutes, when 218.0 mg (220 µL, 9.08×$10^{-4}$ mol) of 1,3,5,7-tetramethylcyclotetrasiloxane were added over 10 min in a drop-wise fashion. The reaction flask was heated to reflux with the aid of a heating mantle for 18 h. The cooled reaction mixture was decolorized with activated carbon in toluene for 2 h. The decolorizing agent was removed by filtration through Celite and the reaction product was purified by column chromatography on silica gel and eluted with pentane:ethyl acetate increasing the polarity from 5% to 50% ethyl acetate to yield 595.5 mg (7.36×$10^{-4}$ mol, 81%) of a colourless oil. $^1H$ NMR (300 MHz, $CDCl_3$): δ 0.05 (s, 12H), 0.50 (m, 8H), 1.31 (br, 24H), 1.61 (m, 8H), 2.30 (t, 8H, $^3J$=9 Hz), 3.66 (s, 12H); $^{13}C$ NMR (75 MHz, $CDCl_3$): δ −0.6, 17.5, 22.8, 24.9, 29.0, 32.8, 34.1, 51.4, 174.2; $^{29}Si$ NMR (59.6 MHz, $CDCl_3$): δ −20.2, −20.3; EI-MS (m/z): $(M-CH_3)^+$ 793; FTIR (KBr, 2 $cm^{-1}$): 800, 1072, 1176, 1194, 1259, 1436, 1742, 2857, 2924.

Preparation of 1,3,5,7-tetrakis(9-carboxynonyl)-1,3,5,7-tetramethylcyclotetrasiloxane tetramethyl ester The synthesis of 1,3,5,7-tetrakis(9-carboxynonyl)-1,3,5,7-tetramethylcyclotetrasiloxane tetramethyl ester was performed as previously described.[62] To a stirred solution of methyl 9-decenoate (1.369 g, 1.6 mL, 7.43×$10^{-3}$ mol) dissolved in 10 mL of toluene were added 10 µL of Karstedt's platinum catalyst in xylenes. The reaction mixture was stirred at room temperature for approximately 5 min to allow for complexation of the platinum catalyst with the alkene. To this were added 396.4 mg (400 µL, 1.65×$10^{-3}$ mol) of 1,3,5,7-tetramethylcyclotetrasiloxane after which time the reaction flask and its contents were heated to reflux for 2 h. The cooled reaction mixture was diluted with toluene, and decolourized with activated carbon for 18 h. The activated carbon was removed by filtering and the crude reaction product was purified by flash column chromatography on silica gel and eluted with pentane:ethyl acetate increasing the polarity from 10% to 33% ethyl acetate to yield 931.5 mg (9.54×$10^{-4}$ mol, 58%) of a clear, straw-coloured oil. $^1H$ NMR (300 MHz, $CDCl_3$): δ 0.05 (s, 12H), 0.50 (m, 8H), 1.27 (br, 48H), 1.61 (m, 8H), 2.30 (t, 8H, $^3J$=6 Hz), 3.66 (s, 12H); $^{13}C$ NMR (75 MHz, $CDCl_3$): δ −0.6, 17.2, 23.0, 25.0, 29.2, 29.3, 29.41, 29.43, 33.2, 34.1, 51.4, 174.5; $^{29}Si$ NMR (59.6 MHz, $CDCl_3$): δ −20.2; EI-MS (m/z): $(M-CH_3)^+$ 961; FTIR (KBr, 2 $cm^{-1}$): 800, 1071, 1086, 1172, 1196, 1258, 1436, 1462, 1745, 2855, 2927.

Synthesis of Macrocyclic Oligo Esters

A typical procedure for the synthesis of $C10D_4$-derived oligoesters was as follows. A 10 mL round bottomed flask was charged with 171.1 mg (1.75×$10^{-4}$ mol) of the $C10D_4$ ester and 52.2 mg (3.53×$10^{-4}$ mol) of octane-1,8-diol and melted at 100° C. to form a homogeneous mixture. The mixture of monomers was diluted to either 5, 10, 20, 25, or 50 mM with toluene. Novozym 435® (N435®) was then added to the reaction mixture and stirred for 120 h. The reaction was terminated by the addition of 10 mL of CHCl₃ and stirred for a further 10 min. The enzyme catalyst was removed by filtering the reaction mixture through a medium porosity glass fritted Buchner funnel; the beads were subsequently rinsed with two 5 mL volumes of chloroform and the excess solvent was removed in vacuo.

Langmuir Isotherms

Langmuir isotherms were performed using a KSV NIMA Minitrough (50 mm×155 mm) and Delrin barriers in a vibration-free environment. Barrier control and data acquisition were achieved using the LB measurement system provided by KSV NIMA (Biolin Scientific, Linthicum Heights, Md. USA). The Wilhelmy balance was calibrated using a 264.9 mg calibration standard provided by the manufacturer prior to data acquisition. The surface pressure isotherms were measured using pre-wetted paper Wilhelmy plates at a temperature of 21.5° C. that was controlled by a circulating water chiller. Ultrapure MilliQ water (18.2 MO at 25° C.) was used as the subphase. The subphase surface pressure was maintained below 0.1 mN/m prior to the application of the film; when the pressure of the subphase exceeded 0.1 mN/m, the surface was re-cleaned and the procedure was repeated. Langmuir monlayers were spread using 6 µL of 1 mg/ml chloroform solutions. Data acquisition commenced after a 10 min waiting period to allow for solvent evaporation prior to compression-decompression cycling. The barriers were compressed/decompressed at a rate of 5 mm/min; at least three cycles of the compression/expansion were performed. Between experiments the trough and barriers were thoroughly cleaned using chloroform and water for the Teflon Langmuir trough, and ethanol and water for the Delrin barriers.

Differential Scanning Calorimetry (DSC)

DSC thermograms were acquired using a Shimadzu DSC-60 and a TA-60WS Thermal Analyzer. Aluminum pans were used for acquiring each thermogram; an empty pan was used as the control to which samples were compared. Samples were subjected to two heating and cooling cycles so that each sample had the same thermal memory. Samples were cooled to −150° C. from room temperature. Samples were heated at a rate of 10° C./min to 30° C., cooled at −10° C./m to −150° C.; this was done twice. Thermal transitions were taken from either the second heating or cooling cycle.

III. Results and Discussion

Solvent Choice

Lipases are renowned for the capacity to function at lipid water interfaces, as well as in neat organic solvents. Several organic solvents, spanning a range of partition coefficient (log P) values, were screened as potential solvents for synthesizing macrocyclic oligoesters. The log P values were taken from Laane et al.[63] except those for 2,2,4-trimethyl-pentane (log P=4.5), which was taken from Hailing,[64] and octamethylcyclotetrasiloxane (log P=5.1), which was taken from Luu and Hutter.[65] Tetrahydrofuran, toluene, hexanes, 2,2,4-trimethylpentane (isooctane) and octamethylcyclo-tetrasiloxane were tested as reaction media for the synthesis of cyclotetrasiloxane-derived macrocyclic oligoesters at an initial concentration of 50 mM using 5 wt % of N435 at 60° C. (Scheme 6). This temperature was chosen as it was below the boiling point of the lowest boiling solvent, negating the need to deal with refluxing solvents, but allowed for the melting of octane-1,8-diol. After 24 h, the solvents that appeared to be the most beneficial to the enzymatic process were hexanes (log P=3.5) and toluene (log P=2.5). In these two solvents, N435 reached 58% total conversion of the methyl esters (Table 3). Previous studies have also identified toluene as a good solvent for ester formation using enzymatic catalysis.[66,67]

Scheme 6

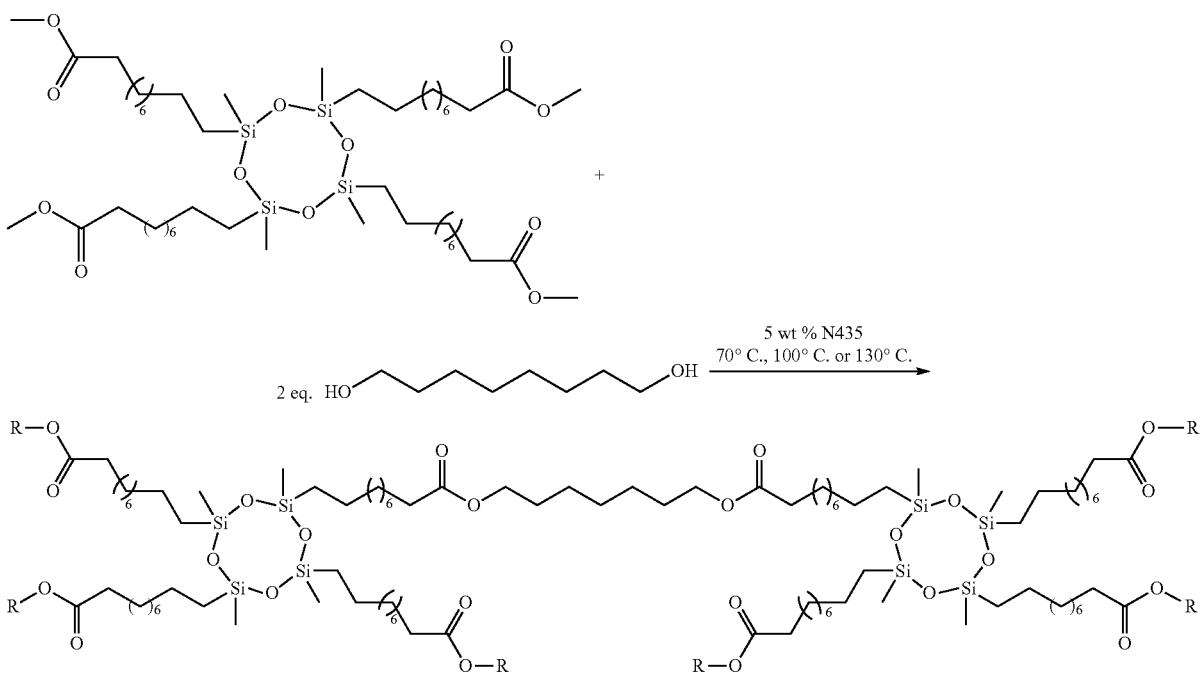

Enzymes

Several immobilized fungal lipases were screened for their capacity to synthesize macrocyclic oligoesters from octane-1,8-diol and the $C_{10}D_4$ core at 60° C. over the course of 24 h in toluene (50 mM). N435 was a suitable enzyme choice, which converted 58% of the free methyl esters in the allotted time, and was chosen to serve as a platform to optimize further reaction conditions.

Substrate Concentration

At a concentration of 50 mM using 5 wt % of N435 for 120 h, conversion of the methyl esters was 95% (as determined by $^1$H NMR). The MALDI-ToF MS spectrum indicated ion peaks corresponding to $AB_2cyc^2$ ((M+Na)$^+$=1,166 m/z) (4) and $A_2B_4cyc^3$ ((M+Na)$^+$=2,307 m/z) (5) with some lower intensity peaks that indicated incompletely cyclized oligomeric species. The structures of these two macrocycles are presented in Scheme 7.

Figure 6:
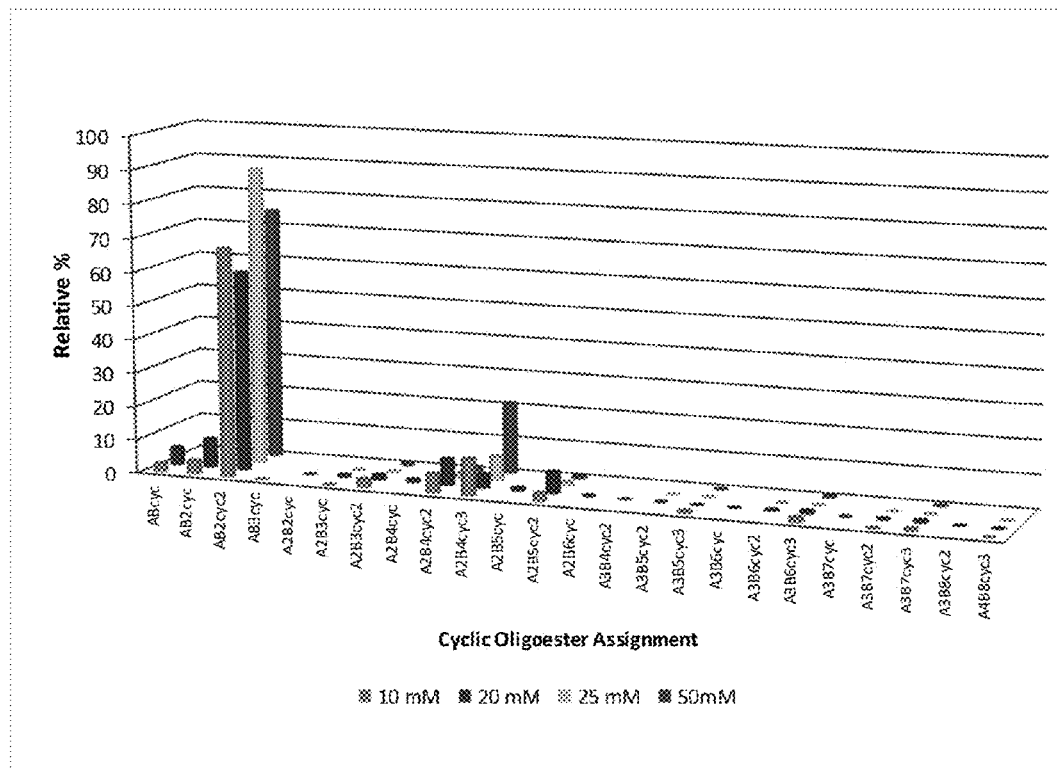
FIG. 6 is a graphical representation of the distribution of acyclic and cyclic oligoesters at different concentrations in toluene as determined by MALDI-ToF-MS.

The mass ion of greatest intensity was the $AB_2cyc^2$ macrocycle; the intensity of the ion for the $A_2B_4cyc^3$ macrocycle varied between 20-38% with respect to the base peak. However, at this concentration, the presence of incompletely cyclized monomers was not totally suppressed. A graphical representation of the identity of each species, and the relative proportion of each species, is presented in FIG. 6. Reducing the concentration further to 25 mM gave similar conversion of the methyl esters at 90-95%. Again, the two dominant macrocycles were the $AB_2cyc^2$ (100% intensity in the MALDI-ToF MS) and $A_2B_4cyc^3$ (5-13% intensity in the MALDI-ToF MS), with some evidence for incompletely condensed species. Reducing the monomer concentration further to 20 mM and then 10 mM afforded greater than 85% conversion of the $C10D_4$ ester functional groups with a similar distribution of products. At concentrations below 25

Scheme 7

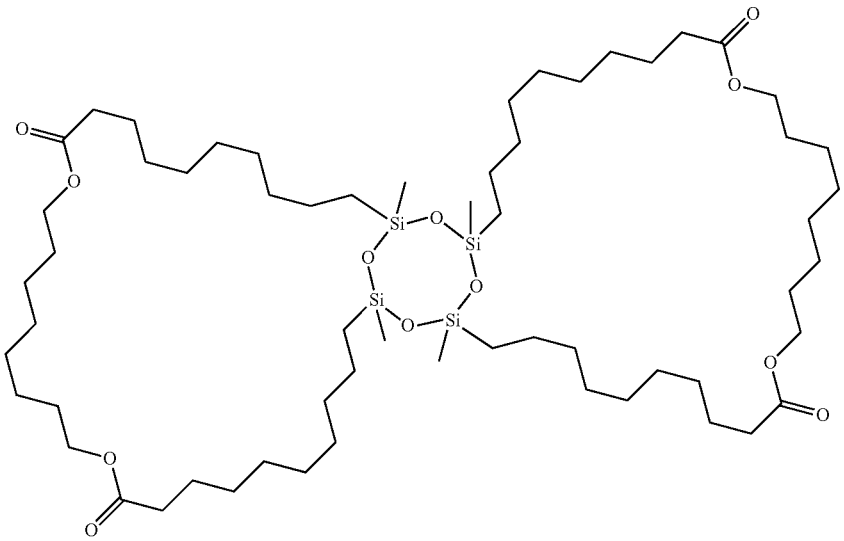

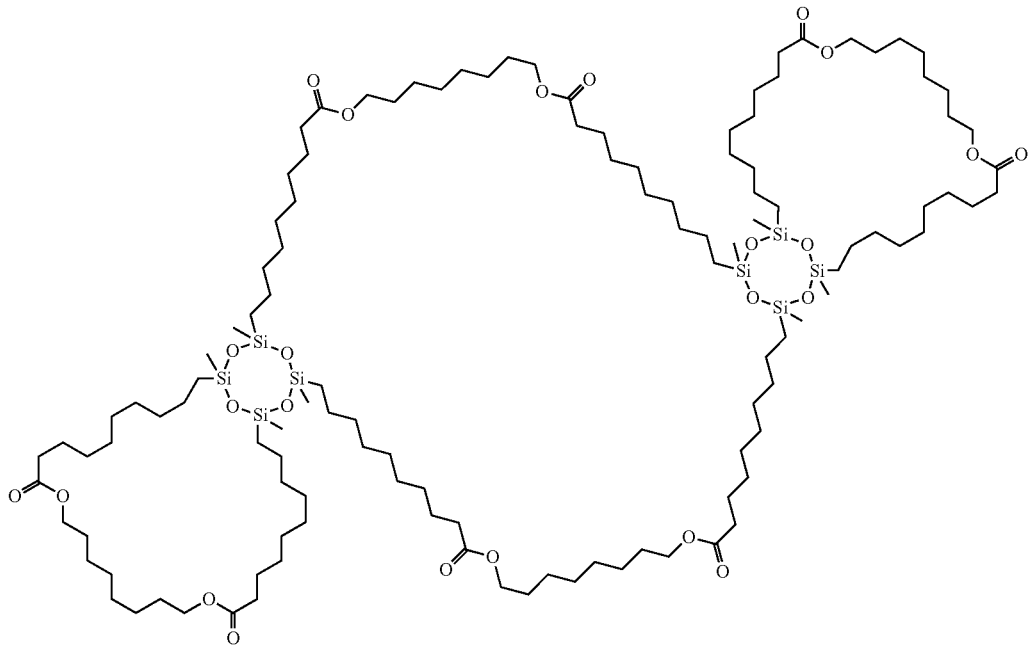

mM it became apparent, by examination of the $^1$H NMR spectra, that the acrylic resin on which the CalB molecule was immobilized had started to degrade. The degradation of the acrylic substrate matrix has also been seen by Poojari et al (Y. Poojari, J. S. Beemat, and S. J. Clarson. Polym. Bull., 2013, 70, 1543-1552). The degradation of the acrylic matrix was more prevalent at 5 mM where only 50% conversion of the monomers was attained after 120 h. As a result of these observations a concentration of 25 mM was chosen for all future experiments to maximize product formation and to suppress the degradation of the N435 beads.

Temperature

Figure 7:
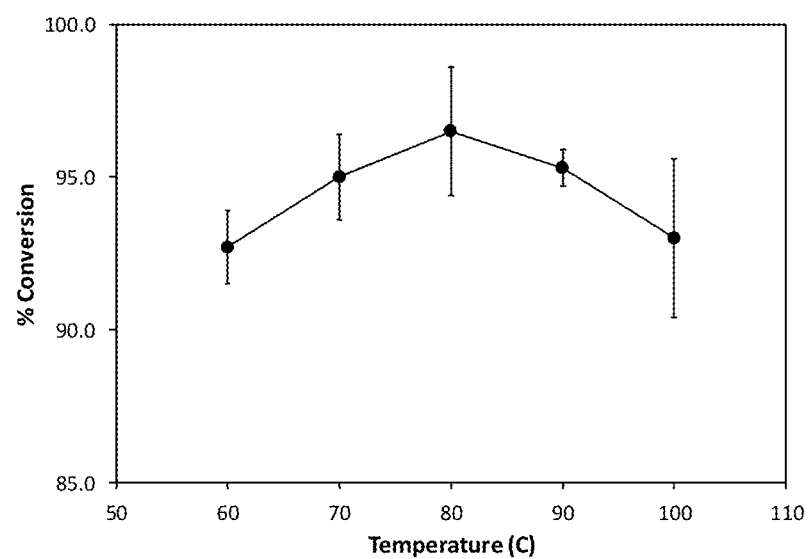
FIG. 7 is a graph showing the conversion of $C_{10}D_4$ ester as a function of temperature.
Figure 8:
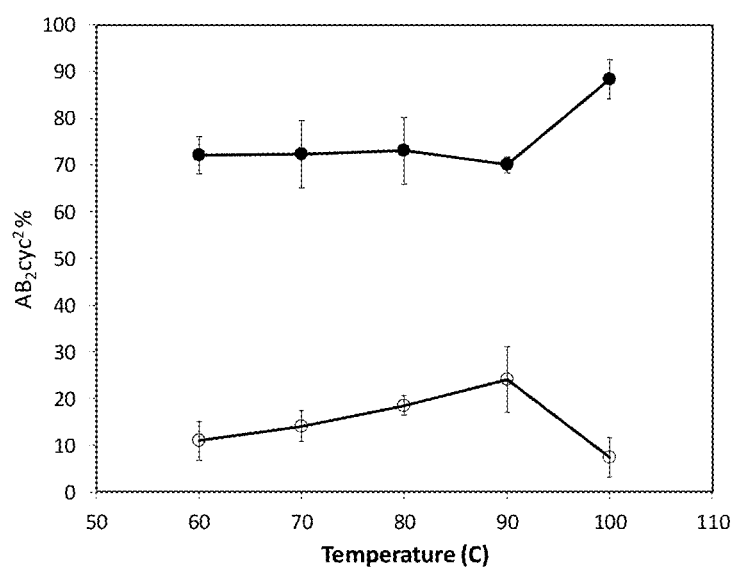
FIG. 8 is a graph showing the amount of $AB_2cyc^2$ and $A_2B_4cyc^3$ produced at each of the surveyed reaction temperatures as determined by MALDI-ToF MS.

Temperature is known to play an important role in regulating enzymatic activity. However, in some systems the choice of monomers can dictate the optimal and maximum temperatures that allow the enzyme to retain catalytic activity. In some cases, this range can be well above the physiological maximum for any given enzyme. For instance, previous reports suggested that 70° C.-90° C. was an optimal temperature range for ester-based mediated by lipases polymerizations.[68-73] However, the addition of siloxane containing monomers imparted thermal stability to the enzyme allowing transformations to be carried out at 130° C. with only a minor loss in residual activity (M. B. Frampton and P. M. Zelisko. Chem. Commun., 2013, 49, 9269-9271; M. B. Frampton, J. P. Seguin, D. Marquardt, T. A. Harroun, and P. M. Zelisko. J. Mol. Cat. B: Enz., 2013, 85-86, 149-155; M. B. Frampton and P. M. Zelisko. Enz. Microbiol. Technol., 2014, 58-59, 87-92). In order to determine the optimal temperature for maximizing conversion and yield of the macrocyclic oligoesters, reactions were carried out from 60-100° C. for 120 h. Temperature did not significantly impact the reaction in the range that was tested. At every temperature in which the reaction was carried out, conversion was high, ranging from an average of 93% at 60° C. to a high of 96% at 80° C. (FIG. 7). More importantly, the observed distribution of macrocyclic oligoesters favoured the formation of the $AB_2cyc^2$ macrocycle with clear evidence for the macrocycle $A_2B_4cyc^3$. The $AB_2cyc^2$ macrocycle consistently accounted for 70-73% of the reaction mixture, while the proportion of the $A_2B_4cyc^3$ oligoester was found in 10-25% (FIG. 8). At 100° C. the distribution of the observed products changed such that the proportion of $AB_2cyc^2$ increased dramatically to 88% resulting in a concomitant reduction in the amount of the $A_2B_4cyc^3$ oligoester to 7%.

Figure 9:
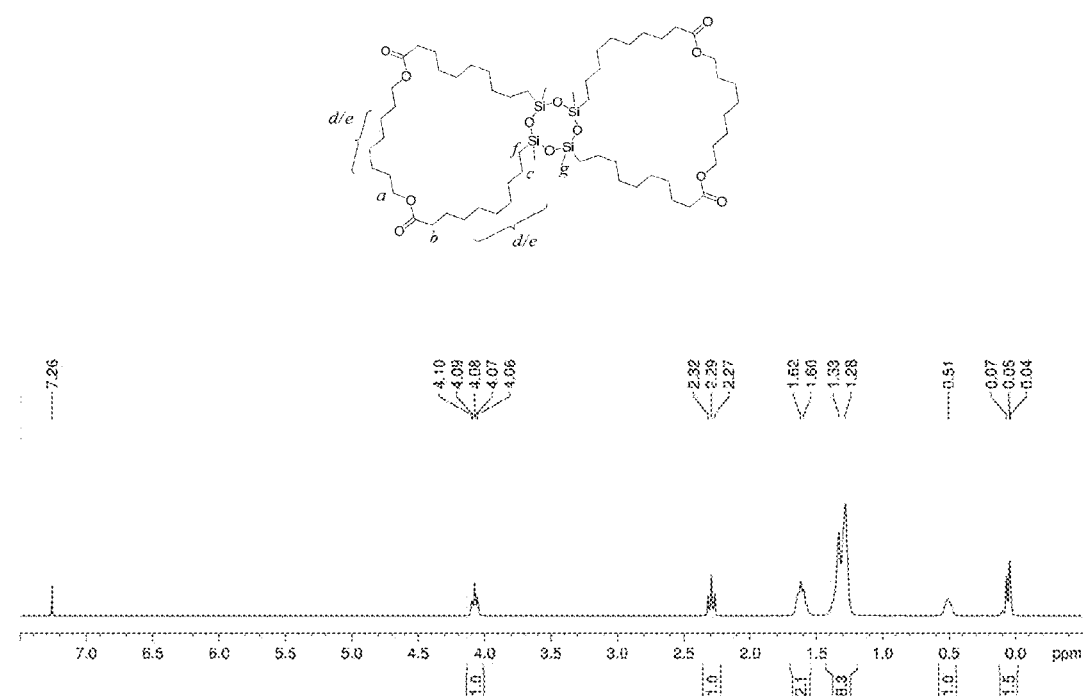
FIG. 9 shows the $^1H$ NMR spectrum for the $C_{10}D_4$-derived $AB_2cyc^2$ oligoester.

The $C_{10}D_4$-derived $AB_2cyc^2$ oligoester was isolated by column chromatography in yields of 17-30% using 15% ethyl acetate in hexanes as the eluent. The $^1$HNMR spectrum is presented in FIG. 9. The $^1$HNMR spectrum indicated the presence of a single compound, the $AB_2cyc^2$ macrocyclic oligo ester. This was confirmed by both MALDI-ToF and ESI-MS which showed a molecular ion peak corresponding to (M+Na)$^+$ at 1,164 m/z (MALDI-ToF MS) and 1,141 m/z (ESI-MS).

Ester Structure

N435 has been shown to have a broad substrate tolerance. The effect of ester chain length on the enzymatic synthesis of macrocyclic oligoesters was taken into consideration. In addition to the $C10D_4$ ester, two additional esters, $C5D_4$ and $C7D_4$, were synthesized and examined as substrates as described in Table 4.

Diol Structure

Diol structure is known to affect the growth of the molecular mass in polyesters. Increasing the chain length of the diol favoured the formation of higher molecular weight polyesters (H. M. Luu and J. C. Flutter. Environ. Health Perspect., 2001, 109, 1095-1101). A change in the chain length of the diol from octane-1,8-diol to pentane-1,5-diol had little change on the average conversion after 120 h when the $C_{10}D_4$ ester was the acyl donor. The proportion of the $AB_2cyc^2$ macrocycle was found at similar levels of 82% compared to 88% for octane-1,8-diol (Table 4). A change in the geometry of the diol to the cyclic diol trans-(1R,2R)-cyclohexane-1,2-diol, elicited a pronounced effect on the outcome of the reaction. Firstly, after five days in solution it was clear the geometry of the cyclic 1,2-diol was less conducive to the enzymatic esterification as only 43% conversion was acquired and an absence of cyclic oligoesters was observed.

Langmuir Isotherms

Figure 10:
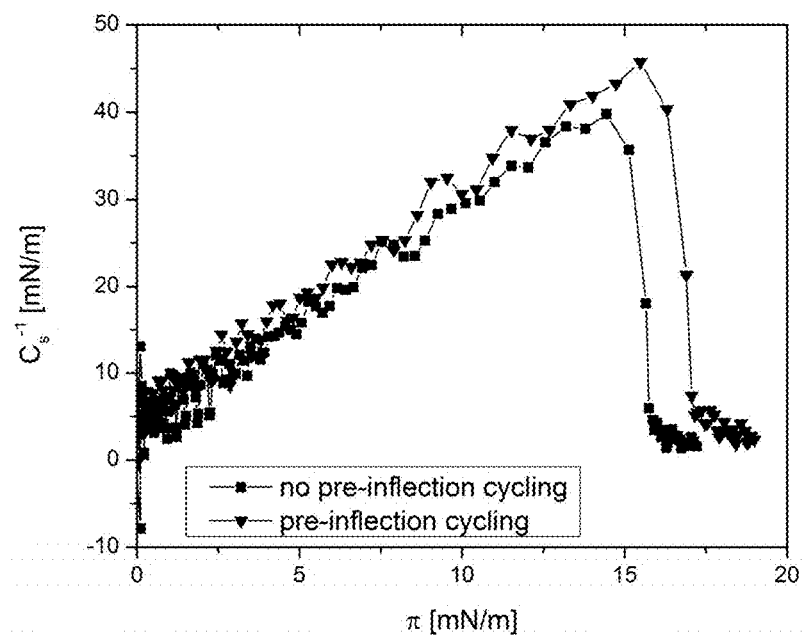
FIG. 10 is a graph showing the compression modulus $(C_s^{-1})$ as a function of surface pressure ($\pi$) for the $AB_2cyc^2$ oligoester following pre-inflection cycling $C_s^{-1}$ increases.

Insoluble Langmuir monolayers were deposited onto an aqueous subphase to determine the film properties at the air-water interface. Two-barrier compression was carried out at a rate of 5 mm/min and the subphase temperature was held constant at 21.5° C. Surface pressure ($\pi$)-area (A) isotherms ($\pi$-A) were collected and are shown in FIG. 10. Three consecutive compression-expansion cycles were carried out with little change in the overall shape of the isotherms. Compression of the Langmuir film exhibited the expected behavior. The $\pi$ started to increase at a mean molecular area of ~200 Å$^2$ and steadily increased until a critical point ($\pi_c$) was reached at $\pi_c$=15.3±1.0 mM/m at approximately 78 Å$^2$. The observed inflection point, where monolayer collapse occurred, possessed a different line shape than expected for long alkyl fatty acids, for example stearic acid, which has a reported $\pi$=55 mN/m.[74] Collapse of the Langmuir film appeared to be a much different process than that observed for monolayer collapse of fatty acid films, which tend to exhibit large decreases in IF after the critical point is reached. The expansion of the barriers was performed at the same rate as the compression cycles. During the expansion, the observed inflection point was found to be slightly lower at 13.5±0.7 mN/m indicating only a marginal hysteresis in the films. Similar behavior has been observed during the reversible collapse of triphenylsilyl ether-terminated amphiphiles.[75] Monomeric liquid crystals based on a siloxane framework tend to show a much greater degree hysteresis upon decompression.[76] The reversible, collapsible nature of the Langmuir monolayer has been seen previously in amphiphilic silyl ether films and benzo[A]phenanthrene ether monolayers.[75,77]

Figure 11:
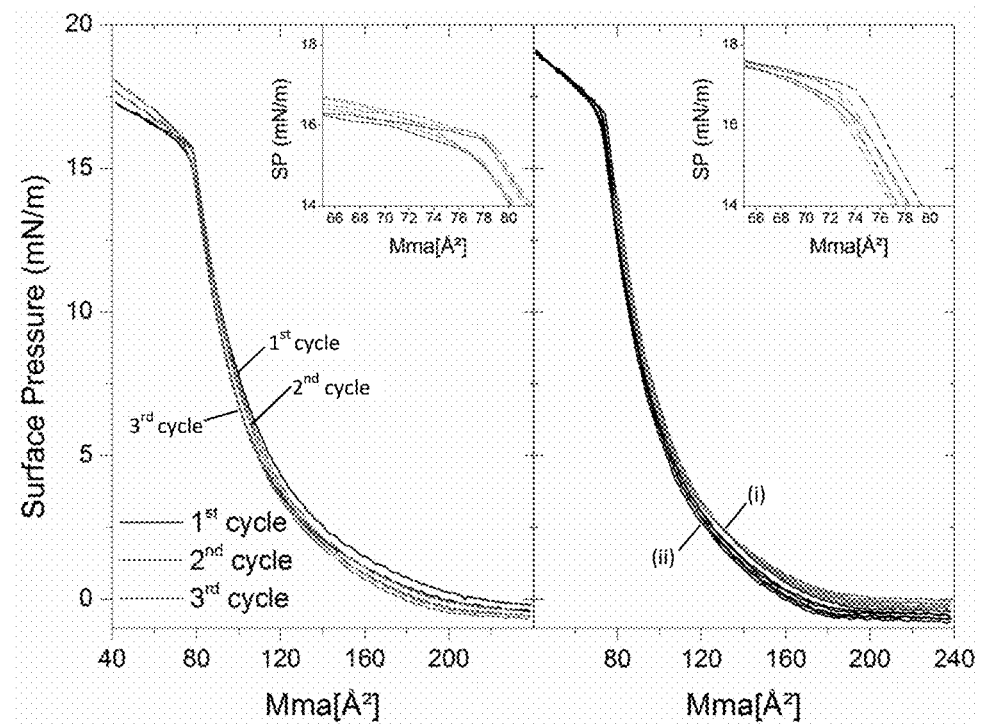
FIG. 11 is a graph showing Langmuir π-A isotherms for a $AB_2cyc^2$ macrocyclic oligoester monolayer: (A) three successive compression-decompression cycles. The inset is an expanded isotherm indicating the SP at which monolayer collapse occurs; (B) three pre-compression-decompression cycles (labelled (i)) which were followed by subsequent complete compression-decompression cycles (labelled (ii)). The inset indicates that monolayer collapse at higher SP following pre-compression-decompression cycling.

Three compression cycles were performed and stopped prior to reaching the inflection point at $\pi_c$=15.3±1.0 mM/m to determine the effect of compressing the monolayer on future phase transitions. The right panel of FIG. 11 shows that pre-compression cycles lead to an increase in $\pi_c$ to 17 mN/m at 74 Å$^2$.

To further investigate the nature and location of the phase transitions in the Langmuir film, the compression modulus ($C_s^{-1}$) was plotted against $\pi$ (see FIG. 10). The phase transitions of the Langmuir films are divided based on the maximum values of $C_s^{-1}$. These phases have been previously defined as: $C_s^{-1}$<12.5 mN/m, gaseous; $C_s^{-1}$=12.5-50 mN/m, liquid expanded; $C_s^{-1}$=50-100 mN/m, liquid; $C_s^{-1}$=100-250 mN/m, liquid condensed; $C_s^{-1}$=250-1000 mN/m, condensed; and $C_s^{-1}$=>1000 mN/m, solid (Kepczynski, J. Bednar, D. Kuźmicz, D. Wydro, and M. Nowokaska. Langmuir, 2010, 26, 1551-1556).

In the $C_s^{-1}$ versus $\pi$ plots for the Langmuir monolayer, the maximum value that was obtained was $(C_s^{-1})_{max}$=39.8 mN/m when $\pi$=14.4 mN/m. The presence of a single maximum occurring below 50 mN/m indicated that the monolayer remained in the liquid expanded phase. We sought to determine the effect of multiple compressions on these values by preparing a sample and compressing the Langmuir film to a π-value below the inflection point to approximately π=14 mN/m. After the pre-inflection compressions, the maximum $C_s^{-1}$ value increased to $(C_s^{-1})_{max}$=45.7 mN/m when π=15.5 mN/m, suggesting that the monolayer remained in the liquid expanded phase after multiple pre-compressions of the film.

Thermal Properties

Figure 12:
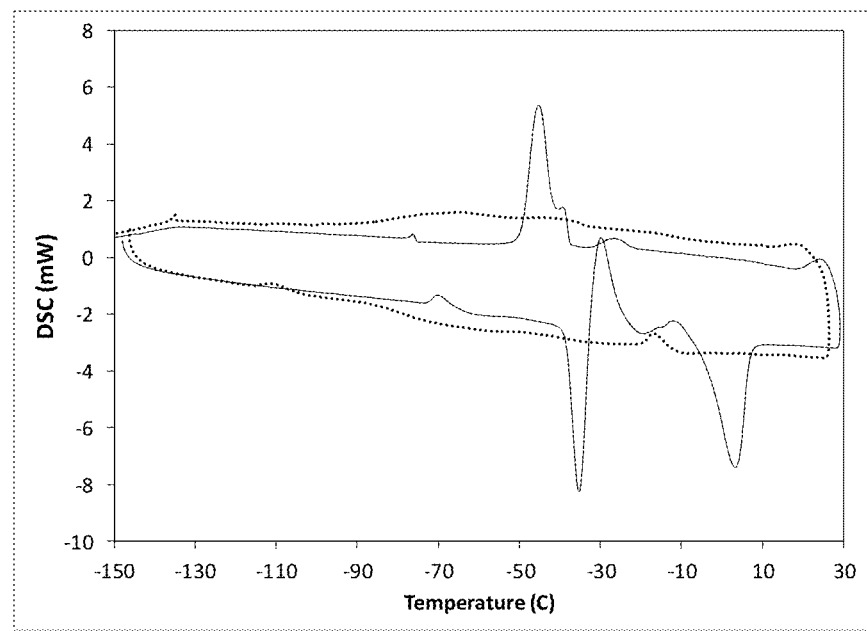
FIG. 12 is shows DSC thermograms of the $AB_2cyc^2$ macrocyclic oligoester from $C_{10}D_4$ (dotted line) and the $C_{10}D_4$ core scaffold (solid line).

DSC thermograms were acquired for the $C10D_4$ ester and the $AB_2cyc^2$ derivative as shown in FIG. 12. Each sample was heated from −150° C. to 30° C. at 10° C./min to give both samples the same thermal memory. The DSC thermogram for the $C10D_4$ ester displayed many features of interest; firstly there is $T_m$ at −35° C. which is closely followed by a second $T_m$ at 2.3° C. for the melting of the alkyl ester chains. Upon cooling, there is an observable hysteresis in the freezing-melting transition. Crystallization was seen to occur as a two stage process at $T_{c1}$ −38° C. and $T_{c2}$ −45° C. These thermal transitions all but disappeared in the $AB_2cyc^2$ macrocycle. The only observable transitions in the DSC spectrum occur at −90° C., and were very broad. These inflections likely represent the transition from a glassy to an amorphous state of the macrocycle. While the present application has been described with reference to what are presently considered to be the preferred examples, it is to be understood that the application is not limited to the disclosed examples. To the contrary, the present application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE SPECIFICATION

[1] P. J. Flory. *J. Am. Chem. Soc.*, 1952, 74, 2718-2723.
[2] C. Gao, and D. Yan., *Prog. Polym. Sci.*, 2004, 29, 183.
[3] A. S. Kulshrestha, W. Gao, and R. A. Gross. *Macromolecules*, 2005, 38, 3193-3204.
[4] C. J. Hawker, R. Lee, and J. M. J. Frechet. *J. Am. Chem. Soc.*, 1991, 113, 4583-4588.
[5] C. J. Hawker and J. M. J. Frechet. *J. Am. Chem. Soc.*, 1990, 112, 7638-7647.
[6] J. F. Stumbé and B. Bruchmann. *Macromol. Rapid Commun.*, 2004, 25, 921-924.
[7] D. H. Guimares, M. de Meireles Brioude, R. Da Paz Fuiza, L. A. Sanchez de Almeida Prado, J. S. Boaventura, and N. M. Jose. *Mat. Res.*, 2007, 10, 257-260.
[8] Y. Yang, W. Lu, J. Cai, Y. Hou, S. Ouyang, W. Xie, and R. A. Gross. *Macromolecules*, 2011, 44, 1977-1985.
[9] S. Skaria, M. Smet, and H. Frey. *Macromol. Rapid Commun.*, 2002, 23, 292-296.
[10] Y. Z. Zhankg, S. Spinella, W. Xie, J. Cai, Y. Yang, Y. Z. Wang, and R. A. Gross. *Eur. Polym. J.*, 2013, 49, 793-803.
[11] M. A. Brook. *Silicon in Organic, Organometallic, and Polymer Chemistry*. Wiley, New York, N.Y., USA. 2000.
[12] M. J. Owen. Siloxane Surface Activity. In J. M. Zeigler and F. W. G. Feardon (Eds.) *Silicon-Based Polymer Science, A Comprehensive Resource*. American Chemical Society, Washington, D.C., USA. 1990.
[13] J. W. White and R. C. Treadgold, Organofunctional Siloxanes. In S. J. Clarson and J. A. Semlyen (Eds.), *Siloxane Polymers*. Prentice Hall, Englewood Cliffs, N.J., USA. 1993.
[14] D. R. Thomas, Cross-Linking of Polydimethylsiloxanes. In S. J. Clarson and J. A. Semlyen (Eds.), *Siloxane Polymers*. Prentice Hall, Englewood Cliffs, N.J., USA. 1993.
[15] M. Jang and Crivello. *J. Polym. Sci. Part A: Polym. Chem.*, 2003, 41, 3056-3073.
[16] A. Saxena, S. Rajaraman, and M. Leatherman. *Macromolecules*, 2007, 40, 752-755.
[17] J. B. Grande, D. B. Thompson, F. Gonzaga, and M. A. Brook. *Chem. Commun.*, 2010, 46, 4988-4990.
[18] J. B. Grande, F. Gonzaga, and M. A. Brook. *Dalton Trans.*, 2010, 39, 9369-9378.
[19] M. A. Brook, J. B. Grande, and F. Ganachaud. *Adv. Polym. Sci.*, 2011, 235, 161-183.
[20] L. Guo, Z. Zhang, Y. Zhu, J. Li, and Z. Xie. *J. Appl. Polym. Sci.* 2008, 108, 1901-1907.
[21] R. Mosurkal, L. A. Samuelson, V. S. Parmar, J. Kumar, and A. G. Watterson. *Macromolecules*, 2007, 40, 7742-7744.
[22] B. Sharma, A. Azim, H. Azim, and R. A. Gross, E. Zini, M. L. Focarete, and M. Scandola, *Macromolecules*, 2007, 40, 7919-7927.
[23] Y. Poojari, A. Palsule, M. Cai, S. J. Clarson, and R. A. Gross. *Eur. Polym. J.*, 2008, 44, 4139-4145.
[24] Y. Poojari and S. J. Clarson, *Macromolecules*, 2010, 43, 4616-4622
[25] Y. Poojari and S. J. Clarson, *Chem. Commun.*, 2009, 6834-6835.
[26] Y. Poojari and S. J. Clarson, *Silicon*, 2009, 1, 165-172
[27] Y. Poojari and S. J. Clarson, *J. Inorg. Organomet. Polym.*, 2010, 20, 46-52.
[28] M. B. Frampton, I. Subczynska, and P. M. Zelisko. *Biomacromolecules*, 2010, 11, 1818-1825.
[29] M. B. Frampton, J. Séguin, D. Marquardt, T. A. Harroun, and P. M. Zelisko. *J. Mol. Cat. B:Enz.*, 2013, 85-86, 149-155
[30] M. B. Frampton and P. M. Zelisko. *Enz. Microb. Technol.*, Submitted.
[31] R. Panisch, A. R. Bassindale, A. A. Korlyukov, M. B. Pitak, S. J. Coles, and P. G. Taylor. *Organometallics*, 2013, 32, 1732-1742.
[32] Y. A. Pozdnyakova, A. A. Korlyukov, E. G. Kononova, K. A. Lyssenko, A. S. Peregudov, and O. I. Shchegolikhina. *Inorg. Chem.*, 2010, 49, 572-577.
[33] F. J. Feher, D. Soulivong, A. G. Eklund, and K. D. Wyndham. *Chem. Commun.*, 1997, 1185-1186.
[34] F. J. Feher and K. D. Wyndham. *Chem. Commun.*, 1998, 323-324.
[35] A. R. Bassindale, M. Pourny, P. G. Taylor, M. B. Hursthouse, and M. E. Light. *Angew. Chem. Int. Ed.*, 2003, 42, 3488-3490.
[36] A. R. Bassindale, D. J. Parker, M. Pourny, P. G. Taylor, P. N. Horton, and M. B. Hursthouse. *Organometallics*, 2004, 23, 4400-4405.
[37] S. Fabritz, S Hörner, O. Avrutina, and H. Kolmar. *Org. Biomol. Chem.*, 2013, 11, 2224-2236.
[38] R. M. Laine. *J. Mater. Chem.*, 2005, 15, 3725-3744.
[39] D. B. Cordes, P. D. Lickiss, and F. Rataboul. *Chem. Rev.*, 2010, 110, 2081-2173.
[49] F. Wang, X. Lu, and C. He. J. Mater. Chem., 2011, 21, 2775-2782.

41 P. Jutzi, C. Batz, and A. Matluay. Z. Naturforsch. B., 1994, 49, 1689-1692. R. O. R. Costa, W. L. Vasconcelos, R. Tamaki, and R. M. Laine. *Macromolecules,* 2001, 34, 5398-5407.

43 J. H. Jung, and R. M. Laine, *Macromolecules,* 2011, 44, 7263-7272.

44 S. Sulaiman, A. Bhaskar, J. Zhang, R. Guda, T. Goodson, III, and R. M. Laine, *Chem. Mater.,* 2008, 20, 5563-5573.

45 M. Z. Asuncion, and R. M. Laine, *Macromolecules,* 2007, 40, 555-562.

46 Mundy, B P; Ellerd, M G; Favaloro, F G Jr. Name Reactions and Reagents in Organic Synthesis, 2nd Edition. 2005, John Wiley & Sons, Hoboken, N.J.

47 J. B. Williams, A. I. Gusev, and D. M. Hercules. *Macromolecules,* 1996, 29, 8144-8150.

48 S. Yoshida, S. Yamamoto, T. Takamatsu. *Rapid Commun. Mass Spectrom.,* 1998, 12, 535-544.

49 R. E. Tecklenberg, W. E. Wallace, and H. Chen. *Rapid Commun. Mass Spectrom.,* 2001, 15, 2176-2185.

50 T. Fouquet, T. N. T. Phan, and L. Charles. *Rapid Commun. Mass Spectrom.,* 2012, 26, 765-774.

51 R. Baktiar and F. J. Feher. *Rapid Commun. Mass Spectrom.,* 1999, 13, 687-694.

52 J. Falkenhagen, H. Jancke, R. P. Krüger, E. Rikowski, and G. Schulz. *Rapid Commun. Mass Spectrom.,* 2003, 17, 285-290.

53 P. P. Pescarmona, M. E. Raimondi, J. Tetteh, B. McKay, and T. Maschmeyer. J. Phys. Chem. A, 2003, 107, 8886-8892.

54 R. Ito, Y. Kakihana, and Y. Kawakami. *Chem. Lett.,* 2009, 38, 364-365.

55 R. W. McCabe and A. Taylor. *Enz. Microb. Technol.,* 2004, 35, 393-398.

56 M. B. Frampton and P. M. Zelisko. *Chem. Commun.,* 2013, 49, 9269-9271.

57 S. Patkar, J. Vind, E. Kelstrup, M. W. Christensen, A. Svendsen, K. Borch, and O. Kirk. *Chem. Phys. Lipids,* 1998, 93, 95-101.

58 I. Hilker, A. E. J. Schaafsma, R. A. H. Peters, A. Heise, and A. J. Nijenhuis. *Eur. Polym. J.,* 2008, 44, 1441-1450.

59 M. Gargouri, P. Drouet, and M-D. Legoy. *J. Biotechnol.,* 2002, 92, 259-266.

60 C. Berkane, G. Mezoul, T. Lalot, M. Brigodiot, and E. Maréchal. *Macromolecules,* 1997, 30, 7729-7734.

61 Y. Yang, W. Lu, J. Cai, Y. Huo, S. Ouyang, W. Xie, and R. A. Gross. *Macromolecules,* 2011, 44, 1977-1985.

62 M. B. Frampton and P. M. Zelisko. *Enz. Microbiol. Technol.,* 2014, 58-59, 87-92.

63 C. Laane, S. Boeren, K. Vos, and C. Veeger. Biotechnol. Bioeng., 1987, 30, 81-87.

64 P. J. Halling. Enz. Microbial Technol., 1994, 16, 178-206.

65 H. M. Luu and J. C. Hutter. Environ. Health Perspect., 2001, 109, 1095-1101.

66 G. K. Robinson, M. J. Alston, C. J. Knowles, P. S. J. Cheetham, and K. R. Motion. Enz. Microbiol Tech., 1994, 16, 855-863.

67 A. J. Kumar and R. A Gross. Macromolecules, 2000, 1, 133-138.

68 M. B. Frampton, I. Subczynska, and P. M. Zelisko. Biomacromolecules, 2010, 11, 1818-1825.

69 Y. Poojari and S. J. Clarson, J. Inorg. Organomet. Polym., 2010, 20, 46-52.

70 Y. Poojari and S. J. Clarson, Macromolecules, 2010, 43, 4616-4622.

71 Y. Poojari and S. J. Clarson, Silicon, 2009, 1, 165-172.

72 B. Sharma, A. Azim, H. Azim, R. A. Gross, E. Zini, M. L. Focarete, and M. Scandola. Macromolecules, 2007, 40, 7919-7927.

73 Z. Jiang, C. Liu, and R. A. Gross. Macromolecules, 2008, 41, 4671-4680.

74 E. G. Griffith, E. M. Adams N. C. Allen, and V. Vaida. J. Phys. Chem. B., 2012, 116, 7849-7857.

75 C. A. Devries, J. J. Haycraft, Q. Han, F. Noor-e-Ain, J. Raible, P. H. Dussault, and C. J. Eckhardt. Thin Solid Films, 2011, 519, 2430-2437.

76 X. Chen, Q-B. Xue, K-Z. Yang and Q-Z. Zhang. Macromolecules, 1996, 29, 5658-5663.

77 J. J. Haycraft, C. A. DeVries, H. G. Flores, A. Lech, J. P. Hagen, and C. J. Eskhardt. Thin Solid Films, 2007, 515, 2990-2997.

TABLE 1

The temperature dependence of conversion in the polyesterification of the compound of Formula I(a) wherein $R^{1a}$, $R^{1b}$, $R^{1c}$ and $R^{1d}$ are each $(CH_2)_9C(O)OCH_3$ with octane-1,8-diol.

| Temperature (° C.) | Conversion (%, $^1$H NMR) |
| --- | --- |
| 70 | 71 ± 2 |
| 100 | 74 ± 2 |
| 130 | 40 ± 6 |

TABLE 2

Assignment of MALDI-ToF MS peaks from the transesterification of the compound of Formula II(a) wherein $R^{4a}$, $R^{4b}$, $R^{4c}$, $R^{4d}$, $R^{4e}$, $R^{4f}$, $R^{4g}$ and $R^{4h}$ are each $(CH_2)_9C(O)OCH_3$ with octane-1,8-diol via lipase catalysis.[1]

| Assignment | Expected M+ | Expected (M + Na)+ | Found (M + Na)+ |
| --- | --- | --- | --- |
| A | 2492 | 2515 | |
| AB | 2606 | 2629 | 2630 |
| ABcyc | 2574 | 2597 | |
| AB$_2$ | 2720 | 2743 | |
| AB$_2$cyc | 2688 | 2711 | 2704 |
| AB$_2$cyc$^2$ | 2656 | 2679 | 2675 |
| AB$_3$ | 2834 | 2857 | |
| AB$_3$cyc | 2802 | 2825 | |
| AB$_3$cyc$^2$ | 2770 | 2793 | 2789 |
| AB$_3$cyc$^3$ | 2738 | 2761 | 2758 |
| AB$_4$ | 2948 | 2971 | |
| AB$_4$cyc | 2916 | 2939 | |
| AB$_4$cyc$^2$ | 2884 | 2907 | 2903 |
| AB$_4$cyc$^3$ | 2852 | 2875 | 2871 |
| AB$_4$cyc$^4$ | 2820 | 2843 | 2840 |
| AB$_5$ | 3062 | 3085 | |
| AB$_5$cyc | 3030 | 3052 | 3056 |
| AB$_5$cyc$^2$ | 2998 | 3021 | 3017 |
| AB$_5$cyc$^3$ | 2966 | 2989 | 2985 |
| AB$_6$ | 3144 | 3167 | |
| AB$_6$cyc | 3112 | 3135 | 3132 |
| AB$_6$cyc$^2$ | 3080 | 3103 | |
| AB$_7$ | 3258 | 3281 | |
| AB$_7$cyc | 3226 | 3249 | |
| AB$_8$ | 3372 | 3395 | |

[1]The $Q_8$ cube fragment is labelled A and octain-1,8-diol fragments is labelled $B_x$, where x is the number of B units attached to the cube. Where intramolecular esterifications occurred, the $cyc^y$, where y is the number of intramolecular esterifications, label is used. All mass ions are reported as the charge to mass ratio.

TABLE 3

The effect of solvent on the esterification of 50 mM C10D₄ ester and octane-1,8-diol catalyzed by 5 wt % of N435. Reactions were stirred at 150 rpm, 60° C. for 24 h.

| Solvent | logP | % Conversion (NMR) |
|---|---|---|
| THF | 0.5 | 18 |
| Toluene | 2.5 | 58 |
| Hexanes | 3.5 | 58 |
| Isooctane | 4.5 | 29 |
| D4 | 5.1 | 11 |

TABLE 4

The effect of chain length of tetraesters and diols on the N435-catalysed synthesis of macrocyclic oligoesters. Conditions: 25 mM in PhMe, 100° C., 150 rpm, 120 h, 5wt % N435.

| D₄-ester | Diol | % Conv. (NMR) | % (MALDI) |
|---|---|---|---|
| (CH₂)₉CO₂Me | HO~(~)₅~OH | 93 ± 3 | 88 (17-40)* |
| (CH₂)₉CO₂Me | HO~(~)₃~OH | 96 ± 1 | 82 (15-25)* |
| (CH₂)₉CO₂Me | 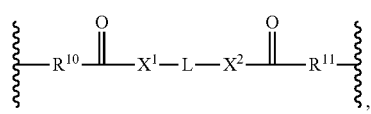 | 21 ± 10 | 0 |
| (CH₂)₆CO₂Me | HO~(~)₅~OH | 46 ± 5 | >2 |
| (CH₂)₆CO₂Me | HO~(~)₃~OH | 43 ± 17 | >2 |
| (CH₂)₄CO₂Me | HO~(~)₅~OH | 5 ± 1 | n.d. |
| (CH₂)₄CO₂Me | HO~(~)₃~OH | 3 ± 1 | n.d |

*Isolated yield after column chromatography (in brackets)

The invention claimed is:

1. A polymeric siloxane-containing hybrid material or a macrocyclic oligoester comprising siloxane moieties selected from cyclic siloxanes and polyhedral siloxanes that are linked intermolecularly or intramolecularly via an organic linker of Formula IV:

$$\{-R^{10}-\overset{O}{\underset{\|}{C}}-X^1-L-X^2-\overset{O}{\underset{\|}{C}}-R^{11}-\}$$ IV wherein
when the siloxane moieties comprise cyclic siloxanes, $R^{10}$ and $R^{11}$ are each independently an alkylene, alkenylene or alkynylene group having at least four carbon atoms;
when the siloxane moieties comprise polyhedral siloxanes, $R^{10}$ and $R^{11}$ are each independently an alkylene, alkenylene or alkynylene group having at least eight carbon atoms;
$X^1$ and $X^2$ are each independently $NR^{12}$ or O;
$R^{12}$ is or $C_{1-6}$alkyl; and
L is an alkylene, alkenylene or alkynylene group having at least six carbon atoms.

2. A coating comprising the polymeric siloxane-containing hybrid material of claim 1.

3. A composite comprising a film of the polymeric siloxane-containing hybrid material of claim 1 coated on a substrate.

4. The polymeric siloxane-containing hybrid material or macrocyclic oligoester comprising siloxane moieties of claim 1, wherein the siloxane moiety comprises a cyclic siloxane.

5. The polymeric siloxane-containing hybrid material or macrocyclic oligoester comprising siloxane moieties of claim 4, wherein $R^{10}$ and $R^{11}$ are each independently $C_{4-40}$alkylene, $C_{4-40}$alkenylene or $C_{4-40}$alkynylene.

6. The polymeric siloxane-containing hybrid material or macrocyclic oligoester comprising siloxane moieties of claim 5, wherein $R^{10}$ and $R^{11}$ are each independently $C_{4-20}$alkylene, $C_{4-20}$alkenylene or $C_{4-20}$alkynylene.

7. The polymeric siloxane-containing hybrid material or macrocyclic oligoester comprising siloxane moieties of claim 6, wherein $R^{10}$ and $R^{11}$ are each independently $C_{4-12}$alkylene, $C_{4-12}$alkenylene or $C_{4-12}$alkynylene.

8. The polymeric siloxane-containing hybrid material or macrocyclic oligoester comprising siloxane moieties of claim 7, wherein $R^{10}$ and $R^{11}$ are each independently $C_{4-12}$alkylene.

9. The polymeric siloxane-containing hybrid material or macrocyclic oligoester comprising siloxane moieties of claim 8, wherein $R^{10}$ and $R^{11}$ are each —(CH₂)₉—.

10. The polymeric siloxane-containing hybrid material or macrocyclic oligoester comprising siloxane moieties of claim 4, wherein the cyclic siloxane is selected from a cyclotrisiloxane, a cyclotetrasiloxane, a cyclopentasiloxane and a cyclohexasiloxane.

11. The polymeric siloxane-containing hybrid material or macrocyclic oligoester comprising siloxane moieties of claim 1, wherein the siloxane moiety comprises a polyhedral siloxane.

12. The polymeric siloxane-containing hybrid material or macrocyclic oligoester comprising siloxane moieties of claim 11, wherein $R^{10}$ and $R^{11}$ are each independently $C_{8-40}$alkylene, $C_{8-40}$alkenylene or $C_{8-40}$alkynylene.

13. The polymeric siloxane-containing hybrid material or macrocyclic oligoester comprising siloxane moieties of claim 12, wherein $R^{10}$ and $R^{11}$ are each independently $C_{8-20}$alkylene, $C_{8-20}$alkenylene or $C_{8-20}$alkynylene.

14. The polymeric siloxane-containing hybrid material or macrocyclic oligoester comprising siloxane moieties of claim 13, wherein $R^{10}$ and $R^{11}$ are each independently $C_{8-12}$alkylene, $C_{8-12}$alkenylene or $C_{8-12}$alkynylene.

15. The polymeric siloxane-containing hybrid material or macrocyclic oligoester comprising siloxane moieties of claim 14, wherein $R^{10}$ and $R^{11}$ are each independently $C_{8-12}$alkylene.

16. The polymeric siloxane-containing hybrid material or macrocyclic oligoester comprising siloxane moieties of claim 11, wherein the polyhedral siloxane is a $Q_8$ silsesquioxane.

17. The polymeric siloxane-containing hybrid material or macrocyclic oligoester comprising siloxane moieties of claim 1, wherein $X^1$ and $X^2$ are each O.

18. The polymeric siloxane-containing hybrid material or macrocyclic oligoester comprising siloxane moieties of claim 1, wherein $X^1$ and $X^2$ are each independently $NR^{12}$ wherein $R^{12}$ is H or $C_{1-6}$alkyl.

19. The polymeric siloxane-containing hybrid material or macrocyclic oligoester comprising siloxane moieties of claim 1, wherein L is $C_{6-40}$alkylene, $C_{6-40}$alkenylene or $C_{6-40}$alkynylene.

20. The polymeric siloxane-containing hybrid material or macrocyclic oligoester comprising siloxane moieties of claim 19, wherein L is $C_{6-14}$alkylene, $C_{6-14}$alkenylene or $C_{6-14}$alkynylene.

21. A macrocyclic oligoester comprising cyclic siloxanes that are linked intramolecularly, or intermolecularly and intramolecularly, via an organic linker of Formula IV as defined in claim 1.

22. The macrocyclic oligoester of claim 21 selected from

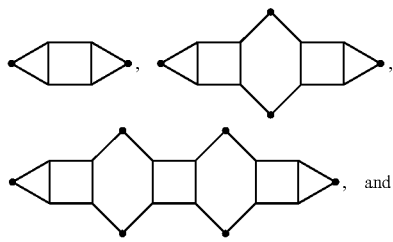

wherein

□ represents a cyclic siloxane,

—• represents —$R^{10}$—C(O)$X^1$-L-$X^2$—H or —$R^{11}$—C(O)$X^2$-L-$X^1$—H, wherein $R^{10}$, $R^{11}$, $X^1$, $X^2$ and L are as defined in claim 1, and

∧ represents an organic linker of the Formula IV as defined in claim 1.

23. The macrocyclic oligoester of claim 22, wherein

□ is cyclotetrasiloxane.

24. The macrocyclic oligoester of claim 22, wherein the macrocyclic oligoester comprises only one cyclic siloxane, and the macrocyclic oligoester is intramolecularly linked via two organic linkers to form an oligoester.

25. The macrocyclic oligoester of claim 24, that is

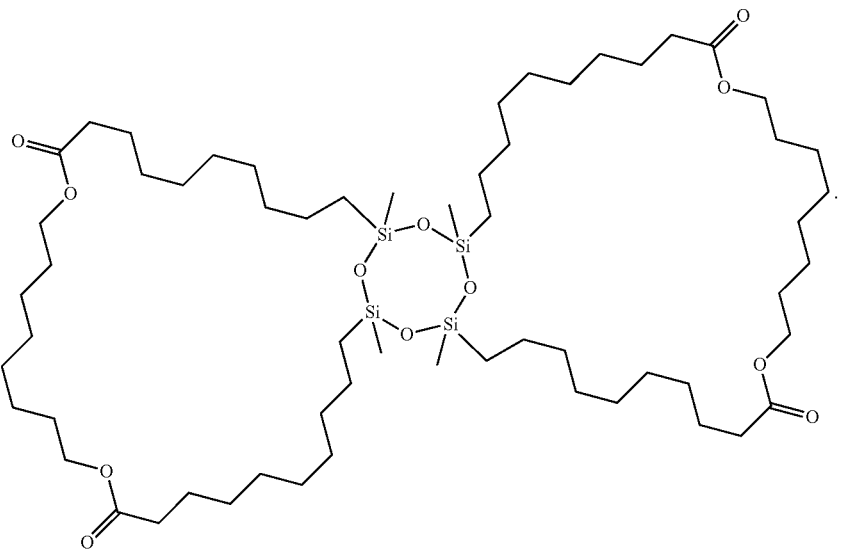 [SMILES: C[Si]12CCCCCCCCCC(=O)OCCCCCCCCOC(=O)CCCCCCCCC[Si](C)(O1)O[Si]1(C)CCCCCCCCCC(=O)OCCCCCCCCOC(=O)CCCCCCCCC[Si](C)(O1)O2]

26. The macrocyclic oligoester of claim 24, that is
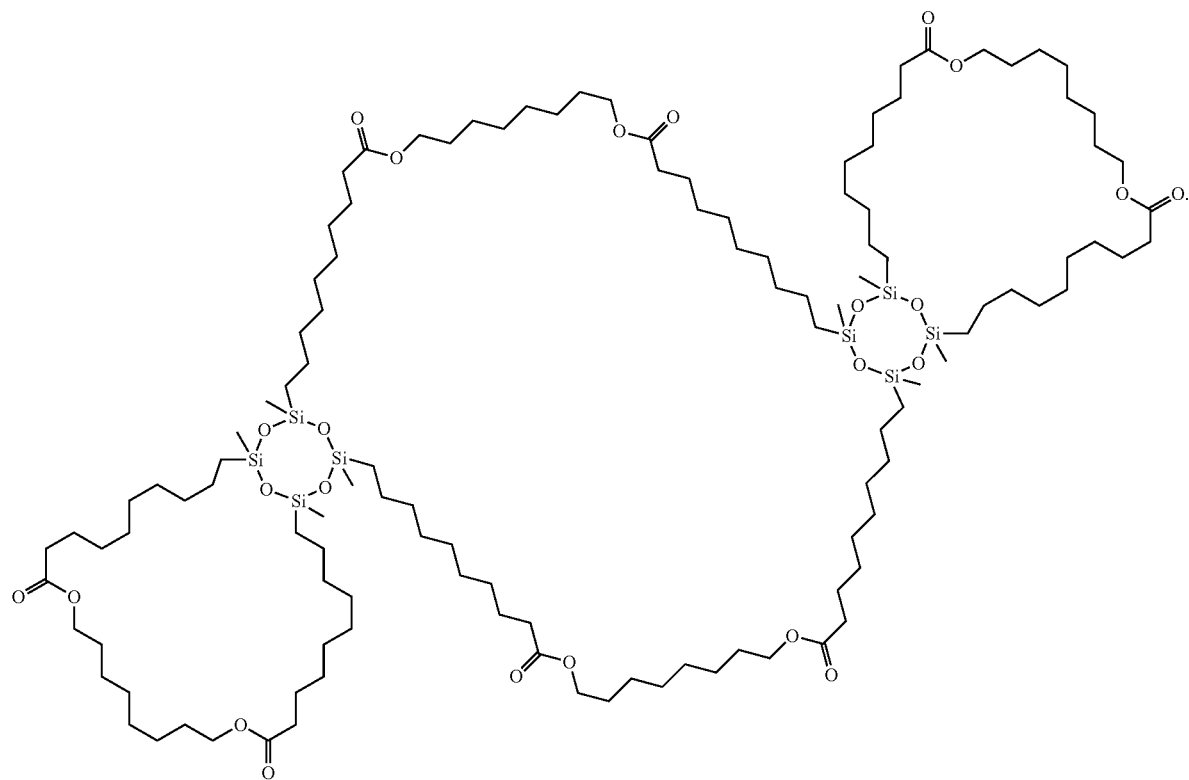 [SMILES: C[Si]12CCCCCCCCCC(=O)OCCCCCCCCOC(=O)CCCCCCCCC[Si](C)(O1)O[Si]1(C)CCCCCCCCCC(=O)OCCCCCCCCOC(=O)CCCCCCCCC[Si]3(C)O[Si]4(C)CCCCCCCCCC(=O)OCCCCCCCCOC(=O)CCCCCCCCC[Si](C)(O4)O[Si](C)(CCCCCCCCCC(=O)OCCCCCCCCOC(=O)CCCCCCCCC[Si](C)(O2)O1)O3]
27. The macrocyclic oligoester of claim 22, wherein two or more cyclic siloxanes are linked intramolecularly and intermolecularly.
* * * * *